(12) United States Patent
Fujiyasu et al.

(10) Patent No.: US 9,199,927 B2
(45) Date of Patent: Dec. 1, 2015

(54) GUANIDINOBENZOIC ACID COMPOUND

(75) Inventors: Jiro Fujiyasu, Chuo-ku (JP); Kazuhiko Ohne, Chuo-ku (JP); Susumu Yamaki, Chuo-ku (JP); Tomoyoshi Imaizumi, Chuo-ku (JP); Takeshi Hondo, Chuo-ku (JP); Keisuke Matsuura, Chuo-ku (JP); Tomohki Satou, Chuo-ku (JP); Satoshi Sasamura, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/344,377

(22) PCT Filed: Sep. 14, 2012

(86) PCT No.: PCT/JP2012/073576
§ 371 (c)(1),
(2), (4) Date: Mar. 12, 2014

(87) PCT Pub. No.: WO2013/039187
PCT Pub. Date: Mar. 21, 2013

(65) Prior Publication Data
US 2014/0378459 A1    Dec. 25, 2014

(30) Foreign Application Priority Data
Sep. 15, 2011  (JP) ................................ 2011-201651

(51) Int. Cl.
| | |
|---|---|
| *A61K 31/47* | (2006.01) |
| *C07C 229/02* | (2006.01) |
| *C07D 215/38* | (2006.01) |
| *C07C 279/18* | (2006.01) |
| *C07D 213/79* | (2006.01) |
| *C07D 215/20* | (2006.01) |
| *C07D 215/48* | (2006.01) |
| *C07D 215/50* | (2006.01) |
| *C07D 333/38* | (2006.01) |
| *C07D 333/40* | (2006.01) |
| *C07D 233/64* | (2006.01) |
| *C07D 257/04* | (2006.01) |
| *C07D 271/06* | (2006.01) |
| *C07D 207/16* | (2006.01) |
| *C07D 277/20* | (2006.01) |
| *C07D 277/56* | (2006.01) |
| *C07D 209/20* | (2006.01) |
| *C07D 209/42* | (2006.01) |
| *C07D 295/12* | (2006.01) |
| *C07D 211/62* | (2006.01) |
| *C07D 217/26* | (2006.01) |
| *C07D 271/07* | (2006.01) |
| *C07D 295/13* | (2006.01) |

(52) U.S. Cl.
CPC ............ *C07C 279/18* (2013.01); *C07D 207/16* (2013.01); *C07D 209/20* (2013.01); *C07D 209/42* (2013.01); *C07D 211/62* (2013.01); *C07D 213/79* (2013.01); *C07D 215/20* (2013.01); *C07D 215/48* (2013.01); *C07D 215/50* (2013.01); *C07D 217/26* (2013.01); *C07D 233/64* (2013.01); *C07D 257/04* (2013.01); *C07D 271/06* (2013.01); *C07D 271/07* (2013.01); *C07D 277/20* (2013.01); *C07D 277/56* (2013.01); *C07D 295/12* (2013.01); *C07D 295/13* (2013.01); *C07D 333/38* (2013.01); *C07D 333/40* (2013.01); *C07B 2200/07* (2013.01); *C07C 2101/02* (2013.01); *C07C 2101/14* (2013.01)

(58) Field of Classification Search
CPC ..... A61K 31/47; C07C 229/02; C07D 215/38
USPC .............. 546/152, 169; 560/34; 514/299, 311
See application file for complete search history.

(56) References Cited

U.S. PATENT DOCUMENTS

| | | | | |
|---|---|---|---|---|
| 4,283,418 | A | * | 8/1981 | Fujii et al. ................... 514/535 |
| 4,532,255 | A | | 7/1985 | Fujii et al. |
| 5,432,178 | A | | 7/1995 | Nakai et al. |
| 2012/0283222 | A1 | | 11/2012 | Konishi et al. |

FOREIGN PATENT DOCUMENTS

| | | | |
|---|---|---|---|
| EP | 0 486 702 | A1 | 5/1992 |
| EP | 0 673 924 | A1 | 9/1995 |
| EP | 0 893 437 | A1 | 1/1999 |

(Continued)

OTHER PUBLICATIONS

Extended European Search Report issued Jan. 26, 2015 in Patent Application No. 12831685.8.

(Continued)

*Primary Examiner* — Golam M M Shameem
(74) *Attorney, Agent, or Firm* — Oblon, McClelland, Maier & Neustadt, L.L.P.

(57) ABSTRACT

[Problem]
Provided is a compound which is useful as an agent for preventing and/or treating renal diseases.

[Means for Solution]
The present inventors have conducted extensive studies on compounds having a trypsin inhibitory action, and as a result, they have found that a guanidinobenzoic acid compound has a trypsin inhibitory action, thereby completing the present invention. The guanidinobenzoic acid compound of the present invention can be used as an agent for preventing and/or treating renal disease as an agent which will substitute low-protein diet therapy, and an agent for preventing and/or treating trypsin-related diseases, for example, pancreatitis, gastroesophageal reflux disease, hepatic encephalopathy, influenza, and the like.

18 Claims, No Drawings

(56) References Cited

FOREIGN PATENT DOCUMENTS

| JP | 52-89640 A | 7/1977 |
|---|---|---|
| JP | 57-53454 A | 3/1982 |
| JP | 5-286922 A | 11/1993 |
| JP | 6-192085 A | 7/1994 |
| JP | 7-53500 A | 2/1995 |
| JP | 8-48664 A | 2/1996 |
| JP | 8-109164 A | 4/1996 |
| JP | 9-124571 A | 5/1997 |
| JP | 10-306025 A | 11/1998 |
| WO | WO 91/18869 A1 | 12/1991 |
| WO | WO 94/13631 A1 | 6/1994 |
| WO | WO 97/37969 A1 | 10/1997 |
| WO | WO 2011/071048 A1 | 6/2011 |

OTHER PUBLICATIONS

Pavol Zlatoidsky, et al., "Synthesis and structure-activity relationship study of the new set of trypsin-like proteinase inhibitors" European Journal of Medicinal Chemistry, XP004186871, vol. 34, No. 12, 1999, pp. 1023-1034.

Office Action issued Jan. 16, 2015 in Eurasian Patent Application No. 201490632 (submitting English translation only).

International Search Report issued Dec. 18, 2012 in PCT/JP2012/073576.

* cited by examiner

GUANIDINOBENZOIC ACID COMPOUND

TECHNICAL FIELD

The present invention relates to a guanidinobenzoic acid compound which is useful as an active ingredient of a pharmaceutical composition, for example, a pharmaceutical composition for treating renal failure.

BACKGROUND ART

Low-protein diet therapy for Chronic Kidney Disease (which will be hereinafter referred to CKD) has been practiced for a long time. The mechanism has not still been clarified, but is thought to (1) reduce the total amount of the nitrogen compounds resulting from the protein, and decrease the glomerular loading, (2) suppress the production of uremic toxins which cause renal injury, (3) suppress the accumulation of phosphorous or potassium, (4) suppress the production of acids, and the like, by inhibiting the intake of the protein derived from diet. In recent years, the effect of the low-protein diet therapy on inhibiting CKD progression has also been proved in some clinical tests ((a) "The New England Journal of Medicine", 1989, Vol. 321, No. 26, p. 1773-1777; (b) "The Lancet", 1991, Vol. 337, No. 8753, p. 1299-1304; (c) "American Journal of Kidney Diseases", 2003, Vol. 41, No. 3, p. S31-S34), and is established in the guidelines (Japan Society of Nephrology, "Evidence-Based CKD Guidelines 2009", 2009, p. 40-49). Recently, it is suggested that the low-protein diet therapy prevent not only the pregression of the CKD but also diabetic nephropathy, chronic nephritis, nephrosis, gout kidney, hepatic encephalopathy, and the like, and thus, is now being practiced clinically. However, it is known that since the therapy, as seen from one point of view, requires specialized knowledge, close cooperation among a doctor, dietitian doctor and a patient is necessary, and further, since the low-protein diet itself is a special diet, it is difficult to practice the diet.

On the other hand, it is known that a compound which inhibits trypsin, which is one of enzymes classified as a serine protease, is useful for diseases involving this enzyme, such as, pancreatitis and gastroesophageal reflux disease, and camostat mesylate (which will be hereinafter described camostat) (A) (Patent Document 1) has been actually used for chronic pancreatitis and gastroesophageal reflux disease in clinical practice. Further, it has also been reported that camostat reduce the urinary albumin excretion in animal models with diabetes mellitus ("Nephron", 1996, Vol. 74, No. 4, p. 709-712).

[Chem. 1]

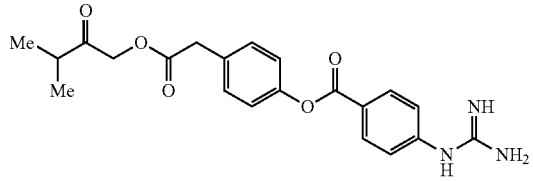

(A)

In addition, it has also been reported that trypsin is involved in the proliferation of influenza viruses, because it is necessary that hemagglutinin (HA) on the virus surface should be cleaved into two subunits of HA1 and HA2 by the trypsin in the airway or mucosal intestinal epithelium in order to obtain the infectivity of the virus, but by inhibition of the trypsin, the cleavage of this HA is suppressed and the virus loses infectivity, whereby the proliferation is suppressed. Therefor, a compound inhibits the trypsin can also be used as an anti-influenza drug ("Antiviral Research", 2011, Vol. 92, No. 1, p. 27-36; (b) "Protease Groups of Individuals which Determine Susceptibility to Infection of Influenza Virus and Pathogenesis of Influenza-Associated Encephalopathy", "The Japanese Journal of Pharmacology", 2003, Vol. 122, p. 45-53).

As a compound exhibiting a trypsin inhibitory action, other than camostat, Compound (B) (Patent Document 2), Compound (C) (Patent Document 3), Compound (D) (Patent Document 4), Compound (E) (Patent Document 5), Compound (F) (Patent Document 6), Compound (G) (Patent Document 7), and Compound (H) (Patent Document 8) have been reported. However, there is no disclosure of the compound of the formula (I) or a salt thereof of the present application as described later in these documents.

[Chem. 2]

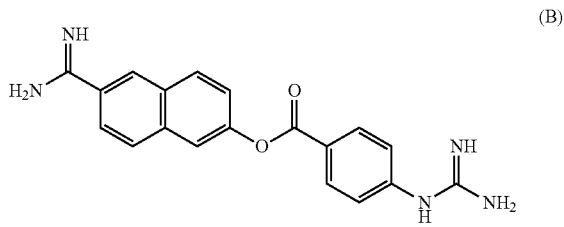

(B)

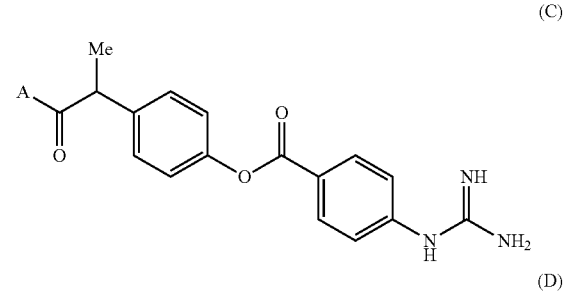

(C)

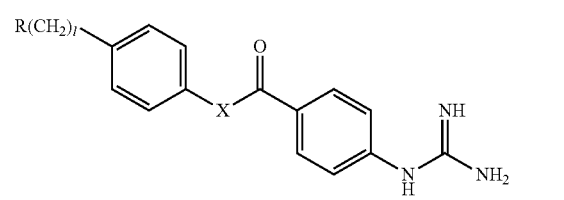

(D)

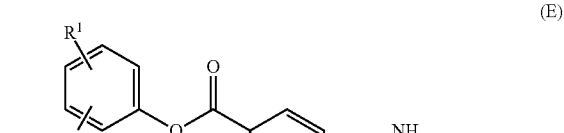

(E)

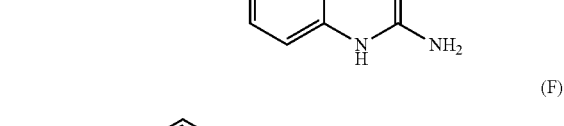

(F)

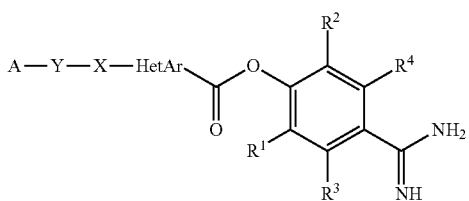

(G)

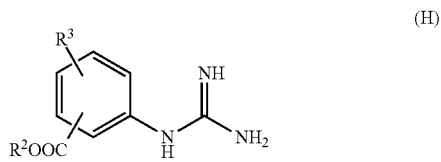

(H)

(In the formula (C), A is —N(R₁, R₂) or the like, and R₁ and R₂ are each H, lower alkyl having 1 to 8 carbon atoms, aralkyl which may have a substituent, or the like. In the formula (D), X is an oxygen atom or a sulfur atom, and R is —C(O)N(R¹)—(CH₂)ₘ-(1-azabicyclo[3.3.0]octan-5-yl) or the like. In the formula (E), R¹ is a hydrogen atom or a halogen atom, and R² is —OCOR³ or the like. In the formula (F), A is (CH₂)ₙ or a styrene group, R² is —NH(CH₂)ₙCOOR⁴, —NHCH—(—R⁵)—COOR⁴, —NH—C₆H₄—(CH₂)ₚ—COOR⁴, or the like, n is 0 to 5, p is an integer of 0 or 1, R⁴ is a hydrogen atom, lower alkyl, or a substituted or unsubstituted benzyl group, R⁵ is a substituted or unsubstituted benzyl group, a methoxycarbonylmethyl group, and the substituent of the substituted benzyl group means a halogen atom, a nitro group, a lower alkyl group, a hydroxy group, an alkoxy group having 2 to 6 carbon atoms, or the like. In the formula (G), X represents lower alkylene or the like, Y represents a carbonyl group or the like, A represents —NR⁶R⁷, R⁶ and R⁷ may be the same as or different from each other and each represents a hydrogen atom, a lower alkyl group which may have a substituent, or the like, or R⁶ and R⁷ may be bonded to each other to form a cyclic amino group which may have a substituent. In the formula (H), R² is a substituted phenyl group, or the like, and R³ is any of various substituents. For the other symbols, refer to the corresponding patent publications.)

Furthermore, as a guanidino compound having an effect of inhibiting the production and release of inflammatory cytokines, Compound (J) (Patent Document 9) has been reported. However, there is no disclosure or suggestion of a specific compound as the compound of the formula (I) or a salt thereof of the present application as described later in these documents.

[Chem. 3]

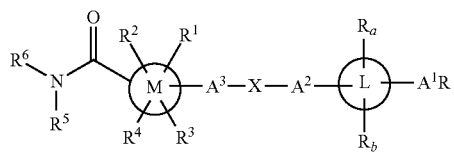

(J)

(wherein R is a guanidino group, an amidino group, or the like, A¹, A² and A³ are each a bond or the like, L is an arylene group or the like, X is —COO— or the like, M is an arylene group, a divalent heterocyclic group, which has at least one hetero atom selected from a nitrogen atom, a sulfur atom, or an oxygen atom, and may form a fused ring, or the like, R⁵ is a hydrogen atom or the like, R⁶ is —CR¹²R¹³—(CH₂)ₘ—R¹¹ or the like, R¹² and R¹³ are a hydrogen atom or the like, R¹¹ is —COOR¹⁶, is R¹⁶ is a hydrogen atom or the like. For the other symbols, refer to the corresponding patent publications.)

RELATED ART

Patent Document

Patent Document 1: JP-A-52-089640

Patent Document 2: JP-A-57-053454

Patent Document 3: Pamphlet of International Publication WO 1994/013631

Patent Document 4: JP-A-7-053500

Patent Document 5: Pamphlet of International Publication WO 1991/018869

Patent Document 6: JP-A-8-048664

Patent Document 7: Pamphlet of International Publication WO 2011/071048

Patent Document 8: Pamphlet of International Publication WO 1997/037969

Patent Document 9: JP-A-9-0124571

DISCLOSURE OF INVENTION

Problems to be Solved by the Invention

A guanidinobenzoic acid compound, which is useful as an active ingredient of a pharmaceutical composition, for example, a pharmaceutical composition for preventing and/or treating renal diseases, is provided.

Means for Solving the Problems

The ingested proteins from meals are digested by various proteases in the duodenum and intestine, and finally absorbed as amino acids or peptides. Trypsin which is produced in the pancreas and secreted in the small intestine in the proteolytic process is a particularly important proteolytic enzyme. Further, by suppressing the enzyme it is expected that the low-protein diet state in which the diet-derived proteolysis is suppressed and the absorption is also suppressed may be mimicked. That is, it is considered that a trypsin inhibitor which acts in the gut may potentially be used as an agent that will substitute low-protein diet therapy. In this regard, the present inventors have conducted extensive studies on compounds having a trypsin inhibitory action. As a result, they have found that the guanidinobenzoic acid compound of the present invention has a trypsin inhibitory action, and is useful for prevention and treatment of renal diseases as an agent which will substitute the low-protein diet therapy, thereby completing the present invention.

Specifically, the present invention relates to a compound of the formula (I) or a salt thereof, and a pharmaceutical composition including the compound of the formula (I) or a salt thereof, and an excipient.

[Chem. 4]

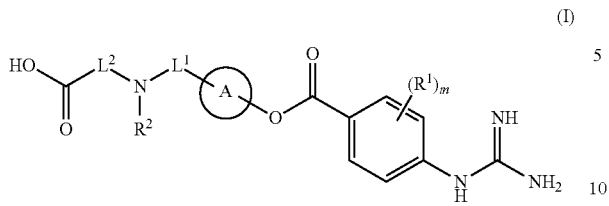

(wherein
Ring A is the following formula (a), (b), or (c),

[Chem. 5]

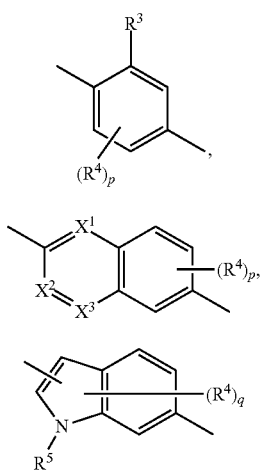

$R^1$'s are the same as or different from each other, and are lower alkyl, halogen, or —OH, $R^2$ is H, (lower alkyl which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted), cycloalkyl which may be substituted, aryl which may be substituted, aromatic heterocycle which may be substituted, non-aromatic heterocycle which may be substituted, or —C(O)-lower alkylene-aryl which may be substituted, $L^1$ is —$Y^1$-lower alkylene-$Y^2$— or —C(O)—N($R^6$)—, and when Ring A is the formula (b) or the formula (c), $L^1$ may also be —C(O)—, $L^2$ is -(lower alkylene which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted)-, —$Y^3$-cyclohexanediyl-$Y^4$— or —$Y^3$-phenylene-$Y^4$—, and $L^2$ may be combined with the nitrogen atom bonded thereto and the $R^2$ group on the nitrogen atom to form cyclic amino which may be substituted, $R^3$ is H, lower alkyl which may be substituted with halogen, halogen, —OH, —O-lower alkyl, cycloalkyl, aryl, aromatic heterocycle or non-aromatic heterocycle, provided that when -$L^2$-N($R^2$)-$L^1$- is —$(CH_2)_n$—NH—C(O)—$(CH_2)_n$—, —CH(—$R^z$)—NH—C(O)—$(CH_2)_n$—, or —$(CH_2)_r$-phenylene-NH—C(O)—$(CH_2)_n$— (wherein n's are the same as or different from each other and represent an integer of 0 to 5, r is 0 or 1, $R^z$ represents benzyl or —$CH_2$—C(O)—$OCH_3$, and the benzyl may have substituent (s) selected from the group consisting of halogen, nitro, lower alkyl, —OH and —O-lower alkyl), and $R^3$ is a group other than H, $R^4$'s are the same as or different from each other, and are lower alkyl which may be substituted with halogen, halogen, —OH, —O-lower alkyl, cycloalkyl, aryl, aromatic heterocycle, or non-aromatic heterocycle, $R^5$ is H or lower alkyl, $R^6$ is H or lower alkyl, $X^1$, $X^2$ and $X^3$ are the same as or different from each other and are CH or N, provided that at least one of $X^1$, $X^2$ and $X^3$ is N, $Y^1$ is a bond or —C(O)—, $Y^2$ is a bond, —N($R^6$)— or —C(O)—N($R^6$)—, $Y^3$'s are the same as or different from each other, and represent a bond or lower alkylene, $Y^4$'s are the same as or different from each other, and are a bond, lower alkylene or —C(O)—, m is an integer of 0 to 4, p is an integer of 0 to 3, and q is an integer of 0 to 4).

Furthermore, unless specified otherwise, in the case where the symbols of the formulae in the present specification are also used in other chemical formulae, the same symbols denote the same meanings.

In the formula (I), for example, in the case where Ring A is the formula (a), the compound means a compound of the following formula (II) or a salt thereof.

[Chem. 6]

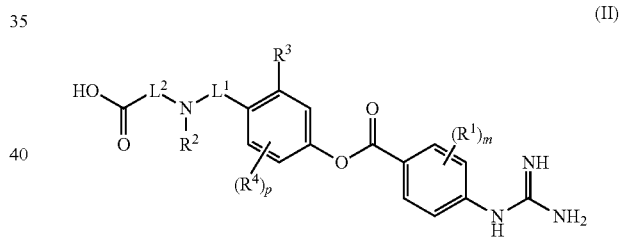

In the formula (I), for example, in the case where $L^1$ is —$Y^1$-lower alkylene-$Y^2$—, the compound means a compound of the following formula (III) or a salt thereof.

[Chem. 7]

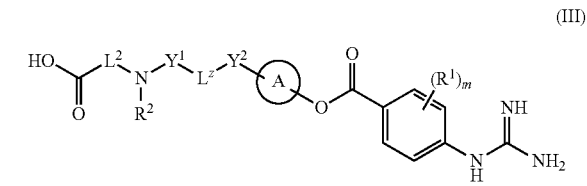

(wherein $L^z$ represents lower alkylene).

Moreover, the present invention relates to a pharmaceutical composition for preventing and/or treating renal diseases (renal failure, diabetic nephropathy, chronic nephropathy, nephrosis, gout kidney, and the like), and trypsin-related diseases (pancreatitis, gastroesophageal reflux disease, hepatic encephalopathy, influenza, and the like), including the compound of the formula (I) or a salt thereof. Further, the pharmaceutical composition includes an agent for preventing and/or treating renal diseases (renal failure, diabetic nephropathy, chronic nephropathy, nephrosis, gout kidney, and the like), and trypsin-related diseases (pancreatitis, gastroesophageal reflux disease, hepatic encephalopathy, influenza, and the like), including the compound of the formula (I) or a salt thereof, In addition, the present invention relates to use of the compound of the formula (I) or a salt thereof for the manufacture of a pharmaceutical composition for preventing and/or treating renal diseases or trypsin-related diseases; a compound of the formula (I) or a salt thereof for preventing and/or treating renal diseases or trypsin-related diseases; and a method for preventing and/or treating renal diseases or trypsin-related diseases, comprising administering an effective amount of the compound of the formula (I) or a salt thereof to a subject. Further, the "subject" is a human or another mammal in need of such prevention or treatment, and in a certain embodiment, a human in need of such prevention or treatment.

Effects of the Invention

The compound of the formula (I) or a salt thereof has a trypsin inhibitory action, and can be used as an agent for preventing and/or treating renal disease as an agent which will substitute low-protein diet therapy, and an agent for preventing and/or treating trypsin-related diseases, for example, pancreatitis, gastroesophageal reflux disease, hepatic encephalopathy, influenza, and the like.

EMBODIMENTS FOR CARRYING OUT THE INVENTION

Hereinafter, the present invention will be described in detail.

In the present specification, the "lower alkyl" refers to linear or branched alkyl having 1 to 6 carbon atoms (which is hereinafter simply referred to as $C_{1-6}$), examples of which include methyl, ethyl, propyl, isopropyl, butyl, tert-butyl, pentyl, and hexyl, or the like; in a further embodiment, $C_{1-3}$ alkyl; in a still further embodiment, methyl, ethyl, propyl, and isopropyl; in a still further embodiment, methyl or ethyl; in a still further embodiment, methyl; and in a still further embodiment, ethyl.

The "lower alkylene" is a divalent group formed by the removal of any hydrogen atom of the "lower alkyl", examples of which include methylene, ethylene, trimethylene, tetramethylene, pentamethylene, hexamethylene, methylmethylene, dimethylmethylene, ethylmethylene, isobutylmethylene, methylethylene, dimethylethylene, ethylethylene, methyltetramethylene, methyltrimethylene, dimethyltetramethylene and the like; in a further embodiment, methylene and ethylene; in a still further embodiment, methylene; and in a still further embodiment, ethylene.

The "lower alkenylene" refers to linear or branched $C_{2-6}$ alkenylene, examples of which include vinylene, ethylidene, propenylene, butenylene, pentenylene, hexenylene, 1,3-butadienylene, 1,3-pentadienylene and the like; in a further embodiment, $C_{2-4}$ alkenylene; and in a still further embodiment, vinylene and ethylidene.

The "cycloalkyl" refers to a saturated hydrocarbon ring group having 3 to 10 ring members, in which the cycloalkyl may have a bridge and may be fused with a benzene ring, and a part of the bonds may be unsaturated, specific examples of which include cyclopropyl, cyclobutyl, cyclopentyl, cyclohexyl, cycloheptyl, cyclooctyl, adamantyl, cyclohexenyl, indanyl, indenyl and the like; in a further embodiment, a saturated hydrocarbon ring group having 3 to 6 ring members; in a still further embodiment, cyclopropyl, cyclopentyl, and cyclohexyl; and in a still further embodiment, cyclohexyl.

The "aryl" refers to a monocyclic to tricyclic aromatic hydrocarbon ring group having 6 to 14 carbon atoms, and specifically, phenyl, naphthyl, anthranyl and the like; in a further embodiment, phenyl; and in a still further embodiment, naphthyl.

The "aromatic heterocycle" is an aromatic monocyclic hetero group having 5 to 6 ring members, containing at least one hetero atom selected from O, N, and S as a ring-constituting atom, or an aromatic bicyclic heterocyclic group formed by fusion of the aromatic monocyclic heterocyclic group with a benzene ring or a thiophene ring, specific examples of which include pyrrolyl, furyl, thienyl, pyrazolyl, imidazolyl, oxazolyl, thiazolyl, oxadiazolyl, thiadiazolyl, tetrazolyl, pyridyl, pyridazinyl, pyrimidinyl, pyrazyl, indolyl, isoindolyl, benzofuryl, benzothienyl, indazolyl, benzoimidazolyl, benzooxazolyl, benzothiazolyl, quinolyl, isoquinolyl, cinnolinyl, phthalazinyl, quinazolinyl, quinoxalinyl, thienopyridyl, thienopyrimidinyl, thienopyrazyl and the like; in a certain embodiment, an aromatic monocyclic heterocycle; in a further embodiment, an aromatic bicyclic heterocycle; in a still further embodiment, thienyl, imidazolyl, thiazolyl, oxadiazolyl, tetrazolyl, indolyl, pyridyl, quinolyl, or isoquinolyl; in a still further embodiment, thienyl, thiazolyl, pyridyl, quinolyl, imidazolyl, or indolyl; in a still further embodiment, thienyl, tetrazolyl, oxadiazolyl, or quinolyl; and in a still further embodiment, quinolyl.

The "non-aromatic heterocycle" is a non-aromatic heterocyclic group having 3 to 7 ring members, containing at least one hetero atom selected from O, N, and S as a ring-constituting atom, and the non-aromatic heterocycle may be combined with a benzene ring, a thiophene ring, or a cyclohexane ring to form a fused ring, and a part of the bonds may be unsaturated. Further, the sulfur atom that is a ring-constituting atom may be oxidized. The non-aromatic heterocycle may also be substituted with -oxo. Specific examples thereof include aziridinyl, azetidinyl, pyrrolidinyl, piperidinyl, azepanyl, oxetanyl, tetrahydrofuryl, tetrahydropyranyl, thietanyl, tetrahydrothienyl, tetrahydrothiopyranyl, 1,1-dioxidotetrahydrothiopyranyl, oxazolidinyl, thiazolidinyl, 1,1-dioxidothiazolidinyl, isooxazolidinyl, isothiazolidinyl, 4,5-dihydro-1,2,4-oxadiazolinyl, 5-oxo-1,2,4-oxadiazolinyl, 1,1-dioxidoisothiazolidinyl, piperazinyl, morpholinyl, thiomorpholinyl, 1,1-dioxidothiomorpholinyl, dioxanyl, indolinyl, isoindolinyl, dihydroquinolyl, tetrahydroquinolyl, dihydroisoquinolyl, tetrahydroisoquinolyl, decahydroisoquinolyl, tetrahydrothienopyridyl, tetrahydrobenzoazepine, tetrahydrobenzodiazepine, dihydrobenzofuryl, dihydrobenzothienyl, dihydrobenzopyranyl, dihydrobenzothiopyranyl, dihydrobenzodioxynyl, benzodioxolyl and the like; in a further embodiment, pyrrolidinyl, tetrahydroisoquinolyl, 5-oxo-1,2,4-oxadiazolinyl, piperidinyl, morpholinyl, and tetrahydropyranyl; and in a still further embodiment, pyrrolidinyl, piperidinyl, morpholinyl, and tetrahydropyranyl.

The "cyclic amino" is a non-aromatic heterocyclic group having a nitrogen atom among the above "non-aromatic heterocycles", which has a bonding arm on the nitrogen atom, and specific examples thereof include pyrrolidin-1-yl, piperidin-1-yl, azepan-1-yl, oxazolidin-3-yl, thiazolidin-3-yl, 1,1-dioxidothiazolidin-3-yl, isoxazolidin-2-yl, isothiazolidin-2-yl, 1,1-dioxidoisothiazolidin-2-yl, piperazin-1-yl, morpholin-4-yl, thiomorpholin-4-yl, 1,1-dioxidothiomorpholin-4-yl, indolin-1-yl, isoindolin-2-yl, 1,2,3,4-tetrahydroquinolin-1-yl, 1,2,3,4-tetrahydroisoquinolin-2-yl, decahydroquinolin-1-yl, decahydroquinolin-2-yl, 4,5,6,7-tetrahydrothieno[3,2-c]pyridin-5-yl and the like; in a further embodiment, pyrrolidin-1-yl, 1,2,3,4-tetrahydroquinolin-1-yl, and 1,2,3,4-tetrahydroisoquinolin-2-yl; and in a still further embodiment, pyrrolidin-1-yl and 1,2,3,4-tetrahydroisoquinolin-2-yl.

The "halogen" refers to F, Cl, Br, or I; and in a further embodiment, F or Cl.

In an embodiment with "phenylene", 1,2-phenylene, 1,3-phenylene and 1,4-phenylene are involved, and in an embodiment with "cyclohexanediyl", cyclohexane-1,2-diyl, cyclohexane-1,3-diyl, and cyclohexane-1,4-diyl are involved.

The "a biological equivalent of —$CO_2H$" means another atom or atom group having common biological properties equivalent to —$CO_2H$, which is capable of releasing acidic protons. Examples thereof include —C(O)—NH—OH, —C(O)—NH—O-lower alkyl, —C(O)—NH—CN, —C(O)—NH—$SO_2$-lower alkyl, —C(O)—NH—$SO_2$—N(lower alkyl)$_2$, or tetrazolyl, oxadiazolonyl, oxadiazolethionyl, and oxathiadiazolyl, thiadiazolonyl, triazolethionyl, hydroxyisoxazolyl; in a further embodiment, —C(O)—NH—$SO_2$-lower alkyl, —C(O)—NH—$SO_2$—N(lower alkyl)$_2$, or tetrazolyl and the like; and in a still further embodiment, tetrazolyl.

In the present specification, the expression "which may be substituted" represents non-substitution or substitution with 1 to 5 substituents". Further, regarding having a plurality of substituents, the substituents may be the same as or different from one other.

Examples of the substituent in "cycloalkyl which may be substituted", "aryl which may be substituted", "aromatic heterocycle which may be substituted", "non-aromatic heterocycle which may be substituted" in $R^2$ of the formula (I), and "cycloalkyl which may be substituted", "aryl which may be substituted", "aromatic heterocycle which may be substituted", "non-aromatic heterocycle which may be substituted", and "cyclic amino which may be substituted" in $L^2$ include substituents selected from Group D1.

Group D1
(1) halogen,
(2) —OH and —O-lower alkyl,
(3) —SH and —S-lower alkyl,
(4) —S(O)-lower alkyl and —S(O)$_2$-lower alkyl,
(5) —CN,
(6) —$NO_2$,
(7) —$NH_2$, —NH-(lower alkyl) and —N(lower alkyl)$_2$,
(8) —C(O)-lower alkyl,
(9) —C(O)—$NH_2$, —C(O)—NH-(lower alkyl) and —C(O)—N(lower alkyl)$_2$,
(10) —O—C(O)-lower alkyl,
(11) cycloalkyl which may be substituted with at least one substituent selected from the group consisting of lower alkyl, —O-lower alkyl, halogen and —OH,
(12) aryl which may be substituted with at least one substituent selected from the group consisting of lower alkyl, —O-lower alkyl, halogen and —OH,
(13) aromatic heterocycle which may be substituted with at least one substituent selected from the group consisting of lower alkyl, —O-lower alkyl, halogen and —OH,
(14) non-aromatic heterocycle which may be substituted with at least one substituent selected from the group consisting of lower alkyl, —O-lower alkyl, halogen and —OH,
(15) —C(O)-lower alkylene-$NH_2$, —C(O)-lower alkylene-NH(lower alkyl) and —C(O)-lower alkylene-N(lower alkyl)$_2$,
(16) —C(O)—O-lower alkyl and —$CO_2H$ or a biological equivalent thereof,
(17) —NH—S(O)$_2$—$NH_2$, and
(18) —O-(aryl which may be substituted with —$CO_2H$),
(19) -oxo, and
(20) lower alkyl, —O-lower alkyl and lower alkenyl, each of which may be substituted with at least one substituent selected from the group consisting of the substituents described in (1) to (18) above.

Another embodiment of Group D1 includes:
(1) halogen,
(2) —OH,
(3) —O-lower alkyl,
(4) aromatic heterocycle which may be substituted with —OH
(5) —$CO_2H$, and
(6) lower alkyl and —O-lower alkyl, each of which may be substituted with at least one substituent selected from the group consisting of the substituents described in (1) to (5) above.

A further embodiment of Group D1 includes:
(1) halogen,
(2) —OH,
(3) —O-lower alkyl,
(4) aromatic heterocycle which may be substituted with —OH,
(5) —$CO_2H$,
(6) lower alkyl which may be substituted with halogen, and
(7) —O-lower alkylene-$CO_2H$.

Embodiments of the compound of the formula (I) or a salt thereof are shown below.

(1) The compound or a salt thereof, wherein Ring A is the formula (a) or the formula (b); in a further embodiment, the compound or a salt thereof, wherein Ring A is the formula (a); in a still further embodiment, the compound or a salt thereof, wherein Ring A is the formula (b); and in a still further embodiment, the compound or a salt thereof, wherein Ring A is the formula (a), and $R^3$ in the formula (a) is halogen.

(2) The compound or a salt thereof, wherein $R^1$ is lower alkyl; and in a further embodiment, the compound or a salt thereof, wherein $R^1$ is halogen.

(3) The compound or a salt thereof, wherein $R^2$ is lower alkyl which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted, cycloalkyl which may be substituted with —$CO_2H$, non-aromatic heterocycle, or H; in a further embodiment, the compound or a salt thereof, wherein $R^2$ is lower alkyl which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted, or H; in a further embodiment, the compound or a salt thereof, wherein $R^2$ is lower alkyl which may be substituted with at least one substituent selected from the group consisting of —$CO_2H$, —OH, (aryl which may be substituted with a group selected from the group consisting of —O-lower alkyl, halogen, —$CO_2H$, —O— lower alkylene-$CO_2H$, —$NHSO_2NH_2$, -lower alkylene-$CO_2H$ and (aromatic heterocycle which may be substituted with —OH)), (aromatic heterocycle which may be substituted with —$CO_2H$) and (non-aromatic heterocycle which may be substituted with —$CO_2H$), cycloalkyl which may be substituted with —$CO_2H$, non-aromatic heterocycle, or H; in a still further embodiment, the compound or a salt thereof, wherein $R^2$ is lower alkyl which is substituted with at least one substituent selected from the group consisting of —$CO_2H$, aryl substituted with one or more —$CO_2H$, and aromatic heterocycle substituted with one or more —$CO_2H$, or H; in a still further embodiment, the compound or a salt thereof, wherein $R^2$ is lower alkyl which is substituted with at least one substituent selected from the group consisting of —$CO_2H$ and aromatic heterocycle substituted with one or more —$CO_2H$, or H; in a still further embodiment, the compound or a salt thereof, wherein $R^2$ is lower alkyl substituted with —$CO_2H$, or H; in a still further embodiment, the compound or a salt thereof, wherein $R^2$ is lower alkyl which is substituted with at least one substituent selected from the group consisting of —$CO_2H$ and aromatic heterocycle substituted with one or more —$CO_2H$; in a still further embodiment, the compound or a salt thereof, wherein $R^2$ is lower alkyl substituted with —$CO_2H$; and in a still further embodiment, the compound or a salt thereof, wherein $R^2$ is H.

(4) The compound or a salt thereof, wherein $L^1$ is —C(O)-lower alkylene-, —C(O)—N($R^6$)—, —C(O)-lower alkylene-N($R^6$)—, -lower alkylene-C(O)—N($R^6$)—, -lower alkylene-or —C(O)—; in a further embodiment, the compound or a salt thereof, wherein $L^1$ is -lower alkylene-, —C(O)-lower alkylene-, -lower alkylene-C(O)—N($R^6$)— or —C(O)—N($R^6$)—; in a further embodiment, the compound or a salt thereof, wherein $L^1$ is —C(O)-lower alkylene-, —C(O)—N($R^6$)— or —C(O)—; in a still further embodiment, the compound or a salt thereof, wherein $L^1$ is —C(O)-lower alkylene-, —C(O)—N(lower alkyl)- or —C(O)—; in a still further embodiment, the compound or a salt thereof, wherein $L^1$ is —C(O)-lower alkylene- or —C(O)—N($R^6$)—; in a still further embodiment, the compound or a salt thereof, wherein $L^1$ is —C(O)-lower alkylene- or —C(O)—N(lower alkyl)-; in a still further embodiment, the compound or a salt thereof, wherein $L^1$ is —C(O)-lower alkylene- or —C(O)—; in a still further embodiment, the compound or a salt thereof, wherein $L^1$ is —C(O)-lower alkylene-; in a still further embodiment, the compound or a salt thereof, wherein $L^1$ is —C(O)—N(lower alkyl)-; and in a still further embodiment, the compound or a salt thereof, wherein $L^1$ is —C(O)—.

(5) The compound or a salt thereof, wherein $L^2$ is -(lower alkylene which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted)-, -lower alkylene-phenylene-, -phenylene-lower alkylene- or -lower alkylene-phenylene-lower alkylene-; in a further embodiment, the compound or a salt thereof, wherein $L^2$ is -(lower alkylene which may be substituted with at least one substituent selected from the group consisting of aromatic heterocycle which may be substituted with at least one group selected from the group consisting of —OH and —$CO_2H$, and aryl which may be substituted with a substituent selected from the group consisting of lower alkyl which may be substituted with halogen, halogen, —OH, —O-lower alkyl, —$CO_2H$ and —O-lower alkylene-$CO_2H$)—, -lower alkylene-phenylene-, -phenylene-lower alkylene- or -lower alkylene-phenylene-lower alkylene-; in a further embodiment, the compound or a salt thereof, wherein $L^2$ is lower alkylene substituted with aryl which may be substituted with a substituent selected from the group consisting of lower alkyl which may be substituted with halogen, halogen, —OH, —O-lower alkyl, —$CO_2H$ and —O-lower alkylene-$CO_2H$, -lower alkylene-phenylene-, -phenylene-lower alkylene- or -lower alkylene-phenylene-lower alkylene-; in a still further embodiment, the compound or a salt thereof, wherein $L^2$ is -lower alkylene which may be substituted with aryl which may be substituted-, -lower alkylene-phenylene-, -phenylene-lower alkylene- or -lower alkylene-phenylene-lower alkylene-; in a still further embodiment, the compound or a salt thereof, wherein $L^2$ is -(lower alkylene which may be substituted with aryl which may be substituted with at least one substituent selected from the group consisting of —$CO_2H$ and —O-lower alkylene-$CO_2H$)—, -lower alkylene-phenylene-, -phenylene-lower alkylene-, -lower alkylene-phenylene-lower alkylene-; in a still further embodiment, the compound or a salt thereof, wherein $L^2$ is -(lower alkylene which may be substituted with aryl which may be substituted with —O-lower alkylene-$CO_2H$)— or -phenylene-lower alkylene-; in a still further embodiment, the compound or a salt thereof, wherein $L^2$ is -lower alkylene- or -phenylene-lower alkylene-; in a still further embodiment, the compound or a salt thereof, wherein $L^2$ is lower alkylene substituted with aryl which may be substituted with a substituent selected from the group consisting of lower alkyl which may be substituted with halogen, halogen, —OH, —O-lower alkyl, —$CO_2H$ and —O-lower alkylene-$CO_2H$; in a still further embodiment, the compound or a salt thereof, wherein $L^2$ is -phenylene-$C_{1-3}$ alkylene-; and in a still further embodiment, the compound or a salt thereof, wherein $L^2$ is —$C_{1-3}$ alkylene-phenylene-.

(6) The compound or a salt thereof, wherein $R^3$ is lower alkyl which may be substituted with halogen, halogen, cycloalkyl or aryl; in a further embodiment, the compound or a salt thereof, wherein $R^3$ is lower alkyl substituted with halogen, halogen, cycloalkyl or aryl; in a further embodiment, the compound or a salt thereof, wherein $R^3$ is lower alkyl which may be substituted with halogen, or halogen; in a still further embodiment, the compound or a salt thereof, wherein $R^3$ is lower alkyl substituted with F, or halogen; in a still further embodiment, the compound or a salt thereof, wherein $R^3$ is lower alkyl substituted with F; and in a still further embodiment, the compound or a salt thereof, wherein $R^3$ is halogen.

(7) The compound or a salt thereof, wherein $R^4$ is halogen.

(8) The compound or a salt thereof, wherein $R^5$ is H or $C_{1-3}$ alkyl; in a further embodiment, the compound or a salt thereof, wherein $R^5$ is H; and in a further embodiment, the compound or a salt thereof, wherein $R^5$ is $C_{1-3}$ alkyl.

(9) The compound or a salt thereof, wherein $R^6$ is lower alkyl; in a further embodiment, the compound or a salt thereof, wherein $R^6$ is $C_{1-3}$ alkyl; and in a further embodiment, the compound or a salt thereof, wherein $R^6$ is methyl.

(10) The compound or a salt thereof, wherein the total number of N's of $X^1$, $X^2$ and $X^3$ is 1; in a further embodiment, the compound or a salt thereof, wherein $X^1$ is N, and $X^2$ and $X^3$ are CH; and in a further embodiment, the compound or a salt thereof, wherein $X^3$ is N, and $X^1$ and $X^2$ are CH.

(11) The compound or a salt thereof, wherein m is an integer of 0 to 2; and in a further embodiment, the compound or a salt thereof, wherein m is 0.

(12) The compound or a salt thereof, wherein p is an integer of 0 or 1; in a further embodiment, the compound or a salt thereof, wherein p is 0; and in a further embodiment, the compound or a salt thereof, wherein p is 1.

(13) The compound or a salt thereof, wherein q is an integer of 0 or 1; and in a further embodiment, the compound or a salt thereof, wherein q is 0.

(14) The compound or a salt thereof, which is a combination of any two or more of the embodiments of (1) to (13) as described above.

The compound or a salt thereof, which is a combination of any two or more of the embodiments of (1) to (13) as described above, is also included in the present invention, as described in (14) above, and the specific examples thereof also include the following embodiments.

(15) The compound or a salt thereof, wherein Ring A is the formula (a) or the formula (b), m is 0, and p is an integer of 0 or 1.

(16) The compound or a salt thereof as described in (15), wherein Ring A is the formula (a), and $R^3$ is lower alkyl which may be substituted with halogen, halogen, cycloalkyl or aryl.

(17) The compound or a salt thereof as described in (16), wherein $R^2$ is lower alkyl which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted, or H, $L^1$ is -lower alkylene-, —C(O)-lower alkylene-, -lower alkylene-C(O)—N($R^6$)— or —C(O)—N($R^6$)—, $L^2$ is -(lower alkylene which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted)-, -lower alkylene-phenylene-, -phenylene-lower alkylene- or -lower alkylene-phenylene-lower alkylene-.

(18) The compound or a salt thereof as described in (17), wherein $R^3$ is halogen, $R^2$ is lower alkyl which is substituted with at least one substituent selected from the group consisting of —$CO_2H$, aryl substituted with one or more —$CO_2H$ and aromatic heterocycle substituted with one or more —$CO_2H$, or H, p is 0, $L^1$ is —C(O)-lower alkylene- or —C(O)—N($R^6$)—, $L^2$ is -(lower alkylene which may be substituted with aryl which may be substituted with at least one substituent selected from the group consisting of —$CO_2H$ and —O-lower alkylene-$CO_2H$)—, -lower alkylene-phenylene-, -phenylene-lower alkylene-, or -lower alkylene-phenylene-lower alkylene-.

(19) The compound or a salt thereof as described in (18), wherein $L^2$ is -(lower alkylene which may be substituted with aryl which may be substituted with —O-lower alkylene-$CO_2H$)— or -phenylene-lower alkylene-.

(20) The compound or a salt thereof, wherein Ring A is the formula (b), $X^1$ is N, $X^2$ and $X^3$ are CH, $L^1$ is —C(O)—, $L^2$ is -lower alkylene which may be substituted with aryl which may be substituted-, -lower alkylene-phenylene-, -phenylene-lower alkylene- or -lower alkylene-phenylene-lower alkylene-, $R^2$ is lower alkyl which is substituted with at least one substituent selected from the group consisting of —$CO_2H$ and aromatic heterocycle substituted with one or more —$CO_2H$, or H, m is 0, and p is 0.

(21) The compound or a salt thereof as described in (20), wherein $L^2$ is -lower alkylene-, -phenylene-lower alkylene- or -lower alkylene-phenylene-lower alkylene-, $R^2$ is lower alkyl which is substituted with at least one substituent selected from the group consisting of —$CO_2H$ and aromatic heterocycle substituted with one or more —$CO_2H$.

(22) The compound or a salt thereof as described in (21), wherein $L^2$ is -lower alkylene- or -phenylene-lower alkylene-.

(23) The compound or a salt thereof, wherein Ring A is the formula (a) or the formula (b), $R^2$ is lower alkyl which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted, or H, m is 0, p is an integer of 0 to 1, and $L^1$ is —C(O)-lower alkylene-, —C(O)—N($R^6$)— or —C(O)—, $L^2$ is -(lower alkylene which may be substituted with at least one substituent selected from the group consisting of halogen, —$CO_2H$, —OH, —O-lower alkyl, cycloalkyl which may be substituted, aryl which may be substituted, aromatic heterocycle which may be substituted, and non-aromatic heterocycle which may be substituted)-, -lower alkylene-phenylene-, -phenylene-lower alkylene- or -lower alkylene-phenylene-lower alkylene-.

(24) The compound or a salt thereof as described in (23), wherein Ring A is the formula (a), $R^2$ is lower alkyl substituted with —$CO_2H$, or H, $R^3$ is halogen, and p is 0.

(25) The compound or a salt thereof as described in (23), wherein Ring A is the formula (b), $X^1$ is N, $X^2$ and $X^3$ are CH, $R^2$ is lower alkyl substituted with —$CO_2H$, or H, and p is 0.

Examples of the specific compounds included in the compound of the formula (I) or a salt thereof include the following compounds:

N-({4-[(4-carbamimidamidobenzoyl)oxy]-2-chlorophenyl}acetyl)-4-carboxy-L-phenylalanine, 3-{[(3-{4-[(4-carbamimidamidobenzoyl)oxy]-2-chlorophenyl}propanoyl)(carboxymethyl)amino]methyl}benzoic acid, N-(3-{4-[(4-carbamimidamidobenzoyl)oxy]-2-chlorophenyl}propanoyl)-N-[3-(carboxymethyl)phenyl]glycine, 3-{[(3-{4-[(4-carbamimidamidobenzoyl)oxy]-2-chlorophenyl}propanoyl)(2-carboxyethyl)amino]methyl}benzoic acid, 2-{[(3-{4-[(4-carbamimidamidobenzoyl)oxy]-2-chlorophenyl}propanoyl)amino]methyl}benzoic acid, 2-{[(3-{4-[(4-carbamimidamidobenzoyl)oxy]-2-chlorophenyl}propanoyl)(carboxymethyl)amino]methyl}benzoic acid, N-({4-[(4-carbamimidamidobenzoyl)oxy]-2-chlorophenyl}acetyl)-O-(carboxymethyl)-L-tyrosine, 3-{2-[(3-{4-[(4-carbamimidamidobenzoyl)oxy]-2-chlorophenyl}propanoyl)(carboxymethyl)amino]ethyl}benzoic acid, 3-{[({6-[(4-carbamimidamidobenzoyl)oxy]quinolin-2-yl}carbonyl)(carboxymethyl)amino]methyl}benzoic acid, 3-{[(2-{4-[(4-carbamimidamidobenzoyl)oxy]-2-chlorophenyl}propanoyl)(carboxymethyl)amino]methyl}benzoic acid, 3-({[{4-[(4-carbamimidamidobenzoyl)oxy]-2-chlorophenyl}(methyl)carbamoyl](carboxymethyl)amino}methyl)benzoic acid, 4-{[(3-{4-[(4-carbamimidamidobenzoyl)oxy]-2-chlorophenyl}propanoyl)(carboxymethyl)amino]methyl}thiophene-2-carboxylic acid, 5-{[(3-{4-[(4-carbamimidamidobenzoyl)oxy]-2-chlorophenyl}propanoyl)(carboxymethyl)amino]methyl}isophthalic acid, N-(3-{4-[(4-carbamimidamidobenzoyl)oxy]-2-chlorophenyl}propanoyl)-N-[3-(carboxymethyl)benzyl]glycine, 4-{[({6-[(4-carbamimidamidobenzoyl)oxy]quinolin-2-yl}carbonyl)(carboxymethyl)amino]methyl}thiophene-2-carboxylic acid, N-({4-[(4-carbamimidamidobenzoyl)oxy]-2-chlorophenyl}acetyl)-O-(2-carboxypropan-2-yl)-L-tyrosine, N-(3-{4-[(4-carbamimidamidobenzoyl)oxy]-2-chlorophenyl}propanoyl)-O-(2-carboxypropan-2-yl)-L-tyrosine, 4-({({6-[(4-carbamimidamidobenzoyl)oxy]quinolin-2-yl}carbonyl)[(1R)-1-carboxyethyl]amino}methyl)thiophene-2-carboxylic acid, 3-{[(2-{4-[(4-carbamimidamidobenzoyl)oxy]-2-chlorophenyl}propanoyl)(carboxymethyl)amino]methyl}benzoic acid, 4-({[{4-[(4-carbamimidamidobenzoyl)oxy]-2-chlorophenyl}(methyl)carbamoyl](carboxymethyl)amino}methyl)thiophene-2-carboxylic acid, N-({6-[(4-carbamimidamidobenzoyl)oxy]quinolin-2-yl}carbonyl)-N-[4-(carboxymethyl)benzyl]glycine, or N-({6-[(4-carbamimidamidobenzoyl)oxy]-1H-indol-2-yl}carbonyl)-L-phenylalanine, or a salt thereof.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystalline substances of the compound of the formula (I) and salts thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacement of the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4$^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group at the stage from a starting material to an intermediate, or by carrying out the reaction using the obtained compound of the formula (I), as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the references appended in the present description. Further, the preparation methods of the present invention are not limited to the examples as shown below.

(Production Process 1)

[Chem. 8]

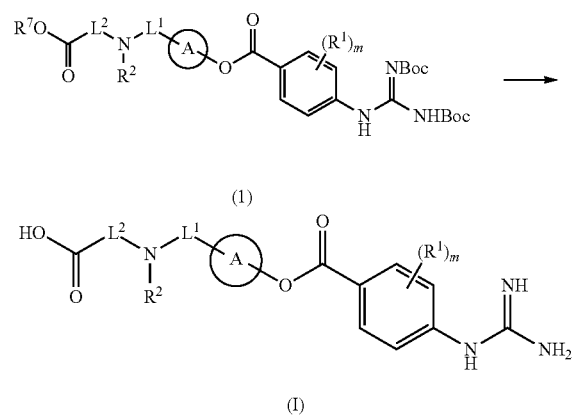

(wherein Boc represents tert-butoxycarbonyl, and $R^7$ represents H or tert-butyl).

The present production process is a method for preparing a compound (I) which is the compound of the present invention by deprotecting a compound 1.

The present reaction is carried out by using the compound 1 and a deprotecting reagent in equivalent amounts, or either thereof in an excess amount, and stirring the mixture in a solvent which is inert to the reaction or in the absence of a solvent, in a range of from cooling to heating and refluxing, usually for 0.1 hours to 5 days. Examples of the solvent used herein are not particularly limited, but include ethers such as diethyl ether, tetrahydrofuran, dioxane, dimethoxyethane and the like, halogenated hydrocarbons such as dichloromethane, 1,2-dichloroethane, chloroform and the like. Examples of the deprotecting reagent are not particularly limited, but include a solution of hydrogen chloride in dioxane, a solution of hydrogen chloride in ethyl acetate, trifluoroacetic acid and the like.

(Preparation of Starting Compound)

In the preparation method above, the starting compound can be prepared by using any of, for example, the methods below, the methods described in Preparation Examples as described later, known methods, or modified methods thereof.

(Starting Material Synthesis 1)

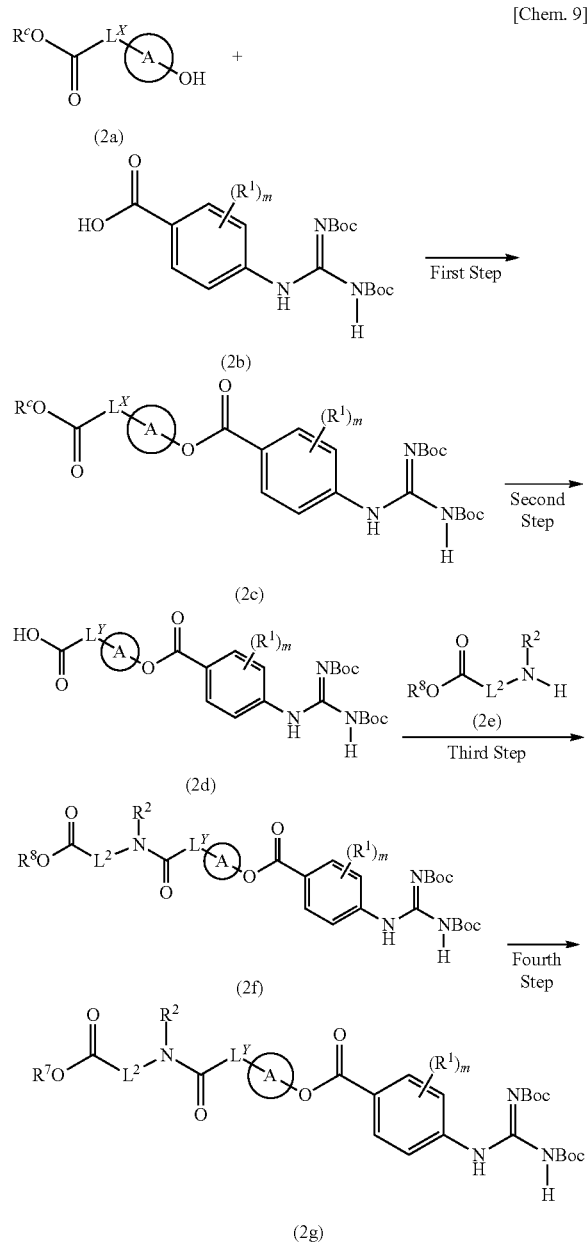

(wherein $L^X$ represents a bond, —N($R^6$)—, -lower alkylene-N($R^6$)—, -lower alkylene-C(O)—N($R^6$)—, -lower alkylene- or -lower alkenylene, $L^Y$ represents a bond, —N($R^6$)—, -lower alkylene-N($R^6$)—, -lower alkylene-C(O)—N($R^6$)— or -lower alkylene-, $R^c$ represents benzyl, benzyloxymethyl, phenacyl, triphenylmethyl, 9-anthrylmethyl, 2-(9,10-dioxo) anthrylmethyl, piperonyl or trimethylsilyl, and $R^8$ represents benzyl, benzyloxymethyl or tert-butyl).

The production process is a method for preparing a compound 2g, in which $L^1$ is —C(O)-lower alkylene-, —C(O)- lower alkylene-N($R^6$)—, —C(O)—, —C(O)—N($R^6$)— or —C(O)-lower alkylene-C(O)—N($R^6$)—, among the compounds 1 of Production Process 1.

(First Step)

The present step is a step of obtaining a compound 2c by the condensation reaction of a compound 2a with a compound 2b prepared by the method described in Tetrahedron Letters, 1993, Vol. 34, No. 21, p. 3389-3392, or a method equivalent thereto.

The present step is carried out by using the compound 2a and the compound 2b in equivalent amounts, or either thereof in an excess amount, and stirring the mixture, in a solvent which is inert to the reaction, in a range of from cooling to heating and refluxing, and preferably at −20° C. to 60° C., usually 0.1 hours to 5 days, in the presence of a condensing agent. Examples of the solvent used herein are not particularly limited, but include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran (THF), dioxane, dimethoxyethane and the like, N,N-dimethylformamide (DMF), dimethyl sulfoxide (DMSO), ethyl acetate, acetonitrile, water, or a mixture thereof. Examples of the condensing agent include, but are not limited to, 1-(3-dimethylaminopropyl)-3-ethylcarbodiimide, dicyclohexylcarbodiimide, 1,1'-carbonyldiimidazole, diphenylphosphorylazide, phosphorus oxychloride, O-(7-azabenzotriazol-1-yl)-N,N,N',N'-tetramethyluroniumhexafluorophosphate (HATU) and the like. It is preferable in some cases for the progress of the reaction to use an additive such as 1-hydroxybenzotriazole. In addition, it is preferable in some cases for the progress of the reaction to use organic bases such as triethylamine, N,N-diisopropylethylamine, N-methylmorpholine, dimethylaminopyridine, pyridine and the like, or inorganic bases such as potassium carbonate, sodium carbonate, potassium hydroxide and the like.

(Second Step)

The present step is a step of obtaining a compound 2d by deprotecting the $R^c$ group in the ester group moiety ($R^cO$—C(O)—) in the compound 2c.

The present step is carried out by stirring the compound 2c in a solvent which is inert to the reaction, in a range from at room temperature to heating and refluxing, and preferably at room temperature, usually for 0.1 hours to 5 days, under a hydrogen atmosphere, in the presence of a metal catalyst. Examples of the solvent used herein are not particularly limited, but include alcohols such as methanol, ethanol, 2-propanol and the like, ethers such as diethyl ether, tetrahydrofuran, dioxane, dimethoxyethane and the like, water, ethyl acetate, N,N-dimethylformamide, dimethyl sulfoxide and a mixture thereof. As the metal catalyst, palladium catalysts such as palladium carbon, palladium black, palladium hydroxide and the like, platinum catalysts such as a platinum plate, platinum oxide and the like, nickel catalysts such as reduced nickel, Raney nickel and the like, rhodium catalysts such as tristriphenylphosphine chlororhodium and the like, or iron catalysts such as reduced iron and the like are suitably used. It is preferable to carry out the reaction under a hydrogen atmosphere in a range of normal pressure to 3 atm. It is preferable in some cases for the progress of the reaction to use an inorganic acid such as hydrochloric acid.

Furthermore, a compound formed by reducing a double bond of a compound having -lower alkenylene in an Lx part by the present step can be synthesized simultaneously.

(Third Step)

The present step is a step of obtaining a compound 2f by the amidation of the compound 2d with a predetermined amine compound 2e.

For the amidation, the method of the first step in the starting material synthesis 1 can be used, and further, 1-chloro-N,N, 2-trimethylprop-1-en-1-amine described in Journal of the Chemical Society. Chemical communications, 1979, Vol. 24, p. 1180-1181 can also be used instead of the condensing agent.

(Fourth Step)

The present step is a step of obtaining a compound 2g from the compound 2f by deprotecting a benzyl group or a benzyloxymethyl group, in addition to the above step, in a case where $R^8$ is the benzyl group or the benzyloxymethyl group.

For the deprotection, the method of the second step in the starting material synthesis 1 can be used.

(Starting Material Synthesis 2)

For the amidation, the method of the first step in the starting material synthesis 1 can be used.

(Second Step)

The present step is a step of obtaining a compound 2f by the condensation reaction of the compound 3b with the compound 2b prepared by the method described in Tetrahedron Letters, 1993, Vol. 34, No. 21, p. 3389-3392, or a method equivalent thereto.

For the condensation reaction, the method of the first step in the starting material synthesis 1 can be used.

(Third Step)

The present step is a step of obtaining the compound 2g from the compound 2f by deprotecting a benzyl group or a benzyloxymethyl group, in addition to the above step, in a case where $R^8$ is the benzyl group or the benzyloxymethyl group.

For the deprotection, the method of the second step in the starting material synthesis 1 can be used.

(Starting Material Synthesis 3)

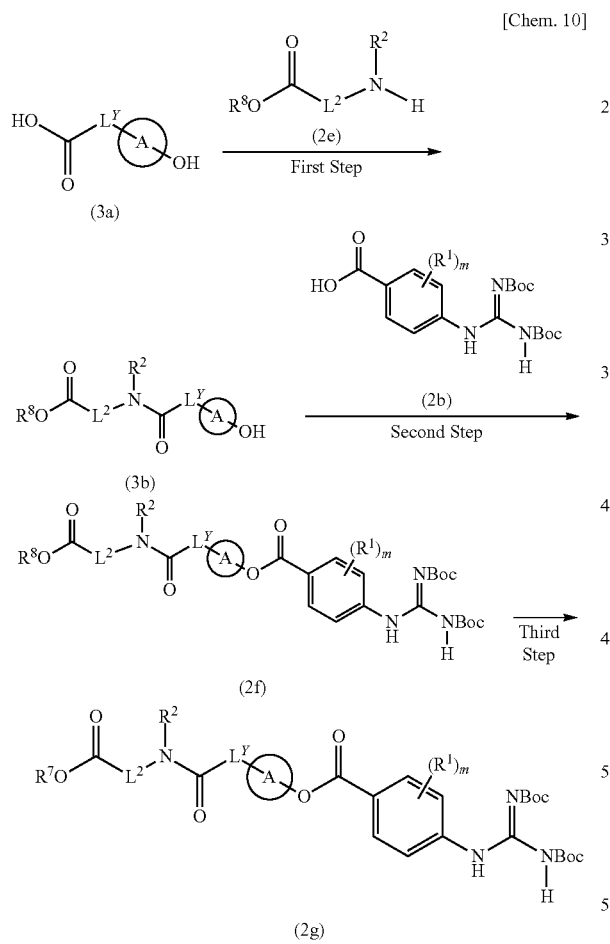

[Chem. 10]

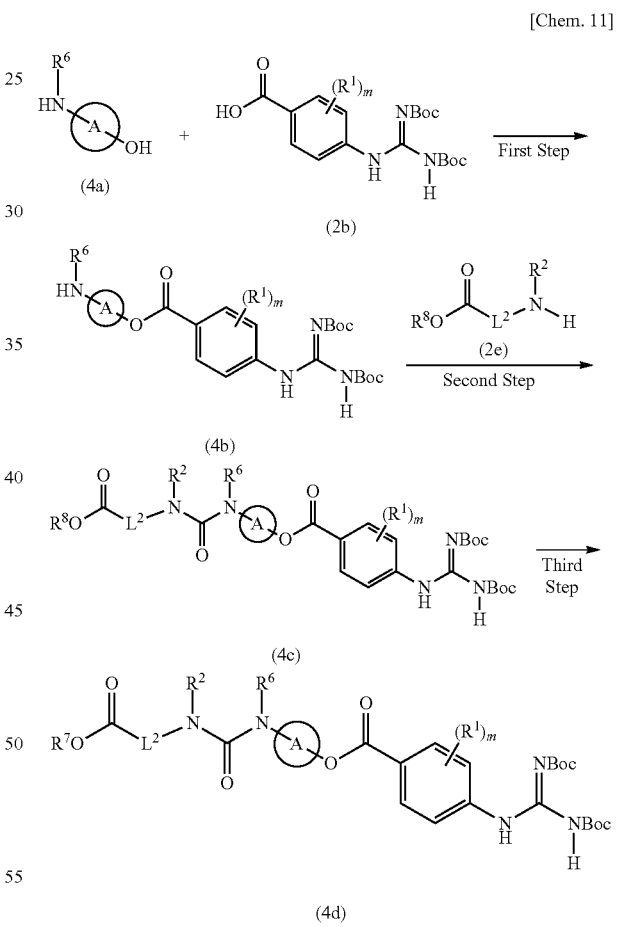

[Chem. 11]

The present production process is a method for preparing a compound 2g in which $L^1$ is —C(O)-lower alkylene-, —C(O)-lower alkylene-N($R^6$)—, —C(O)—, —C(O)—N($R^6$)— or —C(O)-lower alkylene-C(O)—N($R^6$)—, among the starting compounds 1 of the production process 1.

(First Step)

The present step is a step of obtaining a compound 3b by the amidation of the compound 3a with a predetermined amine compound 2e.

The present production process is a method for preparing a compound 4d in which $L^1$ is —C(O)—N($R^6$)—, among the starting compounds 1 of the production process 1.

(First Step)

The present step is a step of obtaining a compound 4b by the condensation reaction of the compound 4a with the compound 2b prepared by the method described in Tetrahedron Letters, 1993, Vol. 34, No. 21, p. 3389-3392, or a method equivalent thereto.

For the condensation reaction, the method of the first step in the starting material synthesis 1 can be used.

(Second Step)

The present step is a method for preparing a compound 4c by forming an isocyanate compound by the condensation reaction of a predetermined amine compound 2e with triphosgene, and subsequently the condensation of the compound with the compound 4b.

The reaction is carried out by using a predetermined amine compound 2e and triphosgene in equivalent amounts, or either thereof in an excess amount, and stirring a mixture thereof in a solvent which is inert to the reaction, in a range of from cooling to heating and refluxing, and preferably from at −20° C. to at room temperature, usually for 0.1 hours to 5 days, in the presence of a base. Examples of the solvent used herein are not particularly limited, but include halogenated hydrocarbons such as dichloromethane, 1,2-dichloroethane, chloroform and the like. In addition, it is preferable in some cases for the progress of the reaction to use an organic base such as triethylamine, pyridine and the like as a base.

Next, the compound 4b in an equivalent amount or an excess amount is added to the isocyanate compound, and the mixture is stirred in a solvent which is inert to the reaction, in a range of from cooling to heating and refluxing, and preferably at room temperature, usually for 0.1 hours to 5 days, in the presence of a base. Examples of the solvent used herein are not particularly limited, but include halogenated hydrocarbons such as dichloromethane, 1,2-dichloroethane, chloroform and the like. In addition, it is preferable in some cases for the progress of the reaction to use an organic base such as triethylamine, pyridine as a base and the like.

(Third Step)

The present step is a step of obtaining a compound 4d from the compound 4c by deprotecting a benzyl group or a benzyloxymethyl group, in addition to the above step, in a case where $R^8$ is the benzyl group or the benzyloxymethyl group.

For the deprotection, the method of the second step in the starting material synthesis 1 can be used.

(Starting Material Synthesis 4)

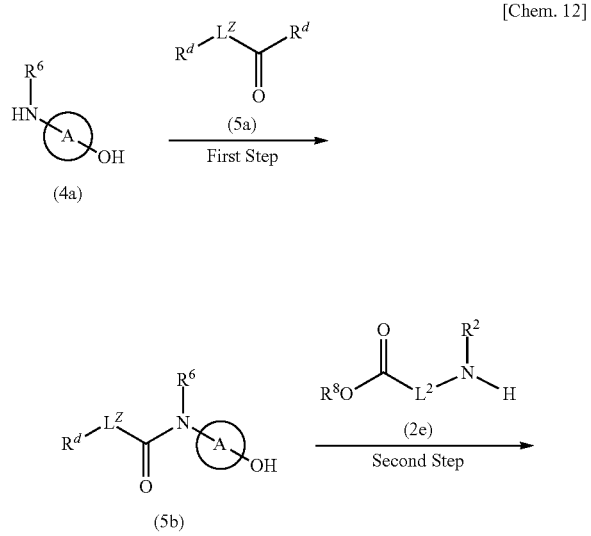

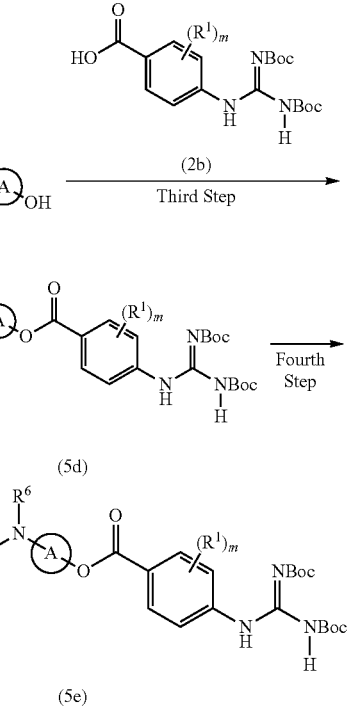

(wherein $R^d$ represents halogen).

The present production process is a method for preparing a compound 5e in which $L^1$ is -lower alkylene-C(O)—N($R^6$)—, among the starting compounds 1 of the production process 1.

(First Step)

The present step is a step of obtaining a compound 5b by the amidation of the compound 4a with a predetermined acyl compound 5a.

The reaction is carried out by using the compound 4a and a predetermined acyl compound 5a in equivalent amounts, or either thereof in an excess amount, and stirring a mixture thereof in a solvent which is inert to the reaction, in a range of from cooling to heating and refluxing, and preferably from at −20° C. to 60° C., usually for 0.1 hours to 5 days, in the presence of a base. Examples of the solvent used herein are not particularly limited, but include halogenated hydrocarbons such as dichloromethane, 1,2-dichloroethane, chloroform and the like. In addition, it is preferable in some cases for the progress of the reaction to use an organic base such as triethylamine, pyridine and the like as a base.

(Second Step)

The present step is a step of obtaining a compound 5c by alkylation of the compound 5b with a predetermined amine compound 2e.

The reaction is carried out by using the compound 5b and a predetermined amine compound 2e in equivalent amounts, or either thereof in an excess amount, and stirring a mixture thereof in a solvent which is inert to the reaction, in a range of from cooling to heating and refluxing, and preferably from at room temperature to 100° C., usually for 0.1 hours to 5 days, in the presence of a base. Examples of the solvent used herein are not particularly limited, but include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran (THF), dioxane, dimethoxyethane and the like, N,N-dimethylformamide (DMF), dimethyl sulfoxide (DMSO), ethyl acetate, acetonitrile, or a mixture thereof. In addition, it is preferable in some cases for the progress of the reaction to use organic bases such as triethylamine, N,N-diisopropylethylamine, N-methylmorpholine, dimethylaminopyridine, pyridine and the like, or inorganic bases such as potassium carbonate, sodium carbonate, potassium hydroxide and the like. Furthermore, it is preferable in some cases for the progress of the reaction to use potassium iodide or the like as an additive.

(Third Step)

The present step is a step of obtaining a compound 5d by the condensation reaction of the compound 5c with the compound 2b prepared by the method described in Tetrahedron Letters, 1993, Vol. 34, No. 21, p. 3389-3392, or a method equivalent thereto.

For the condensation reaction, the method of the first step in the starting material synthesis 1 can be used.

(Fourth step)

The present step is a step of obtaining the compound 5e from the compound 5d by deprotecting a benzyl group or a benzyloxymethyl group, in addition to the above step, in a case where $R^8$ is the benzyl group or the benzyloxymethyl group.

For the deprotection, the method of the second step in the starting material synthesis 1 can be used.

(Starting Material Synthesis 5)

[Chem. 13]

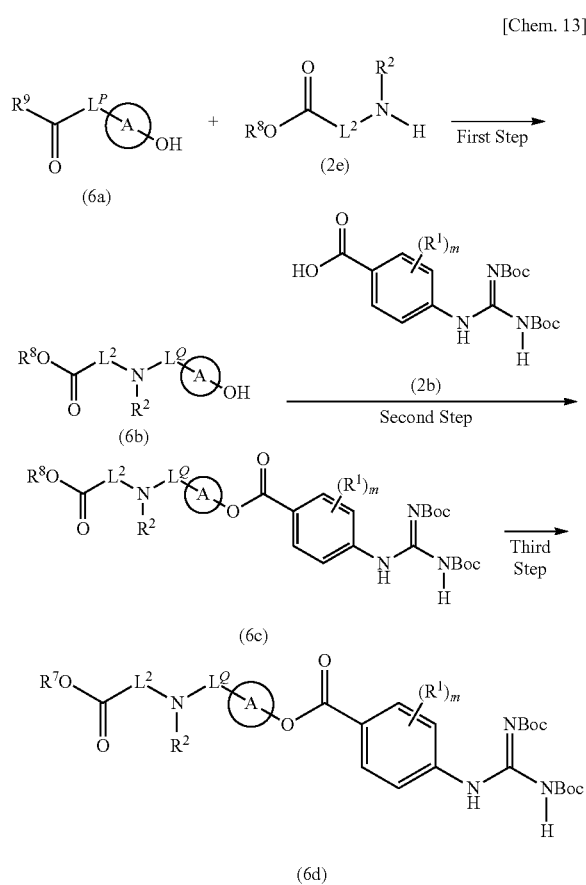

(wherein $R^9$ represents H or lower alkyl, $L^P$ represents a bond, -lower alkylene- or -lower alkylene-NR$^6$—, and $L^Q$ represents -lower alkylene- or -lower alkylene-NR$^6$—).

The present production process is a method for preparing a compound 6d in which $L^1$ is -lower alkylene- or -lower alkylene-NR$^6$—, among the starting compounds 1 of the production process 1.

(First Step)

The present step is a step of obtaining a compound 6b by the reductive amination of the compound 6a with a predetermined amine compound 2e.

The reaction is carried out by using the compound 6a and a predetermined amine compound 2e in equivalent amounts, or either thereof in an excess amount, and stirring a mixture thereof in a solvent which is inert to the reaction, in a range of from at −45° C. to heating and refluxing, and preferably from 0° C. to room temperature, usually for 0.1 hours to 5 days, in the presence of a reducing agent. Examples of the solvent used herein are not particularly limited, but include halogenated hydrocarbons such as dichloromethane, 1,2-dichloroethane, chloroform and the like, alcohols such as methanol, ethanol and the like, ethers such as diethyl ether, tetrahydrofuran, dioxane, dimethoxyethane and the like, and a mixture thereof. Examples of the reducing agent include sodium cyanoborohydride, sodium triacetoxyborohydride, sodium borohydride and the like. It is preferable in some cases to carry out the reaction in the presence of a dehydrating agent such as molecular sieves or an acid such as acetic acid, hydrochloric acid, a titanium (IV) isopropoxide complex and the like. Depending on the reaction, imine may be generated by the condensation of the compound 6a with the compound 2e, and isolated as a stable intermediate in some cases. In such a case, a compound 6b can be obtained by the reduction reaction of the imine intermediate. Further, instead of the treatment with the reducing agent, a reducing catalyst (for example, palladium on carbon, Raney nickel, and the like) can be used in the presence or absence of an acid such as acetic acid, hydrochloric acid and the like in a solvent such as methanol, ethanol, ethyl acetate and the like to carry out the reaction. In this case, it is preferable to carry out the reaction under a hydrogen atmosphere from normal pressure to 50 atm in a range of from cooling to heating.

REFERENCES

"Comprehensive Organic Functional Group Transformations II", A. R. Katritzky and R. J. K. Taylor, Vol. 2, Elsevier Pergamon, 2005

"Courses in Experimental Chemistry (5$^{th}$ Ed.)", edited by The Chemical Society of Japan, Vol. 14 (2005) (Maruzen)

(Second Step)

The present step is a step of obtaining a compound 6c by the condensation reaction of the compound 6b with the compound 2b prepared by the method described in Tetrahedron Letters, 1993, Vol. 34, No. 21, p. 3389-3392, or a method equivalent thereto.

For the condensation reaction, the method of the first step in the starting material synthesis 1 can be used.

(Third Step)

The present step is a step of obtaining a compound 6d from the compound 6c by deprotecting a benzyl group or a benzyloxymethyl group, in addition to the above step, in a case where $R^8$ is the benzyl group or the benzyloxymethyl group.

For the deprotection, the method of the second step in the starting material synthesis 1 can be used.

The compounds of the formula (I) can be isolated and purified as their free compounds, salts, hydrates, solvates, or polymorphic crystalline substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

1. Inhibitory Activity of Trypsin Enzyme in Humans and Mice

In the experiment, human recombinant trypsin (r-h trypsin; manufactured by WAKO, cat. #206-17171) and mouse trypsin (m-trypsin; purified from the mouse small intestine contents by the present Company) were used.

The method to extract the trypsin from the mouse small intestine is shown below.

The small intestine contents and the gastrointestinal tract of 10 mice were suspended in PBS using Polytron and subjected to centrifugation at 15,000×g several times. The supernatant was mixed at 4° C. for 16 hours with a Benzamidine Sepharose 4 Fast Flow Resin (GE Healthcare: #17-5123-10). After washing the resin with PBS, m-trypsin was eluted with a glycine elution buffer (pH 3.0). It was confirmed by Western blot analysis that the purified fraction was recognized as Anti-mouse Trypsin Antibody (Santa Cruz Biotechnology, Inc.: sc-67388)).

The outline of the measurement method is shown below.

The compound was dissolved in dimethyl sulfoxide (DMSO), and diluted to an arbitrary concentration (A). A was 100-fold diluted with a buffer (0.1 M Tris (pH 8.0), 0.15 M NaCl, 10 mM $CaCl_2$, 0.05% Brij38) (B). The r-h trypsin was diluted with a buffer to 0.088 μg/mL, and the m-trypsin was diluted with a buffer to 1/50 (C). The dilution ratio of the m-trypsin (1/50) was set to exhibit the same activity as the 0.088 μg/mL r-h trypsin as determined by kinetic analysis. The substrate solution of a substrate for the enzyme reaction, BZiPAR, (Rhodamine Reference Substrate) was diluted with a buffer to 5 μmol/L (D). B; 5 μL, C; 5 μL, and D; 10 μL were added to a 384-plate, and incubated at room temperature for 30 minutes. The fluorescent signals were detected with Ex/Em=497/520 using Tecan Safire Fluorometer. The compound was reviewed from 2500 nM to its 3-fold value, 0.0075 nM, at 12 concentrations, and the inhibitory rate of each compound was calculated by assuming the inhibition without addition of the compound (DMSO alone) in the presence of an enzyme as 0% inhibition, and assuming the inhibition without addition of the compound in the absence of an enzyme as 100% inhibition. Based on the obtained inhibitory rates, $IC_{50}$ values (nM) were calculated from the non-linear regression. The test was carried out in the same manner, using camostat as a control compound.

The $IC_{50}$ values (nM) of several representative compounds are shown in Table 1. Ex in the table represents the Example No. as denoted below.

TABLE 1

| Ex | r-h Trypsin | Mouse trypsin |
|---|---|---|
| 1 | 0.17 | 0.19 |
| 2 | 0.92 | 0.49 |
| 11 | 0.76 | 0.45 |
| 13 | 0.91 | 0.84 |
| 14 | 0.23 | 0.22 |
| 15 | 0.2 | 0.19 |
| 16 | 0.23 | 0.26 |
| 17 | 0.43 | 0.27 |
| 20 | 0.90 | 0.54 |
| 21 | 0.26 | 0.17 |
| 22 | 0.29 | 0.20 |
| 23 | 0.34 | 0.28 |
| 24 | 0.21 | 0.17 |
| 25 | 0.29 | 0.25 |
| 26 | 0.29 | 0.18 |
| 27 | 0.26 | 0.19 |
| 28 | 0.24 | 0.17 |
| 29 | 0.31 | 0.21 |
| 30 | 0.26 | 0.19 |
| 31 | 0.31 | 0.34 |
| 33 | 0.88 | 0.6 |
| 34 | 0.36 | 0.24 |
| 35 | 0.44 | 0.28 |
| 36 | 0.43 | 0.38 |
| 37 | 0.38 | 0.34 |
| 40 | 0.50 | 0.45 |
| 41 | 0.32 | 0.31 |
| 45 | 0.57 | 0.66 |
| 51 | 0.46 | 0.47 |
| 52 | 0.30 | 0.39 |
| 53 | 0.45 | 0.35 |
| 54 | 0.42 | 0.38 |
| 56 | 0.88 | 0.64 |
| 58 | 0.73 | 0.68 |
| 59 | 0.27 | 0.31 |
| 60 | 0.21 | 0.21 |
| 61 | 0.23 | 0.14 |
| 62 | 0.29 | 0.17 |
| 63 | 0.43 | 0.41 |
| 64 | 0.37 | 0.70 |
| 65 | 0.40 | 0.45 |
| 66 | 0.35 | 0.45 |
| 71 | 0.18 | 0.23 |
| 78 | 0.49 | 0.39 |
| 80 | 0.21 | 0.30 |
| 93 | 0.40 | 0.56 |
| 94 | 0.42 | 0.39 |
| 95 | 0.66 | 0.64 |
| 96 | 0.22 | 0.46 |
| 102 | 0.29 | 0.30 |
| 108 | 0.19 | 0.14 |
| 111 | 0.54 | 0.44 |
| 113 | 0.24 | 0.28 |
| 119 | 8.6 | 7.5 |
| 131 | 0.51 | 0.40 |
| camostat | 4.6 | 1.6 |

Some representative compounds exhibited good trypsin inhibitory actions, as compared to camostat which is the control compound.

2. Increasing Study of Fecal Protein Concentration in Mice

For the experiment, 6-weeks old ICR mice (male) were used, and the experiment was carried out in five per group. After fasting the mice for 15 hours, the control group was forcibly orally administered with a 0.5% methyl cellulose (MC) solution, and the test drug group was forcibly orally administered (5 mg/kg) with a solution or suspension obtained by dissolving or suspending the compound in the 0.5% MC solution. The fasting was stopped immediately thereafter, free feeding (CE-2) started and then the feces were collected from after 3 hours to after 9 hours. All of the obtained feces were dissolved and suspended in 6 mL of distilled water, and centrifuged for 10 minutes at 3000 rpm. The protein concentration in the supernatant was measured by a Bradford method, and the amount of the protein in 1 g of feces was calculated by dividing the protein concentration in the feces by the total weight of feces. Further, the efficacy was investigated from the ratio to the control. For the compounds that were evaluated multiple times, the average values were calculated.

For some representative compounds, the protein increasing activities in feces are shown in Table 2, assuming a value for the control as 1. Ex in the table represents the Example No. as denoted below of the test compound.

TABLE 2

| Ex | fold vs control |
|---|---|
| 13 | 1.85 |
| 15 | 1.67 |
| 16 | 1.70 |
| 36 | 1.92 |
| 41 | 1.77 |
| 45 | 1.65 |
| 52 | 1.82 |
| 53 | 1.79 |
| 56 | 2.02 |
| 58 | 1.79 |
| 59 | 2.17 |
| 60 | 2.27 |
| 61 | 1.67 |
| 63 | 1.84 |
| 64 | 1.98 |
| 78 | 1.67 |
| 80 | 1.89 |
| 95 | 1.88 |
| 96 | 2.02 |
| 102 | 2.31 |
| 108 | 1.85 |
| 111 | 2.01 |
| 113 | 1.93 |
| 119 | 1.39 |

Some representative compounds have shown that the dietary protein is discharged as undigested by the trypsin activity inhibitory action, and thus, the protein uptake in the biological body is suppressed well.

3. Doxorubicin (DXR) Nephropathy Mouse Test (Renal Function Reduction Model) Test For the experiment, BALB/mice (male) were used. At a time when they were 6-weeks old, DXR was injected via the caudal vein to induce nephropathy. The test compound was orally administered once a day immediately after administration of DXR. The amounts to be administered were set to three doses, 3, 10, and 30 mg/kg, and for the control group, a vehicle was administered at the same doses. At 1, 2, 3, and 4 weeks after the start of administration of a drug, urine collection on each was carried out and the amount of protein excreted in urine was measured. Further, after the end of urine collection at week 4, blood sampling was performed, and the amount of creatinine in plasma and the amount of urea nitrogen (BUN) were measured.

As a result of the test above, it was confirmed that certain compounds of the present invention significantly reduced the amount of protein excreted in urine, as compared to the control group. In addition, it was confirmed that an increase in the amount of creatinine in plasma was not recognized, and the amount of BUN was significantly reduced, as compared to the control group.

From the results of the present test, it was confirmed that the compound favorably suppressed the symptoms of reduced renal function, such as increased amount of protein excreted in urine, and suppressed the deterioration of the disease state.

4. Rat Uninephrectomy Doxorubicin (DXR)-Induced Nephropathy Model (Renal Function Reduced Model) Test Uninephrectomy was performed in the right kidney of 10-weeks old Wistar rats (male), and at one week thereafter, DXR (5 mg/kg) was administered via the caudal vein to prepare a model. A test compound was suspended in 0.5% methylcellulose (MC) immediately after the preparation of the model, and was forcibly orally administered twice daily at each of doses of 3, 10, and 30 mg/kg. 0.5% MC was forcibly orally administered to each of a sham group and a control group. At 1, 2, 3, and 4 weeks after the start of administration of a test drug, 24-hour urine collection was performed, and the amount of the excreted protein in urine was measured. Blood sampling was performed after the end of the urine collection at week 4, the concentration of creatinine in plasma was measured, and the effect on the renal function was also confirmed.

As a result of the test above, certain compounds of the present invention significantly suppressed the amount of protein excreted in urine in a dose-dependent manner, as compared with the control group, and suppressed by about 45% at a maximal degree. Further, the present compound significantly suppressed the increase of creatinine in plasma in a dose-dependent manner, and suppressed by about 70% at a maximal degree.

From the results of the present test, it was confirmed that the compounds suppressed the increase in the amount of protein excreted study in urine, and suppressed the increase of creatinine in plasma, and thus, the progression of the disease state was suppressed.

As seen in the test above, it was confirmed that some representative compounds of the present invention have a good inhibitory activity of trypsin and an inhibitory effects for protein absorption by an amount of protein for suppression discharged into the feces, an effects of lowering the protein excretion in urine in a model with renal function suppression, an action of lowering the amount of BUN, and an effects of inhibiting the increase in creatinine in plasma. Therefore, the compounds of the formula (I) can be used as an agent for preventing and/or treating trypsin-related diseases as well as an agent for preventing and/or treating renal diseases, specifically, chronic kidney disease, diabetic nephropathy, chronic nephritis, nephrosis, gout kidney, and the like as an agent which will substitute low protein diet.

A pharmaceutical composition containing one or two or more kinds of the compound of the formula (I) or a salt thereof as an active ingredient can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, inhalers, and the like.

The solid composition for use in the oral administration is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing assisting agent. These are sterilized, for example, by filtration through a bacteria retaining filter, by a bactericide being blended in, or irradiation. In addition, these can also be used by preparing a sterile solid composition, and dissolving or suspending in sterile water or a sterile solvent for injection prior to its use.

The agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like.

In oral administration, the daily dose is appropriately from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing the diseases for which the compound of the formula (I) is considered to be effective, as described above. The combined preparation may be administered simultaneously, or separately and continuously, or at a desired time interval. The preparations to be administered simultaneously may be a blend, or may be prepared individually.

EXAMPLES

Hereinbelow, the preparation methods for the compound of the formula (I) or a salt thereof will be described in more detail with reference to Examples, but the present invention is not limited to the compounds described in the Examples as described below. Furthermore, the production processes for the starting compounds will be described in Preparation Examples. Further, the preparation methods for the compound of the formula (I) are not limited to the preparation methods of the specific Examples as below, but the compound of the formula (I) can be prepared by any combination of the preparation methods or the methods that are apparent to a person skilled in the art.

Furthermore, the following abbreviations may be used in some cases in the Examples, Preparation Examples, and Tables below.

PEx: Preparation Example No. (the compounds in which "*" is attached in the tables denotes that the compounds are optically active forms), Ex: Example No. (also, the compounds in which "*" is attached in the tables denote that the compounds are optically active forms), PSyn: Preparation Example No. prepared by the same method, Syn: Example No. prepared by the same method, No: Compound No., Str: Structural formula, (Me: methyl, $^i$Pr: isopropyl, $^i$Bu: isobutyl, $^t$Bu: tert-butyl, Ph: phenyl, Boc: tert-butoxycarbonyl, Bn: benzyl, TBS: tert-butyldimethylsilyl), Data: Physicochemical Data, ESI+: m/z values in mass spectroscopy (Ionization ESI, representing $(M+H)^+$ unless otherwise specified), ESI−: ink values in mass spectroscopy (Ionization ESI, representing $(M-H)^-$ unless otherwise specified), APCI+: m/z values (atmospheric pressure chemical ionization APCI, representing $(M+H)^+$ unless otherwise specified), APCI−: m/z values (atmospheric pressure chemical ionization APCI, representing $(M-H)^-$ unless otherwise specified), APCI/ESI+: APCI/ESI-MS$[M+H]^+$ (APCI/ESI means the simultaneous measurement of APCI and ESI), APCI/ESI−: APCI/ESI-MS$[M-H]^-$ (APCI/ESI means the simultaneous measurement of APCI and ESI), EI: EI$[M]^+$, CI: CI$[M]^+$, NMR1: δ (ppm) in 1H NMR in DMSO-d$_6$, NMR2: δ (ppm) in 1H NMR in CDCl$_3$, mp: melting point (° C.), in which the melting point was measured by a method described for thermal analysis measurement. "M" in Preparation Examples and Examples: mol/L, RT: showing a retention time in supercritical chromatography or liquid chromatography, in a unit of minutes (min).

Further, in the structural formulae, HCl represents hydrochloride, TFA represents trifluoroacetate, MsOH represents mesylate, and the numeral before HCl represents a molar ratio. For example, 2HCl means dihydrochloride.

In the structural formula, a compound having double bonds crossing (for example, PEx. 107) represents a mixture of an E-isomer and a Z-isomer.

Test Example

Thermal Analysis Measurement (Differential Scanning calorimetry (DSC Analysis)) The DSC analysis was carried out using Q2000 and Q1000, each manufactured by TA Instruments. Approximately 2 mg of a sample was charged in an exclusively-used aluminum-made sample pan, and the change in heat amount generated between the sample and a reference (an empty aluminum-made sample pan), with a measurement range from room temperature to 300° C. under a nitrogen atmosphere (50 mL/min) and a temperature elevating rate of 10° C./min was continuously measured and recorded. Furthermore, the devices including data processing were handled in accordance to the methods and procedures as instructed for each device.

In addition, the term "around" as used in the values of the endothermic onset temperature in DSC largely means the values of the temperature of the endothermic onset (extrapolation initiation), and preferably means that the values be not more or less than the values by 2° C. (±2° C.), and more preferably means that the values be not more or less than the values by 1° C. (±1° C.).

Preparation Example 1

To a solution of 4-(4-hydroxyphenyl)butanoic acid (2.00 g) in N,N-dimethylformamide (28.0 mL) were added potassium carbonate (1.61 g) and benzyl bromide (1.46 mL), followed by stirring at room temperature overnight. The reaction suspension was concentrated under reduced pressure, and then to the residue was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain benzyl 4-(4-hydroxyphenyl)butanoate (2.64 g).

Preparation Example 2

To a solution of 4-[N',N"-bis(tert-butoxycarbonyl)carbamimidamido]benzoic acid (2.96 g) in dichloromethane (20.0 mL) were added 1-[3-(dimethylamino)propyl]-3-ethylcarbodiimide hydrochloride (1.80 g), benzyl 4-(4-hydroxyphenyl) butanoate (2.00 g), and N,N-dimethyl-4-aminopyridine (286 mg), followed by stirring at room temperature overnight. To a reaction solution was added 1 M hydrochloric acid, followed by concentrating under reduced pressure. The residue was purified by silica gel column chromatography (hexane-ethyl acetate) to obtain 4-[4-(benzyloxy)-4-oxobutyl]phenyl 4-[N',N"-bis(tert-butoxycarbonyl)carbamimidamido]benzoate (3.98 g).

Preparation Example 3

To a solution of 4-[4-(benzyloxy)-4-oxobutyl]phenyl 4-[N',N"-bis(tert-butoxycarbonyl)carbamimidamido]benzoate (3.98 g) in tetrahydrofuran (40.0 mL) was added 10% palladium-carbon (398 mg), followed by stirring at room temperature for 3 hours under a hydrogen pressure of 3 atm. The reaction suspension was filtered through Celite, and then the filtrate was concentrated under reduced pressure to obtain 4-[4-({4-[N',N"-bis(tert-butoxycarbonyl)carbamimidamido]benzoyl}oxy)phenyl]butanoic acid (3.30 g).

Preparation Example 4

To a solution of 4-[4-({4-[N',N"-bis(tert-butoxycarbonyl) carbamimidamido]benzoyl}oxy)phenyl]butanoic acid (250 mg) in N,N-dimethylformamide (5.00 mL) were added tert-butyl O-tert-butyl-L-tyrosinate hydrochloride (152 mg), 1-[3-(dimethylamino)propyl]-3-ethylcarbodiimide hydrochloride (88.5 mg), 1H-benzotriazol-1-ol (62.4 mg), and triethylamine (0.0643 mL), followed by stirring at room temperature overnight. To a reaction solution was added water, followed by extraction with ethyl acetate. The organic layer was washed with water and a saturated aqueous sodium chloride solution in this order, then dried over anhydrous sodium sulfate, and concentrated under reduced pressure. The residue was purified by silica gel column chromatography (hexane-ethyl acetate) to obtain tert-butyl N-{4-[4-({4-[N',N"-bis(tert-butoxycarbonyl)carbamimidamido]benzoyl}oxy)phenyl]butanoyl}-O-tert-butyl-L-tyrosinate (327 mg).

Preparation Example 5

To a solution of benzyl (2-bromo-4-hydroxyphenyl)acetate (400 mg) in dimethoxyethane (4.00 mL) and water (1.20 mL) were added phenyl boronic acid (182 mg), sodium carbonate (396 mg), and 1,1'-bis(diphenylphosphino) ferrocene palladium (II) dichloride dichloromethane complex (50.9 mg), followed by stirring at 80° C. overnight. To the reaction mixture was added water, followed by extraction with ethyl acetate. The organic layer was washed with water and a saturated aqueous sodium chloride solution in this order, then dried over anhydrous sodium sulfate, and concentrated under reduced pressure. The residue was purified by silica gel column chromatography (hexane-ethyl acetate) to obtain benzyl (5-hydroxybiphenyl-2-yl)acetate (344 mg).

Preparation Example 6

To a solution of 4-methoxy-2-(trifluoromethyl)phenylacetic acid (500 mg) in acetic acid (5.00 mL) was added a 48% aqueous hydrobromic acid solution (5.00 mL), followed by stirring at 145° C. overnight. The reaction suspension was concentrated under reduced pressure, to the residue was then added water, and the resulting solid was collected by filtration to obtain 4-hydroxy-2-(trifluoromethyl)phenylacetic acid (300 mg).

Preparation Example 7

To a solution of benzyl (2-bromo-4-hydroxyphenyl)acetate (2.00 g) in dichloromethane (30.0 mL) were added tert-butyl(chloro)dimethylsilane (1.13 g) and N,N-dimethyl-4-aminopyridine (913 mg) under ice-cooling, followed by stirring for 2 hours under ice-cooling. The reaction mixture was diluted with water, followed by extraction with ethyl acetate. The organic layer was dried over anhydrous sodium sulfate and concentrated under reduced pressure. The residue was purified by silica gel column chromatography (hexane-ethyl acetate) to obtain benzyl (2-bromo-4-{[tert-butyl(dimethyl)silyl]oxy}phenyl)acetate (2.63 g).

Preparation Example 8

To a solution of benzyl (2-bromo-4-{[tert-butyl(dimethyl) silyl]oxy}phenyl)acetate (250 mg) in toluene (5.00 mL) were added water (0.250 mL), potassium phosphate (366 mg), tricyclohexylphosphine (64.4 mg), palladium (II) acetate (25.8 mg), and cyclopropylboronic acid (98.6 mg), followed by stirring at 110° C. overnight. To the reaction mixture was added water, followed by extraction with ethyl acetate. The organic layer was washed with water and a saturated aqueous sodium chloride solution in this order, then dried over anhydrous sodium sulfate, and concentrated under reduced pressure. The residue was purified by silica gel column chromatography (hexane-ethyl acetate) to obtain benzyl (4-{[tert-butyl(dimethyl)silyl]oxy}-2-cyclopropylphenyl)acetate (210 mg).

Preparation Example 9

To a solution of benzyl (4-{[tert-butyl(dimethyl)silyl] oxy}-2-cyclopropylphenyl)acetate (586 mg) in tetrahydrofuran (6.89 mL) was added a 1 M solution of tetra-n-butylammonium fluoride in tetrahydrofuran (2.23 mL) under ice-cooling, followed by stirring at room temperature overnight. To a reaction solution was added water, followed by extraction with ethyl acetate. The organic layer was washed with water and a saturated aqueous sodium chloride solution in this order, then dried over anhydrous sodium sulfate, and concentrated under reduced pressure. The residue was purified by silica gel column chromatography (hexane-ethyl acetate) to obtain benzyl (2-cyclopropyl-4-hydroxyphenyl)acetate (398 mg).

Preparation Example 10

To a solution of 4-[2-(benzyloxy)-2-oxoethyl]-2-chlorophenyl 4-[N',N''-bis(tert-butoxycarbonyl)carbamimidamido]benzoate (1.98 g) in tetrahydrofuran (27.1 mL) was added 10% palladium-carbon (196 mg), followed by stirring at room temperature for 1 hour at normal pressure under a hydrogen atmosphere. The reaction suspension was filtered through Celite, and then the filtrate was concentrated under reduced pressure to obtain [4-({4-[N',N''-bis(tert-butoxycarbonyl)carbamimidamido]benzoyl}oxy)-3-chlorophenyl] acetic acid (1.78 g).

Preparation Example 11

To a mixture of 1,3-dichloro-5-methoxybenzene (10.0 g), paraformaldehyde (2.21 g), and concentrated hydrochloric acid (100 mL) was added concentrated sulfuric acid (1.00 mL) at room temperature. After heating and refluxing at 100° C. for 8 hours, and leaving to be cooled to room temperature, water was added thereto, followed by extraction with ethyl acetate. The organic layer was washed with water, a saturated aqueous sodium hydrogen carbonate solution, and a saturated aqueous sodium chloride solution, then dried over anhydrous magnesium sulfate, and concentrated under reduced pressure. To the residue were added dioxane (56.0 mL) and a 1 M aqueous sodium hydroxide solution (113 mL), followed by heating and refluxing at 100° C. for 3 hours. The reaction solution was left to be cooled, and then water was added thereto, followed by extraction with chloroform. The organic layer was washed with a saturated aqueous sodium chloride solution, dried over anhydrous magnesium sulfate, and then concentrated under reduced pressure. The residue was purified by silica gel column chromatography (hexane-ethyl acetate) to obtain (2,6-dichloro-4-methoxyphenyl)methanol (4.67 g).

Preparation Example 12

To a solution of (2,6-dichloro-4-methoxyphenyl)methanol (4.66 g) in tetrahydrofuran (50.0 mL) was added phosphorus tribromide (0.846 mL) under ice-cooling, followed by stirring for 1 hour under ice-cooling. To the reaction suspension was added a saturated aqueous sodium hydrogen carbonate solution, followed by extraction with ethyl acetate. The organic layer was washed with water and a saturated aqueous sodium chloride solution, and then dried over anhydrous sodium sulfate. The solvent was concentrated under reduced pressure to obtain 2-(bromomethyl)-1,3-dichloro-5-methoxybenzene (5.45 g).

Preparation Example 13

To a solution of 1,2-dichloro-3-methoxybenzene (5.00 g) in acetic acid (14.0 mL) were added paraformaldehyde (1.00 g) and a 25% solution of hydrobromic acid in acetic acid (8.00 mL), followed by stirring at 90° C. for 5 hours. The reaction mixture was left to be cooled to room temperature, ice water was added to the mixture, and the resulting solid was collected by filtration. The obtained solid was recrystallized from hexane to obtain 1-(bromomethyl)-2,3-dichloro-4-methoxybenzene (3.90 g).

Preparation Example 14

To a mixture of 1-(bromomethyl)-2,3-dichloro-4-methoxybenzene (1.00 g), water (3.00 mL), methanol (6.00 mL), and dimethyl sulfoxide (2.00 mL) was added sodium cyanide (246 mg) at room temperature, followed by stirring at 40° C. for 5 hours. The reaction mixture was concentrated under reduced pressure, and then water was added thereto. The resulting solid was collected by filtration to obtain (2,3-dichloro-4-methoxyphenyl)acetonitrile (776 mg).

Preparation Example 15

(2,3-Dichloro-4-methoxyphenyl)acetonitrile (770 mg) was dissolved in a 50% aqueous acetic acid solution (8.00 mL), and then concentrated sulfuric acid (4.00 mL) was added thereto, followed by stirring at 110° C. overnight. The reaction mixture was cooled to room temperature, then ice water was added to the mixture, and the resulting solid was collected by filtration and washed with water to obtain (2,3-dichloro-4-methoxyphenyl)acetic acid (737 mg).

Preparation Example 16

To a solution of N-[(benzyloxy)carbonyl]-4-(tert-butoxycarbonyl)-L-phenylalanine (500 mg) in tetrahydrofuran (4.00 mL) and tert-butyl alcohol (4.00 mL) were added di-tert-butyl dicarbonate (656 mg) and N,N-dimethyl-4-aminopyridine (30.6 mg), followed by stirring at room temperature overnight. To a reaction solution was added water, followed by extraction with ethyl acetate. The organic layer was washed with water, a saturated aqueous sodium hydrogen carbonate solution, and a saturated aqueous sodium chloride solution in this order, then dried over anhydrous sodium sulfate, and concentrated under reduced pressure to obtain tert-butyl N-[(benzyloxy)carbonyl]-4-(tert-butoxycarbonyl)-L-phenylalaninate (641 mg).

Preparation Example 17

To a solution of tert-butyl N-[(benzyloxy)carbonyl]-4-(tert-butoxycarbonyl)-L-phenylalaninate (570 mg) in ethanol (3.00 mL) and tetrahydrofuran (3.00 mL) was added 10% palladium-carbon (138 mg) under an argon atmosphere, and then followed by stirring at room temperature overnight under a hydrogen atmosphere. The reaction suspension was filtered through Celite, and the filtrate was concentrated under reduced pressure to obtain tert-butyl 4-(tert-butoxycarbonyl)-L-phenylalaninate (431 mg).

Preparation Example 18

Under an argon atmosphere, to a suspension of 4-(2-{[(benzyloxy)carbonyl]amino}ethyl)benzoic acid (469 mg)

in toluene (10.0 mL) was added 1,1-di-tert-butoxy-N,N-dimethylmethaneamine (1.50 mL) at 80° C., followed by stirring at 80° C. for 30 minutes. After cooling to room temperature, the reaction solution was concentrated under reduced pressure. The residue was purified by silica gel column chromatography (hexane-ethyl acetate) to obtain tert-butyl 4-(2-{[(benzyloxy)carbonyl]amino}ethyl)benzoate (439 mg).

Preparation Example 19

To a solution of tert-butyl 4-(2-{[(benzyloxy)carbonyl]amino}ethyl)benzoate (515 mg) in N,N-dimethylformamide (10.0 mL) was added 55% sodium hydride (65.0 mg) under ice-cooling, followed by stirring for 30 minutes under ice-cooling. Under ice-cooling, tert-butyl bromoacetate (0.300 mL) was added thereto, followed by stirring at room temperature overnight. To the reaction mixture was added a saturated aqueous ammonium chloride solution under ice-cooling, followed by extraction with ethyl acetate. The organic layer was washed with water and then dried over anhydrous magnesium sulfate. The solvent was concentrated under reduced pressure, and then the residue was purified by silica gel column chromatography (hexane-ethyl acetate) to obtain tert-butyl 4-(2-{[(benzyloxy)carbonyl](2-tert-butoxy-2-oxoethyl)amino}ethyl)benzoate (473 mg).

Preparation Example 20

To a solution of benzyl (2-bromo-4-hydroxyphenyl)acetate (500 mg) in N,N-dimethylformamide (12.5 mL) was added cuprous chloride (1.62 g), followed by stirring at 140° C. overnight. The reaction mixture was left to be cooled, and then ice water and 1 M hydrochloric acid was added thereto, followed by stirring. After extraction with ethyl acetate, the organic layer was washed with water, a saturated aqueous sodium hydrogen carbonate solution, and a saturated aqueous sodium chloride solution, dried over anhydrous sodium sulfate, and concentrated under reduced pressure. Then, the residue was purified by silica gel column chromatography (hexane-ethyl acetate) to obtain benzyl (2-chloro-4-hydroxyphenyl)acetate (381 mg).

Preparation Example 21

To benzyl N-(tert-butoxycarbonyl)-3-fluoro-L-phenylalaninate (659 mg) was added a 4 M solution of hydrogen chloride in dioxane (8.82 mL), followed by stirring at room temperature overnight. The reaction mixture was concentrated under reduced pressure to obtain benzyl 3-fluoro-L-phenylalaninate hydrochloride (505 mg).

Preparation Example 22

To a solution of benzyl N-{[4-({4-[N',N''-bis(tert-butoxycarbonyl)carbamimidamido]benzoyl}oxy)-2-chlorophenyl]acetyl}-3-fluoro-L-phenylalaninate (260 mg) in tetrahydrofuran (4.00 mL) was added one drop of 1 M hydrochloric acid, and 10% palladium-carbon (20.5 mg) was added under an argon atmosphere, followed by stirring at room temperature for 1 hour at normal pressure under a hydrogen atmosphere. The reaction mixture was filtered through Celite, and the filtrate was concentrated under reduced pressure to obtain N-{[4-({4-[N',N''-bis(tert-butoxycarbonyl)carbamimidamido]benzoyl}oxy)-2-chlorophenyl]acetyl}-3-fluoro-L-phenylalanine (187 mg).

Preparation Example 23

To a solution of tert-butyl L-phenylalaninate hydrochloride (800 mg) in dimethyl sulfoxide (3.20 mL) were added potassium carbonate (429 mg) and tert-butyl acrylate (0.901 mL), followed by stirring at 150° C. for 1 hour under microwave. After cooling to room temperature, water was added thereto, followed by extraction with ethyl acetate. The organic layer was dried over anhydrous sodium sulfate and then concentrated under reduced pressure. The residue was purified by silica gel column chromatography (hexane-ethyl acetate) to obtain tert-butyl N-(3-tert-butoxy-3-oxopropyl)-L-phenylalaninate (266 mg).

Preparation Example 24

To a solution of tert-butyl L-phenylalaninate hydrochloride (456 mg) in acetonitrile (8.00 mL) were added potassium carbonate (510 mg) and tert-butyl 3-(bromomethyl)benzoate (400 mg), followed by stirring at room temperature overnight. To the reaction suspension was added water, followed by extraction with ethyl acetate. The organic layer was dried over anhydrous sodium sulfate and concentrated under reduced pressure. The residue was purified by silica gel column chromatography (hexane-ethyl acetate) to obtain tert-butyl N-[3-(tert-butoxycarbonyl)benzyl]-L-phenylalaninate (340 mg).

Preparation Example 25

To a solution of tert-butyl 3-(2-aminoethyl)benzoate (900 mg) in N,N-dimethylformamide (20.0 mL) were added potassium carbonate (600 mg) and tert-butyl bromoacetate (0.600 mL) under ice-cooling, followed by stirring at room temperature for 5 hours. To the reaction suspension was added water, followed by extraction with ethyl acetate. The organic layer was washed with water, dried over anhydrous magnesium sulfate, and concentrated under reduced pressure. The residue was purified by silica gel column chromatography (hexane-ethyl acetate) to obtain tert-butyl 3-{2-[(2-tert-butoxy-2-oxoethyl)amino]ethyl}benzoate (738 mg).

Preparation Example 26

To a solution of [4-({4-[N',N''-bis(tert-butoxycarbonyl)carbamimidamido]benzoyl}oxy)-2-chlorophenyl]acetic acid (300 mg) in N,N-dimethylformamide (4.00 mL) were added O-(7-azabenzotriazole-1-yl)-N,N,N',N'-tetramethyluronium hexafluorophosphate (207 mg), diisopropylethylamine (0.0950 mL), and tert-butyl N-(2-phenylethyl)glycinate (128 mg) under ice-cooling, followed by stirring at room temperature for 5 hours. To the reaction mixture was added water, followed by extraction with ethyl acetate. The organic layer was washed with water, dried over anhydrous magnesium sulfate, and concentrated under reduced pressure. The residue was purified by silica gel column chromatography (hexane-ethyl acetate) to obtain 4-{2-[(2-tert-butoxy-2-oxoethyl)(2-phenylethyl)amino]-2-oxoethyl}-3-chlorophenyl 4-[N',N''-bis(tert-butoxycarbonyl)carbamimidamido]benzoate (267 mg).

Preparation Example 27

N,N-Dimethylformamide (10.0 mL) was bubbled with argon, and then 4-bromo-3-chlorophenol (1.00 g), benzyl acrylate (1.00 mL), bis(dibenzylideneacetone)palladium (0) (85.0 mg), tris(2-methylphenyl)phosphine (150 mg), and triethylamine (0.700 mL) were added thereto, followed by stirring at 100° C. overnight under an argon atmosphere. The reaction suspension was air-cooled to room temperature, and then water was added thereto, followed by extraction with ethyl acetate. The organic layer was washed with a saturated aqueous sodium chloride solution, dried over anhydrous magnesium sulfate, and then concentrated under reduced pressure. The residue was purified by silica gel column chromatography (hexane-ethyl acetate) to obtain benzyl (2E)-3-(2-chloro-4-hydroxyphenyl)acrylate (1.25 g).

Preparation Example 28

To a solution of tert-butyl 3-(chloromethyl)benzoate (25.3 g) in N,N-dimethylformamide (250 mL) were added tert-butyl glycinate hydrochloride (37.4 g) and potassium carbonate (61.7 g), followed by stirring at 60° C. overnight. To the reaction suspension was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 3-{[(2-tert-butoxy-2-oxoethyl)amino]methyl}benzoate (23.0 g).

Preparation Example 29

To a solution of tert-butyl N-(3-nitrobenzyl)glycinate (3.39 g) in dichloromethane (20.0 mL) was added triethylamine (7.99 mL). Under ice-cooling, a solution of trifluoroacetic anhydride (2.70 mL) in dichloromethane (13.0 mL) was added thereto, followed by stirring at room temperature for 4 hours. Under ice-cooling, the mixture was diluted with water, followed by extraction with chloroform. The organic layer was washed with water and a saturated aqueous sodium chloride solution, dried over anhydrous magnesium sulfate, and then concentrated under reduced pressure. The residue was purified by silica gel column chromatography (hexane-ethyl acetate) to obtain tert-butyl N-(3-nitrobenzyl)-N-(trifluoroacetyl)glycinate (4.30 g).

Preparation Example 30

To a mixture of tert-butyl N-(3-nitrobenzyl)-N-(trifluoroacetyl)glycinate (4.30 g), iron (13.2 g), water (41.8 mL), and ethanol (83.5 mL) was added ammonium chloride (2.54 g) at room temperature, followed by heating and refluxing at 100° C. for 1 hour. After leaving to be cooled, the reaction suspension was filtered through Celite and the filtrate was concentrated under reduced pressure. To the residue was added water, followed by extraction with ethyl acetate. The organic layer was dried over anhydrous magnesium sulfate and then concentrated under reduced pressure to obtain tert-butyl N-(3-aminobenzyl)-N-(trifluoroacetyl)glycinate (3.76 g).

Preparation Example 31

To a solution of tert-butyl N-(3-aminobenzyl)-N-(trifluoroacetyl)glycinate (1.95 g) and triethylamine (0.981 mL) in dichloromethane (19.5 mL) was added a solution of tert-butyl (chlorosulfonyl)carbamate (1.52 g) in dichloromethane (10.0 mL) under ice-cooling, followed by stirring at room temperature for 3 hours. To the reaction mixture was added water, followed by extraction with ethyl acetate. The organic layer was washed with a saturated aqueous sodium hydrogen carbonate solution and a saturated aqueous sodium chloride solution, then dried over anhydrous magnesium sulfate, and concentrated under reduced pressure. To the residue was added ethyl acetate, and n-hexane was added thereto. The precipitated solid was collected by filtration to obtain tert-butyl N-(3-{[(tert-butoxycarbonyl)sulfamoyl]amino}benzyl)-N-(trifluoroacetyl)glycinate (2.19 g).

Preparation Example 32

To tert-butyl N-(3-{[(tert-butoxycarbonyl)sulfamoyl]amino}benzyl)-N-(trifluoroacetyl)glycinate (2.19 g) were added a 50% aqueous methanol solution (43.9 mL) and potassium carbonate (1.19 g), followed by stirring at room temperature for 5 hours. The reaction mixture was concentrated under reduced pressure, and then the residue was dissolved in water, followed by neutralization with 1 M hydrochloric acid. The mixture was extracted with a mixed solvent of n-butanol and ethyl acetate, dried over anhydrous magnesium sulfate, and concentrated under reduced pressure. The residue was purified by silica gel column chromatography (methanol-chloroform) to obtain tert-butyl N-(3-{[(tert-butoxycarbonyl)sulfamoyl]amino}benzyl)glycinate (1.38 g).

Preparation Example 33 tert-Butyl N-(3-cyanobenzyl)-N-(trifluoroacetyl)glycinate (1.15 g) and hydroxylamine hydrochloride (703 mg) were suspended in ethanol (23.1 mL), and triethylamine (1.41 mL) was added thereto at room temperature, followed by stirring at 65° C. for 6 hours. The reaction suspension was concentrated under reduced pressure, and then to the residue was added water, followed by extraction with ethyl acetate. The organic layer was dried over anhydrous magnesium sulfate, and then concentrated under reduced pressure. The residue was purified by silica gel column chromatography (hexane-ethyl acetate) to obtain tert-butyl N-[3-(N'-hydroxycarbamimidoyl)benzyl]-Nrifluoroacetyl)glycinate (853 mg).

Preparation Example 34

To a solution of tert-butyl N-[3-(N'-hydroxycarbamimidoyl)benzyl]-Nrifluoroacetyl)glycinate (853 mg) in 1,4-dioxane (17.1 mL) was added 1,1'-carbonyldiimidazole (479 mg), followed by stirring at 100° C. for 2 hours. The reaction mixture was left to be cooled, and then concentrated under reduced pressure. To the residue was added water, followed by extraction with ethyl acetate. The organic layer was washed with water and a saturated aqueous sodium chloride solution, then dried over anhydrous magnesium sulfate, and concentrated under reduced pressure to obtain tert-butyl N-[3-(5-oxo-4,5-dihydro-1,2,4-oxadiazol-3-yl)benzyl]-Nrifluoroacetyl)glycinate (1.01 g).

Preparation Example 35

To a solution of ethyl 6-formylpyridine-2-carboxylate (1.74 g) in dichloroethane (30.0 mL) were added tert-butyl glycinate hydrochloride (4.89 g), triethylamine (4.06 mL), and acetic acid (2.78 mL), and sodium triacetoxyborohydride (6.18 g) under ice-cooling. The reaction suspension was stirred at room temperature overnight. To the reaction mixture was added a saturated aqueous sodium hydrogen carbonate solution, and then sodium hydrogen carbonate was added thereto until the solution became basic. The reaction mixture was extracted with chloroform, and the organic layer was dried over anhydrous sodium sulfate and concentrated under reduced pressure. The residue was purified by basic silica gel column chromatography (hexane-ethyl acetate) to obtain ethyl 6-{[(2-tert-butoxy-2-oxoethyl)amino] methyl}pyridine-2-carboxylate (2.83 g).

Preparation Example 36

To a solution of ethyl 6-{[(2-tert-butoxy-2-oxoethyl) amino]methyl}pyridine-2-carboxylate (2.81 g) in tetrahydrofuran (30.0 mL) were added water (30.0 mL) and sodium hydrogen carbonate (962 mg), and then benzyl chloroformate (1.47 mL) was added thereto under ice-cooling. The reaction suspension was stirred at room temperature overnight and extracted with ethyl acetate, and the organic layer was washed with a saturated aqueous sodium chloride solution, then dried over anhydrous sodium sulfate, and concentrated under reduced pressure. The residue was purified by silica gel column chromatography (hexane-ethyl acetate) to obtain ethyl 6-({[(benzyloxy)carbonyl](2-tert-butoxy-2-oxoethyl) amino}methyl)pyridine-2-carboxylate (3.27 g).

Preparation Example 37

To a solution of ethyl 6-({[(benzyloxy)carbonyl](2-tert-butoxy-2-oxoethyl)amino}methyl)pyridine-2-carboxylate (3.26 g) in tetrahydrofuran (10.0 mL) were added a 1 M aqueous sodium hydroxide solution (8.00 mL), followed by stirring at room temperature overnight. To the reaction mixture was added 1 M hydrochloric acid (8.00 mL), followed by extraction with chloroform. The organic layer was dried over anhydrous sodium sulfate and then concentrated under reduced pressure. The residue was purified by silica gel column chromatography (hexane-ethyl acetate) to obtain 6-({[(benzyloxy)carbonyl](2-tert-butoxy-2-oxoethyl) amino}methyl)pyridine-2-carboxylic acid (2.08 g).

Preparation Example 38

To a mixture of tert-butyl 2-methylquinoline-4-carboxylate (4.61 g) and carbon tetrachloride (50.0 mL) were added N-bromosuccinimide (3.71 g) and azobisisobutyronitrile (156 mg), followed by stirring at 90° C. for 5 hours. The reaction suspension was filtered, and the filtrate was concentrated under reduced pressure. The residue was purified by silica gel column chromatography (hexane-ethyl acetate) to obtain tert-butyl 2-(bromomethyl)quinoline-4-carboxylate (2.62 g).

Preparation Example 39

To a mixed solution of tert-butyl 3-cyano-5-fluorobenzoate (3.00 g) in tetrahydrofuran (60.0 mL)-methanol (30.0 mL) was added a mixture of cobalt (II) chloride (4.40 g) and water (60.0 mL) under ice-cooling, and then sodium borohydride (1.54 g) was added under an argon flow, followed by stirring at room temperature for 30 minutes. The insoluble material was filtered through Celite and then washed with a mixed solvent of tetrahydrofuran-methanol-water (2:1:2, and then the filtrate was concentrated under reduced pressure. To the residue was added a saturated aqueous sodium chloride solution, followed by extraction with chloroform. The organic layer was dried over magnesium sulfate and then concentrated under reduced pressure. The residue was purified by basic silica gel column chromatography (chloroform-methanol) to obtain tert-butyl 3-(aminomethyl)-5-fluorobenzoate (1.46 g).

Preparation Example 40

To a solution of tert-butyl 3-(chloromethyl)benzoate (500 mg) in N,N-dimethylformamide (10.0 mL) were added tert-butyl 4-aminobenzoate (426 mg), potassium carbonate (610 mg), and potassium iodide (36.6 mg), followed by stirring at 60° C. overnight. To the reaction suspension was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 3-({[4-(tert-butoxycarbonyl)phenyl]amino}methyl)benzoate (671 mg).

Preparation Example 41

To a solution of 3-[4-({4-[N',N"-bis(tert-butoxycarbonyl) carbamimidamido]benzoyl}oxy)-2-chlorophenyl]propanoic acid (200 mg) in dichloromethane (3.00 mL) was added 1-chloro-N,N,2-trimethylprop-1-en-1-amine (0.0700 mL) under ice-cooling, followed by stirring at room temperature for 1 hour. Under ice-cooling, a solution of tert-butyl N-[3-(2-tert-butoxy-2-oxoethyl)phenyl]glycinate (170 mg) and pyridine (0.0500 mL) in dichloromethane (3.00 mL) was added thereto, followed by stirring at room temperature overnight. To the reaction mixture was added water, followed by extraction with chloroform. The organic layer was dried over anhydrous magnesium sulfate and concentrated under reduced pressure. The residue was purified by silica gel column chromatography (hexane-ethyl acetate) to obtain 4-(3-{(2-tert-butoxy-2-oxoethyl)[3-(2-tert-butoxy-2-oxoethyl) phenyl]amino}-3-oxopropyl)-3-chlorophenyl 4-[N',N"-bis (tert-butoxycarbonyl)carbamimidamido]benzoate (210 mg).

Preparation Example 42

To a solution of methyl 2-({[3-(2-chloro-4-hydroxyphenyl)propanoyl]amino}methyl)benzoate (380 mg) in N,N-dimethylformamide (4.00 mL) were added chloro tert-butyl dimethylsilane (215 mg) and imidazole (114 mg), followed by stirring at room temperature for 4 hours. To the reaction mixture were added water and 1 M hydrochloric acid, followed by extraction with ethyl acetate. The organic layer was washed with a saturated aqueous sodium chloride solution, then dried over anhydrous sodium sulfate, and concentrated under reduced pressure. The residue was purified by silica gel column chromatography (hexane-ethyl acetate) to obtain methyl 2-({[3-(4-{[tert-butyl(dimethyl)silyl]oxy}-2-chlorophenyl)propanoyl]amino}methyl)benzoate (500 mg).

Preparation Example 43

A solution of methyl 2-({[3-(4-{[tert-butyl(dimethyl)silyl] oxy}-2-chlorophenyl)propanoyl]amino}methyl)benzoate (460 mg) in concentrated hydrochloric acid (10.0 mL) was stirred at 50° C. for 4 days. The reaction mixture was concentrated under reduced pressure, then to the residue was added chloroform-methanol, and the insoluble material was separated by filtration. The filtrate was concentrated under reduced pressure, and the residue was purified by silica gel column chromatography (chloroform-methanol) to obtain 2-({[3-(2-chloro-4-hydroxyphenyl)propanoyl] amino}methyl)benzoic acid (140 mg).

Preparation Example 44

To a solution of tert-butyl 3-[4-(benzyloxy)-2-chlorophenyl]propanoate (22.5 g) in dichloromethane (67.6 mL) was added trifluoroacetic acid (24.8 mL), followed by stirring at room temperature for 3 hours. The reaction mixture was concentrated under reduced pressure, and then the residue was purified by silica gel column chromatography (hexane-ethyl acetate) to obtain 3-[4-(benzyloxy)-2-chlorophenyl]propanoic acid (13.5 g).

Preparation Example 45

To a solution of benzyl [4-(benzyloxy)-2-chlorophenyl]acetate (4.39 g) in tetrahydrofuran (80.0 mL) was added a 1 M solution of diisobutylaluminum hydride in toluene (37.0 mL) under ice-cooling under an argon atmosphere, followed by stirring for 1 hour under ice-cooling. To the reaction mixture was added a saturated aqueous Rochelle salt solution under ice-cooling. After stirring at room temperature for 2 hours, water was added thereto, followed by extraction with ethyl acetate. The organic layer was dried over anhydrous magnesium sulfate and the solvent was concentrated under reduced pressure. The residue was purified by silica gel column chromatography (hexane-ethyl acetate) to obtain 2-[4-(benzyloxy)-2-chlorophenyl]ethanol (3.01 g).

Preparation Example 46

To a solution of 2-[4-(benzyloxy)-2-chlorophenyl]ethanol (1.50 g) in dichloromethane (30.0 mL) was added 1,1,1-triacetoxy-1,1-dihydro-1,2-benziodoxol-3(1H)-one (2.70 g) under ice-cooling, followed by stirring at room temperature for 1 hour. To the reaction mixture was added a 1 M aqueous sodium thiosulfate solution, followed by extraction with chloroform. The organic layer was washed with a saturated aqueous sodium hydrogen carbonate solution and a saturated aqueous sodium chloride solution, then dried over anhydrous sodium sulfate, and concentrated under reduced pressure. The residue was purified by silica gel column chromatography (hexane-ethyl acetate) to obtain [4-(benzyloxy)-2-chlorophenyl]acetaldehyde (1.01 g).

Preparation Example 47

To a solution of (2-chloro-4-methoxyphenyl)acetaldehyde (1.22 g) in toluene (30.0 mL) was added tert-butyl (triphenylphosphoranylidene)acetate (2.75 g), followed by stirring at 80° C. overnight. The reaction mixture was air-cooled to room temperature, and then concentrated under reduced pressure. The residue was purified by silica gel column chromatography (hexane-ethyl acetate) to obtain tert-butyl (2E)-4-(2-chloro-4-methoxyphenyl)but-2-enoate (1.67 g).

Preparation Example 48

To a solution of tert-butyl 4-(2-chloro-4-methoxyphenyl)butanoate (1.73 g) in dichloromethane (10.0 mL) were added under ice-cooling, and a 1 M solution of boron tribromide in dichloromethane (12.2 mL), followed by stirring at room temperature overnight. The reaction mixture was concentrated under reduced pressure and basified by the addition of a saturated aqueous sodium hydrogen carbonate solution, and 1 M hydrochloric acid was added thereto until the liquid became acidic. The precipitated insoluble material was collected by filtration and dried under reduced pressure to obtain 4-(2-chloro-4-hydroxyphenyl)butanoic acid (647 mg).

Preparation Example 49

To a solution of methyl 5-(2-chloro-4-hydroxyphenyl)pentanoate (2.28 g) in methanol (20.0 mL) was added a 1 M aqueous sodium hydroxide solution (28.2 mL), followed by stirring at room temperature for 1 hour. To a reaction solution was added 1 M hydrochloric acid (28.2 mL), followed by extraction with chloroform. The organic layer was dried over anhydrous sodium sulfate and then concentrated under reduced pressure. The residue was purified by silica gel column chromatography (hexane-ethyl acetate) to obtain 5-(2-chloro-4-hydroxyphenyl)pentanoic acid (2.22 g) as a mixture.

Preparation Example 50

To a solution of 3-[4-(benzyloxy)-2-chlorophenyl]propanoic acid (1.00 g) in tetrahydrofuran (20.0 mL) was added 1,1'-carbonyldiimidazole (1.11 g), followed by stirring at room temperature for 2 hours. Subsequently, sodium borohydride (520 mg) and water (4.00 mL) were added thereto, followed by stirring at room temperature for 1 hour. To the reaction mixture was added 1 M hydrochloric acid, followed by extraction with ethyl acetate. The organic layer was washed with a saturated aqueous sodium hydrogen carbonate solution, then dried over anhydrous sodium sulfate, and concentrated under reduced pressure. The residue was purified by silica gel column chromatography (hexane-ethyl acetate) to obtain 3-[4-(benzyloxy)-2-chlorophenyl]propan-1-ol (861 mg).

Preparation Example 51

To a solution of 4-amino-3-chlorophenol hydrochloride (3.00 g) in pyridine (20.0 mL) were added benzyl chloroformate (2.62 mL) under ice-cooling, followed by stirring at room temperature overnight. The reaction mixture was concentrated under reduced pressure, and then the residue was purified by silica gel column chromatography (hexane-ethyl acetate) to obtain benzyl (2-chloro-4-hydroxyphenyl)carbamate (1.59 g).

Preparation Example 52

To a solution of 4 amino-3-chlorophenylphenol 4-[N',N''-bis(tert-butoxycarbonyl)carbamimidamido]benzoate (600 mg) in ethanol (6.00 mL)-tetrahydrofuran (6.00 mL) was added 1H-1,2,3-benzotriazole-1-ylmethanol (195 mg), followed by stirring at room temperature overnight. The reaction mixture was concentrated under reduced pressure, and then to the residue were added N,N-dimethylformamide (6.00 mL) and tetrahydrofuran (6.00 mL). Sodium borohydride (89.9 mg) was added thereto under ice-cooling, followed by stirring at room temperature for 3 hours. To the reaction mixture was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain 3-chloro-4-(methylamino)phenyl 4-[N',N''-bis(tert-butoxycarbonyl)carbamimidamido]benzoate (362 mg).

Preparation Example 53

To a solution of 3-chloro-4-(methylamino)phenyl 4-[N',N''-bis(tert-butoxycarbonyl)carbamimidamido]benzoate (200 mg) in dichloromethane (4.00 mL) were added pyridine (0.0341 mL), and a solution of triphosgene (40.0 mg) in dichloromethane (2.00 mL) under ice-cooling, followed by stirring at the same temperature for 30 minutes. Further, pyridine (0.0155 mL), and a solution of triphosgene (22.9 mg) in dichloromethane (2.00 mL) were added thereto, followed by stirring at the same temperature for 30 minutes. To a reaction solution was added water, followed by extraction with chloroform. The organic layer was dried over anhydrous sodium sulfate and concentrated under reduced pressure. To the residue was added dichloromethane (4.00 mL), and then pyridine (33.5 mg) and a solution of tert-butyl 3-{[(2-tert-butoxy-2-oxoethyl)amino]methyl}benzoate (124 mg) in dichloromethane (4.00 mL) were added thereto under ice-cooling, followed by stirring at room temperature overnight. To the reaction mixture was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 3-{[{[4-({4-[N',N''-bis(tert-butoxycarbonyl)carbamimidamido]benzoyl}oxy)-2-chlorophenyl](methyl) carbamoyl}(2-tert-butoxy-2-oxoethyl)amino] methyl}benzoate (315 mg).

Preparation Example 54

To a solution of tert-butyl [4-(benzyloxy)-2-chlorophenyl] carbamate (3.00 g) in N,N-dimethylformamide (45.0 mL) was added 55% sodium hydride (471 mg) under ice-cooling and a nitrogen flow, followed by stirring for 30 minutes under ice-cooling. Iodomethane (0.673 mL) was added thereto under ice-cooling, followed by stirring for 30 minutes. To the reaction mixture was added water, followed by extraction with ethyl acetate. The organic layer was dried over anhydrous sodium sulfate and concentrated under reduced pressure. The residue was purified by silica gel column chromatography (hexane-ethyl acetate) to obtain tert-butyl [4-(benzyloxy)-2-chlorophenyl]methylcarbamate (1.42 g).

Preparation Example 55

To a solution of benzyl (2-chloro-4-hydroxyphenyl)carbamate (9.26 g) in dichloromethane (100 mL) were added tetra-n-butylammonium iodide (12.3 g), diisopropyl ethylamine (11.4 mL), and [2-(chloromethoxy)ethyl](trimethyl) silane (11.8 mL) under ice-cooling, followed by stirring at room temperature for 2 hours. To the reaction mixture was added water, followed by extraction with ethyl acetate. The organic layer was dried over anhydrous sodium sulfate and concentrated under reduced pressure. The residue was purified by silica gel column chromatography (hexane-ethyl acetate) to obtain benzyl (2-chloro-4-{[2-(trimethylsilyl) ethoxy]methoxy}phenyl)carbamate (10.3 g).

Preparation Example 56

To a solution of 2-chloro-N-methyl-4-{[2-(trimethylsilyl) ethoxy]methoxy}aniline (1.00 g) in dichloromethane (20.0 mL) were added chloroacetyl chloride (0.415 mL) and triethylamine (0.872 mL) under ice-cooling, followed by stirring for 1 hour under ice-cooling. To the reaction mixture was added water, followed by extraction with ethyl acetate. The organic layer was washed with a saturated aqueous sodium chloride solution, then dried over anhydrous sodium sulfate, and concentrated under reduced pressure. The residue was purified by silica gel column chromatography (hexane-ethyl acetate) to obtain 2-chloro-N-(2-chloro-4-{[2-(trimethylsilyl)ethoxy]methoxy}phenyl)-N-methylacetamide (1.08 g).

Preparation Example 57

To a solution of 2-chloro-N-(2-chloro-4-{[2-(trimethylsilyl)ethoxy]methoxy}phenyl)-N-methylacetamide (500 mg) in acetonitrile (8.95 mL) were added tert-butyl 3-{[(2-tert-butoxy-2-oxoethyl)amino]methyl}benzoate (441 mg), potassium carbonate (285 mg), and potassium iodide (22.8 mg), followed by stirring at 60° C. overnight. To the reaction suspension was added water, followed by extraction with ethyl acetate. The organic layer was washed with water and a saturated aqueous sodium chloride solution, dried over anhydrous sodium sulfate, and concentrated under reduced pressure. The residue was purified by silica gel column chromatography (hexane-ethyl acetate) to obtain tert-butyl 3-{[(2-tert-butoxy-2-oxoethyl){2-[(2-chloro-4-{[2-(trimethylsilyl) ethoxy]methoxy}phenyl)(methyl)amino]-2-oxoethyl}amino]methyl}benzoate (809 mg).

Preparation Example 58

To a solution of tert-butyl 3-{[(2-tert-butoxy-2-oxoethyl) {2-[(2-chloro-4-{[2-(trimethylsilyl)ethoxy] methoxy}phenyl)(methyl)amino]-2-oxoethyl}amino] methyl}benzoate (805 mg) in tetrahydrofuran (16.1 mL) was added a 1 M solution of tetra-n-butylammonium in tetrahydrofuran (3.72 mL), followed by stirring at 50° C. for 4 days. To a reaction solution was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain tert-butyl 3-{[(2-tert-butoxy-2-oxoethyl){2-[(2-chloro-4-hydroxyphenyl)(methyl)amino]-2-oxoethyl}amino] methyl}benzoate (583 mg).

Preparation Example 59

To a solution of tert-butyl N-[(benzyloxy)carbonyl]-L-tyrosinate (1.00 g) in N,N-dimethylformamide (10.0 mL) were added potassium carbonate (2.71 g) and tert-butyl 2-bromo-2-methylpropanoate (2.01 mL), followed by stirring at 90° C. overnight. To the reaction suspension was added water, followed by extraction with ethyl acetate. The organic layer was dried over anhydrous sodium sulfate and concentrated under reduced pressure. The residue was purified by silica gel column chromatography (hexane-ethyl acetate) to obtain tert-butyl N-[(benzyloxy)carbonyl]-O-(1-tert-butoxy-2-methyl-1-oxopropan-2-yl)-L-tyrosinate (1.21 g).

Preparation Example 60

To a solution of 6-hydroxy-1H-indole-2-carboxylic acid (2.66 g) in N,N-dimethylformamide (25.0 mL) was added lithium carbonate (1.22 g), followed by stirring at room temperature for 10 minutes. Benzyl bromide (2.14 mL) was added thereto, followed by stirring at 100° C. for 2 hours. The reaction mixture was lowered to 60° C., and 1 M hydrochloric acid (40.0 mL) was added thereto, followed by leaving to be cooled and extracting with ethyl acetate. The organic layer was washed with a saturated aqueous sodium hydrogen carbonate solution and a saturated aqueous sodium chloride solution, dried over anhydrous sodium sulfate, and then concentrated under reduced pressure. The residue was purified by silica gel column chromatography (hexane-ethyl acetate), and the crude purified product was washed with cold ethanol (5.00 mL) to obtain benzyl 6-hydroxy-1H-indole-2-carboxylate (1.95 g).

Preparation Example 61

To a solution of 6-hydroxy-1H-indole-3-carboxylic acid (1.05 g) in N,N-dimethylformamide (11.0 mL) were added sodium carbonate (722 mg) and benzyl bromide (0.775 mL), followed by stirring at room temperature overnight. To the reaction suspension was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (chloroform-methanol) to obtain benzyl 6-hydroxy-1H-indole-3-carboxylate (1.04 g).

Preparation Example 62

To a solution of tert-butyl 4-(bromomethyl)thiophene-2-carboxylate (2.00 g) in N,N-dimethylformamide (19.8 mL) were added tert-butyl L-alaninate hydrochloride (2.62 g) and triethylamine (4.02 mL), followed by heating at 60° C. for 12 hours. To the reaction suspension was added water, followed by extraction with ethyl acetate. The organic layer was washed with a saturated aqueous sodium chloride solution, then dried over anhydrous magnesium sulfate, and concentrated under reduced pressure. The residue was purified by silica gel column chromatography (hexane-ethyl acetate) to obtain tert-butyl 4-({[(2S)-1-tert-butoxy-1-oxopropan-2-yl] amino}methyl)thiophene-2-carboxylate (1.31 g).

Preparation Example 63 tert-Butyl 3 (2,6-difluoro-4-methoxyphenyl)propanoate (11.7 g) was suspended in 48% aqueous hydrogen bromide (200 mL), followed by stirring at 120 □ C for 16 hours. The reaction mixture was concentrated under reduced pressure, and then to the residue was added water, followed by extraction with ethyl acetate. The organic layer was washed with water and a saturated aqueous sodium chloride solution, then dried over anhydrous sodium sulfate, and concentrated under reduced pressure. The residue was purified by silica gel column chromatography (hexane-ethyl acetate) to obtain 3-(2, 6-difluoro-4-hydroxyphenyl)propanoic acid (3.17 g).

Preparation Example 64

To a solution of tert-butyl 4-{[(2-tert-butoxy-2-oxoethyl) {2-[(4-{[tert-butyl(dimethyl)silyl]oxy}-2-chlorophenyl) amino]-2-oxoethyl}amino]methyl}thiophene-2-carboxylate (375 mg) in tetrahydrofuran (7.50 mL) was added 55% sodium hydride (25.2 mg) under ice-cooling, followed by stirring at room temperature for 30 minutes. Iodomethane (0.187 mL) was added thereto at room temperature, followed by stirring at room temperature for 2 hours. To the reaction mixture was added ethyl acetate, and water and a saturated aqueous ammonium chloride solution was added thereto under ice-cooling. The organic layer was extracted, then dried over anhydrous magnesium sulfate, and concentrated under reduced pressure. The residue was purified by silica gel column chromatography (hexane-ethyl acetate) to obtain tert-butyl 4-{[(2-tert-butoxy-2-oxoethyl) {2-[(4-{[tert-butyl (dimethyl)silyl]oxy}-2-chlorophenyl)(methyl)amino]-2-oxoethyl}amino]methyl}thiophene-2-carboxylate (209 mg).

Preparation Example 65

To a solution of 4-amino-3-fluorobenzoic acid (500 mg) in tetrahydrofuran (10.0 mL) was added N,N'-bis-tert-butoxycarbonyl-1-guanylpyrazole (1.20 g), followed by stirring at room temperature for 3 days. The reaction suspension was concentrated under reduced pressure, and then the residue was purified by silica gel column chromatography (chloroform-methanol) to obtain 4-[N',N''-bis(tert-butoxycarbonyl) carbamimidamido]-3-fluorobenzoic acid (669 mg).

Preparation Example 66

To a solution of tert-butyl (3-formylphenoxy)acetate (1.50 g) in dichloroethane (20.0 mL) were added tert-butyl glycinate (874 mg) and acetic acid (1.09 mL), and then sodium triacetoxyborohydride (2.69 g) was added thereto under ice-cooling. The reaction suspension was stirred at room temperature for 16 hours. To the reaction mixture was added a saturated aqueous sodium hydrogen carbonate solution, followed by extraction with ethyl acetate. The organic layer was washed with a saturated aqueous sodium chloride solution, dried over anhydrous sodium sulfate, and concentrated under reduced pressure. The residue was purified by silica gel column chromatography (chloroform-methanol) to obtain tert-butyl N-[3-(2-tert-butoxy-2-oxoethoxy)benzyl]glycinate (1.18 g).

Preparation Example 67

To a solution of tert-butyl [2-(chloromethyl)phenyl]acetate (2.31 g) in acetonitrile (23.1 mL) were added tert-butyl glycinate hydrochloride (2.41 g) and triethylamine (4.01 mL), followed by heating at 60° C. for 3 hours. The reaction suspension was concentrated under reduced pressure, then to the residue were added water and ethyl acetate, and the organic layer was extracted. The organic layer was dried over anhydrous magnesium sulfate and concentrated under reduced pressure. The residue was purified by silica gel column chromatography (hexane-ethyl acetate) to obtain tert-butyl N-[2-(2-tert-butoxy-2-oxoethyl)benzyl]glycinate (2.54 g).

Preparation Example 68

To a solution of 5-methyl-1-benzothiophene-2-carboxylic acid (1.50 g) in N,N-dimethylformamide (10.5 mL) was added 1,1'-carbonyldiimidazole (1.27 g), followed by stirring at room temperature for 2.5 hours. Subsequently, tert-butyl alcohol (1.44 mL) and 1,8-diazabicyclo[5.4.0]undeca-7-ene (1.17 mL) were added thereto, followed by heating at 50° C. for 24 hours. To the reaction mixture was added ethyl acetate, and the organic layer was washed with 1 M hydrochloric acid and a saturated aqueous sodium chloride solution in this order, and then concentrated under reduced pressure. The residue was purified by silica gel column chromatography (hexane-ethyl acetate) to obtain tert-butyl 5-methyl-1-benzothiophene-2-carboxylate (1.78 g).

Preparation Example 69 tert-Butyl 3-{[{2-[4-({4-[N',N''-bis(tert-butoxycarbonyl) carbamimidamido]benzoyl}oxy)-2-chlorophenyl]propanoyl}(2-tert-butoxy-2-oxoethyl)amino]methyl}benzoate (300 mg) was preparatively purified by a supercritical chromatography method ($CO_2$-methanol) by means of a UV trigger, and then concentrated under reduced pressure to obtain PEx. 69-1 (135 mg, RT: 5.90 min) and PEx. 69-2 (134 mg, RT: 7.35 min), respectively, as both enantiomers of tert-butyl 3-{[{2-[4-({4-[N',N''-bis(tert-butoxycarbonyl)carbamimidamido]benzoyl}oxy)-2-chlorophenyl]propanoyl}(2-tert-butoxy-2-oxoethyl)amino]methyl}benzoate. Further, the conditions for the supercritical chromatography method carried out to obtain RT are shown below.

Column; CHIRALPAK IC 10×250 mm (particle diameter: 5 μm) (manufactured by Daicel Chemical Industries, Ltd.
  Mobile phase; $CO_2$ 70%, methanol 30%
  Flow rate; 10 mL/min
  Detection wavelength; 220 to 300 nm
  Column temperature; 40° C.
  Discharge pressure; 100 bar
  Injection amount; 200 μL
  Compound concentration; 20 mg/mL
  Dissolution solvent; methanol Preparation Example 70

To a solution of tert-butyl [4-(aminomethyl)phenyl]acetate (1.00 g) in acetonitrile (15.0 mL) were added tert-butyl bromoacetate (0.668 mL) and triethylamine (0.693 mL), followed by stirring at room temperature for 4 hours. The reaction suspension was concentrated under reduced pressure, and then to the residue was added ethyl acetate. The organic layer was washed with 0.1 M hydrochloric acid, a saturated aqueous sodium hydrogen carbonate solution, and a saturated aqueous sodium chloride solution in this order, dried over anhydrous magnesium sulfate, and concentrated under reduced pressure. The residue was purified by silica gel column chromatography (hexane-ethyl acetate) to obtain tert-butyl N-[4-(2-tert-butoxy-2-oxoethyl)benzyl]glycinate (747 mg).

Preparation Example 71

To a mixture of 1-[4-(benzyloxy)-2-chlorophenyl]ethanone (500 mg) and toluene (15.0 mL) were added p-toluenesulfonic acid (110 mg) and tert-butyl glycinate (0.800 mL), followed by heating at 120° C. for 18 hours. After completion, the reaction mixture was left to be cooled, and then concentrated under reduced pressure. To the residue was added methanol (10.0 mL), and the sodium borohydride (90.0 mg) was added there to under ice-cooling, followed by stirring under ice-cooling for 2 hours. To the reaction mixture were added a saturated aqueous ammonium chloride solution and ethyl acetate, and the organic layer was extracted. The organic layer was dried over anhydrous magnesium sulfate and concentrated under reduced pressure. The residue was purified by silica gel column chromatography (hexane-ethyl acetate) to obtain tert-butyl N-{1-[4-(benzyloxy)-2-chlorophenyl]ethyl}glycinate (560 mg).

Preparation Example 72

To a solution of 2-benzyl 1-tert-butyl (2S,4R)-4-hydroxypyrrolidine-1,2-dicarboxylate (565 mg) in tetrahydrofuran (10.0 mL) were added benzyl 4-hydroxybenzoate (405 mg) and 1,1'-(azodicarbonyl)dipiperidine (555 mg), and then tri-n-butyl phosphine (0.540 mL) was added thereto under ice-cooling, followed by stirring at room temperature overnight. The reaction mixture was concentrated under reduced pressure, and then the residue was purified by silica gel column chromatography (hexane-ethyl acetate) to obtain 2-benzyl 1-tert-butyl (2S,4S)-4-{4-[(benzyloxy)carbonyl]phenoxy}pyrrolidine-1,2-dicarboxylate (273 mg).

Preparation Example 73

To a solution of 2-chloro-4-hydroxybenzaldehyde (400 mg) in dichloromethane (4.00 mL) were added anhydrous magnesium sulfate (615 mg) and tert-butyl glycinate hydrochloride (679 mg), followed by stirring at room temperature overnight. The reaction mixture was filtered, and then the filtrate was concentrated under reduced pressure. The residue was dissolved in methanol (12.0 mL), and sodium borohydride (193 mg) was added thereto, followed by stirring at room temperature for 2 hours. To the reaction mixture were added water and ethyl acetate, and the organic layer was extracted. The organic layer was washed with a saturated aqueous sodium chloride solution, then dried over anhydrous magnesium sulfate, and concentrated under reduced pressure to obtain tert-butyl N-(2-chloro-4-hydroxybenzyl)glycinate (613 mg).

Preparation Example 74

To a solution of dimethyl(benzyloxycarbonyl)methylphosphonate (2.20 g) in tetrahydrofuran (32.0 mL) was added 55% sodium hydride (406 mg) under ice-cooling, followed by stirring at room temperature for 30 minutes. Subsequently, tert-butyl 3-formylbenzoate (1.60 g) was added thereto, followed by stirring at room temperature for 16 hours. To the reaction mixture were added water and ethyl acetate, and the organic layer was extracted. The organic layer was washed with a saturated aqueous sodium hydrogen carbonate solution and a saturated aqueous sodium chloride solution, then dried over anhydrous sodium sulfate, and concentrated under reduced pressure. The residue was purified by silica gel column chromatography (hexane-ethyl acetate) to obtain tert-butyl 3-[(1E)-3-(benzyloxy)-3-oxopropa-1-en-1-yl]benzoate (1.60 g).

Preparation Example 75

To a solution of di-tert-butyl 5-(bromomethyl)isophthalate (1.00 g) in tetrahydrofuran (10.0 mL) were added a 70% aqueous ethylamine solution (2.21 mL), followed by stirring at room temperature overnight. To the reaction mixture were added water and ethyl acetate, and the organic layer was extracted. The organic layer was washed with water, dried over anhydrous sodium sulfate, and concentrated under reduced pressure. The residue was purified by silica gel column chromatography (hexane-ethyl acetate, and subsequently chloroform-methanol) to obtain di-tert-butyl 5-[ethylamino(methyl)]isophthalate (558 mg).

Preparation Example 76

To a solution of ethyl 3-(2-chloro-4-{[2-(trimethylsilyl)ethoxy]methoxy}phenyl)buta-2-enoate (525 mg) in tetrahydrofuran (10.0 mL) was added 5% rhodium carbon (200 mg), followed by stirring at room temperature for 18 hours under hydrogen atmosphere. The reaction suspension was filtered through Celite, the filtrate was concentrated under reduced pressure, and then the residue was purified by silica gel column chromatography (hexane-ethyl acetate) to obtain ethyl 3-(2-chloro-4-{[2-(trimethylsilyl)ethoxy]methoxy}phenyl)butanoate (282 mg).

Preparation Example 77

To a solution of 55% sodium hydride (128 mg) in tetrahydrofuran (15.0 mL) was added benzyl 2-(dimethoxyphosphoryl)propanoate (796 mg) under ice-cooling, followed by stirring for 30 minutes under ice-cooling. Subsequently, a solution of 4-{[tert-butyl(dimethyl)silyl]oxy}-2-chlorobenzaldehyde (720 mg) in tetrahydrofuran (3.00 mL) was added thereto, followed by stirring at room temperature for 4 hours. To the reaction mixture were added a saturated aqueous ammonium chloride solution, water, and ethyl acetate, and the organic layer was extracted. The organic layer was dried over anhydrous magnesium sulfate and concentrated under reduced pressure. To a solution of the residue in tetrahydrofuran (10.0 mL) was added a 1 M solution of tetra-n-butylammonium fluoride in tetrahydrofuran (2.70 mL) under ice-cooling, followed by stirring for 30 minutes under ice-cooling. After completion, to the reaction mixture were added a saturated aqueous ammonium chloride solution, water, and ethyl acetate, and the organic layer was extracted. The organic layer was dried over anhydrous magnesium sulfate and concentrated under reduced pressure. The residue was purified by silica gel column chromatography (hexane-ethyl acetate) to obtain benzyl (2E)-3-(2-chloro-4-hydroxyphenyl)-2-methylacrylate (587 mg).

Preparation Example 78

To a solution of 6-hydroxyquinoline-2-carboxylic acid (2.00 g) in N,N-dimethylformamide (20.0 mL) were added potassium carbonate (3.07 g) and benzyl bromide (3.02 mL), followed by stirring at 50° C. for 6 hours. The reaction mixture was left to be cooled, 1 M hydrochloric acid, ethyl acetate, and tetrahydrofuran were added thereto, and the organic layer was extracted. The organic layer was washed with water and a saturated aqueous sodium chloride solution, then dried over anhydrous sodium sulfate, and concentrated under reduced pressure. The residue was purified by hexane-ethyl acetate to obtain benzyl 6-(benzyloxy)quinoline-2-carboxylate (1.80 g).

Preparation Example 79

To a solution of benzyl 6-(benzyloxy)quinoline-2-carboxylate (650 mg) in tetrahydrofuran (13.0 mL) was added a 1 M solution diisobutylaluminum hydride in toluene (2.64 mL) at −78° C., followed by stirring at −78° C. for 1 hour. To the reaction mixture was added sodium sulfate decahydrate (680 mg), followed by stirring at room temperature overnight. The insoluble material was collected by filtration and the filtrate was concentrated under reduced pressure. The residue was purified by silica gel column chromatography (hexane-ethyl acetate) to obtain 6-(benzyloxy)quinoline-2-carbaldehyde (170 mg).

Preparation Example 80

To a solution of 2-bromo-1,3,5-trimethylbenzene (1.22 g) in tetrahydrofuran (20.0 mL) was added a 1.59 M solution of n-butyllithium in n-hexane (3.86 mL) at −78° C., followed by stirring at −78° C. for 30 minutes. Subsequently, a solution of tert-butyl (4-bromo-2-thienyl)acetate (1.55 g) in tetrahydrofuran (15.0 mL) was added thereto, followed by stirring at −78° C. for 30 minutes. Subsequently, a 1.59 M solution of n-butyllithium in n-hexane (3.51 mL) was added thereto at −78° C., followed by stirring at −78° C. for 30 minutes. Further, N,N-dimethylformamide (0.451 mL) was added thereto, followed by stirring at −78° C. for 1 hour. To the reaction mixture were added a saturated aqueous ammonium chloride solution and ethyl acetate, and the organic layer was extracted. The organic layer was dried over anhydrous magnesium sulfate and concentrated under reduced pressure. The residue was purified by silica gel column chromatography (hexane-ethyl acetate) to obtain tert-butyl (4-formyl-2-thienyl)acetate (355 mg).

Example 1

To tert-butyl N-{[4-({4-[N',N''-bis(tert-butoxycarbonyl)carbamimidamido]benzoyl}oxy)-2-chlorophenyl]acetyl}-O-tert-butyl-L-tyrosinate (210 mg) was added a 4 M solution of hydrogen chloride in dioxane (6.38 mL), followed by stirring overnight. The reaction mixture was concentrated under reduced pressure to obtain N-({4-[(4-carbamimidamidobenzoyl)oxy]-2-chlorophenyl}acetyl)-L-tyrosine hydrochloride (120 mg).

Example 2

To a solution of tert-butyl N-{[4-({4-[N',N''-bis(tert-butoxycarbonyl)carbamimidamido]benzoyl}oxy)-2-chlorophenyl]acetyl}-1-trityl-L-histidinate (265 mg) in dichloromethane (2.70 mL) was added trifluoroacetic acid (0.619 mL) under ice-cooling, followed by stirring at room temperature overnight. The reaction mixture was concentrated under reduced pressure and washed with water, and the filtrate was concentrated under reduced pressure. The residue was purified by ODS silica gel column chromatography (0.01 M hydrochloric acid-acetonitrile), and the purified product was dried under reduced pressure to obtain N-({4-[(4-carbamimidamidobenzoyl)oxy]-2-chlorophenyl}acetyl)-L-histidine 2 hydrochloride (54.1 mg).

Example 3

3-{[(3-{4-[(4-Carbamimidamidobenzoyl)oxy]-2-chlorophenyl}propanoyl)(carboxymethyl)amino]methyl}benzoic acid hydrochloride (727 mg) was dissolved in a 50% aqueous acetonitrile solution (24.0 mL), and a 1 M aqueous sodium hydroxide solution (1.20 mL) was added thereto at room temperature. After stirring at room temperature for 5 hours, the resulting solid was collected by filtration and washed with a 50% aqueous acetonitrile solution. To the obtained solid was added a 50% aqueous acetonitrile solution (50.0 mL), followed by stirring at 100° C. for 30 minutes, then slowly cooling to room temperature, and stirring at room temperature overnight. The resulting solid was collected by filtration, washed with a 50% aqueous acetonitrile solution, and dried at 40° C. under reduced pressure. The obtained solid (601 mg) was suspended in a 50% aqueous acetone solution (16.0 mL), and methane sulfonic acid (0.160 mL) was added thereto at room temperature. After stirring at room temperature overnight, the solvent was evaporated under reduced pressure. Next, acetone (25.0 mL) was added thereto, followed by stirring at 50° C. for 2 hours. After cooling to room temperature, the precipitated crystals were collected by filtration and then dried at 40° C. under reduced pressure to obtain 3-{[(3-{4-[(4-carbamimidamidobenzoyl)oxy]-2-chlorophenyl}propanoyl)(carboxymethyl)amino]methyl}benzoic acid mesylate (679 mg).

Example 4

To a solution of tert-butyl 3-{[{[6-({4-[N',N''-bis(tert-butoxycarbonyl)carbamimidamido]benzoyl}oxy)quinolin-2-yl]carbonyl}(2-tert-butoxy-2-oxoethyl)amino]methyl}benzoate (659 mg) in dichloromethane (5.00 mL) was added trifluoroacetic acid (2.40 mL), followed by stirring at room temperature overnight. The reaction solution was concentrated under reduced pressure, and then to the residue was added acetonitrile (20.0 mL), followed by concentrating under reduced pressure again. This operation was repeated twice, and then acetonitrile (20.0 mL) was added thereto, followed by stirring at room temperature for 1 hour, and further heating and refluxing at 100° C. for 2 hours. The reaction solution was ice-cooled, and then 1 M sodium hydroxide (1.54 mL) was added thereto. Subsequently, a saturated aqueous sodium hydrogen carbonate solution was added thereto to adjust the pH to around 5. After stirring for 1 hour under ice-cooling, the insoluble matter was collected by filtration, and the filtrate was washed with a 50% aqueous acetonitrile solution and then dried at 50° C. for under reduced pressure. The dried product (354 mg) was suspended in a 33% aqueous acetonitrile solution (9.00 mL), and then methane sulfonic acid (0.100 mL) was added thereto. After stirring at 60° C. for 30 minutes, water (6.00 mL) was added thereto, followed by stirring at room temperature overnight. The precipitated crystals were collected by filtration, washed with a 10% aqueous acetonitrile solution, and then dried under reduced pressure to obtain 3-{[({6-[(4-carbamimidamidobenzoyl)oxy]quinolin-2-yl}carbonyl)(carboxymethyl)amino]methyl}benzoic acid (236 mg).

Example 5

To a solution of tert-butyl 3-{[{2-[4-({4-[N',N''-bis(tert-butoxycarbonyl)carbamimidamido]benzoyl}oxy)-2-chlorophenyl]propanoyl}(2-tert-butoxy-2-oxoethyl)amino]methyl}benzoate (180 mg) in dichloromethane (1.92 mL) was added trifluoroacetic acid (0.646 mL), followed by stirring at room temperature overnight. After completion, the reaction solution was concentrated under reduced pressure, and then to the residue was added acetonitrile (20.0 mL), followed by concentrating under reduced pressure again. This operation was repeated twice, to the residue was added a 50% aqueous acetonitrile solution (5.00 mL), and a 1 M aqueous sodium hydroxide solution (0.208 mL) was added thereto under ice-cooling. After stirring for 1 hour under ice-cooling, the precipitated crystals were collected by filtration, and washed with a 10% aqueous acetonitrile solution and then dried under reduced pressure to obtain 3-{[(2-{4-[(4-carbamimidamidobenzoyl)oxy]-2-chlorophenyl}propanoyl)(carboxymethyl)amino]methyl}benzoic acid (92 mg).

Example A1

To a solution of di-tert-butyl L-aspartate hydrochloride (40 μmoL) were added 0.5 mL of a solution of 3-(4-hydroxyphenyl)propionic acid (299 mg) and 4-dimethylaminopyridine (220 mg) in N,N-dimethylformamide (30 mL), and 0.5 mL of a solution of N-(3-dimethylaminopropyl)-N'-ethylcarbodiimide hydrochloride (518 mg) in N,N-dimethylformamide (30 mL), followed by stirring at room temperature overnight. After concentrating under reduced pressure, 1.0 mL of a solution of 4-[N',N''-bis(tert-butoxycarbonyl)carbamimidamido]benzoic acid (911 mg) in dichloromethane (60 mL) and 0.5 mL of a solution of N-(3-dimethylaminopropyl)-N'-ethylcarbodiimide hydrochloride (518 mg) in dichloromethane (30 mL) were added thereto, followed by stirring at room temperature overnight. Trifluoroacetic acid (0.5 mL) was added thereto, followed by stirring further at room temperature overnight. After concentrating under reduced pressure, the product was preparatively purified with LC (aqueous formic acid solution/methanol) by means of an MS trigger, and then concentrated under reduced pressure to obtain N-(3-{4-[(4-carbamimidamidobenzoyl)oxy]phenyl}propanoyl)-L-aspartic acid (4.7 mg).

Here, the conditions for HPLC carried out to obtain a retention time (RT) are shown below.

Liquid column chromatography system: ACQUITY UPLC System

Column: ACQUITY UPLC HSS T3 (Waters) (particle diameter: 1.8 μm, internal diameter: 2.1 mm, and length: 50 mm)

Mobile phase: A Solution 0.1% aqueous formic acid solution, and B Solution 0.1% formic acid solution in methanol Flow rate: 0.7 mL/min; Detection wavelength: 254 nm; Column temperature: 40.0° C.; Injection amount: 1 μL

TABLE 3

| Time (min) | A sol (%) | B sol (%) | Elution |
|---|---|---|---|
| 0-3 | 95 | 5 | Gradient |
| 3-4 | 10 | 90 | Isocratic |

The compounds shown in Tables below were prepared in the same manner as in Preparation Examples and Examples as described above.

The chemical structural formulae of the compounds of Preparation Examples are shown in Tables 4 to 60; the preparation methods and the physicochemical data of the compounds of Preparation Examples are shown in Tables 61 to 66; the chemical structural formulae of the compounds of Examples are shown in Tables 67 to 89; and the preparation methods and the physicochemical data of the compounds of Examples are shown in Tables 90 to 95. Further, the compounds of Examples A2 to A45 shown in Tables below were prepared in the same manner as the method of Example A1. The chemical structural formulae, the physicochemical data, and RT of the respective compounds of Examples are shown in Tables 96 to 103.

TABLE 4

| PEx | Str |
|---|---|
| 1 | |
| 2 | |

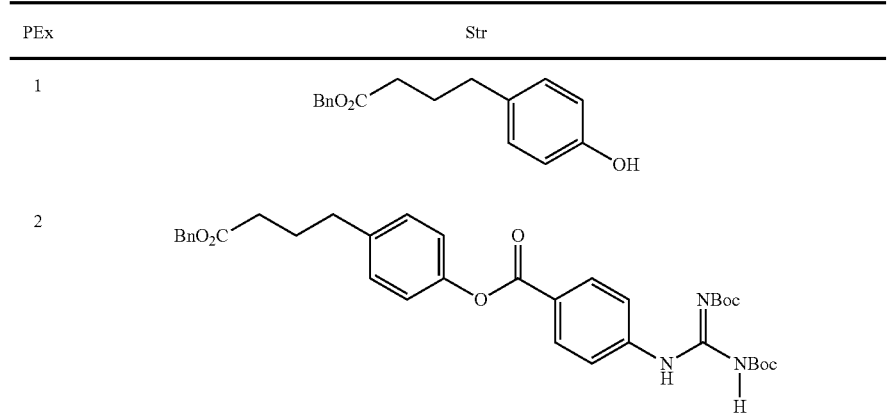

TABLE 4-continued
| PEx | Str |
|---|---|
| 3 | 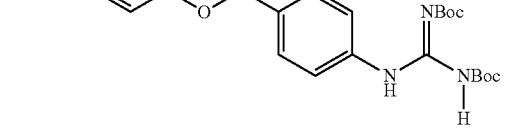 |
| 4 | 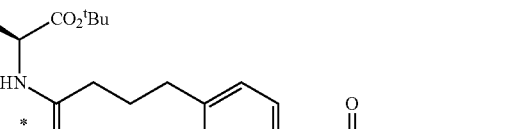 |
| 5 | 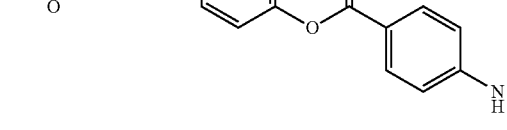 |
| 6 | 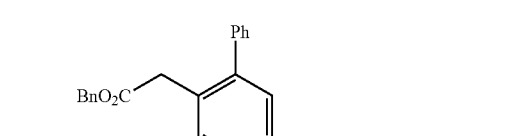 |
| 7 | 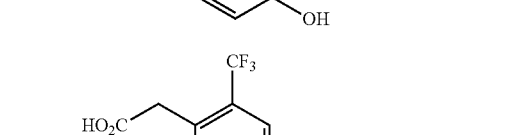 |
| 8 | 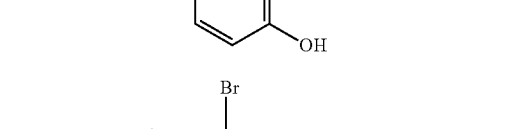 |
TABLE 5
| PEx | Str |
|---|---|
| 9 |  |
| 10 |  |

TABLE 5-continued
| PEx | Str |
|---|---|
| 11 | 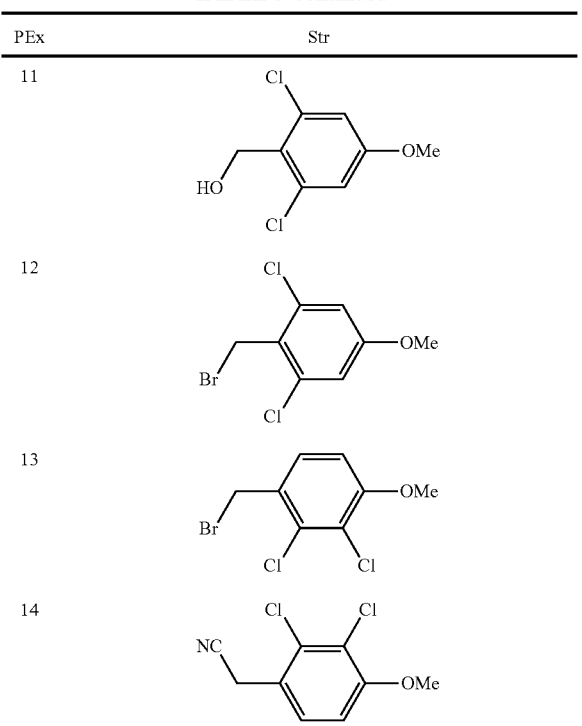 |
| 12 | |
| 13 | |
| 14 | |
TABLE 5-continued
| PEx | Str |
|---|---|
| 15 | 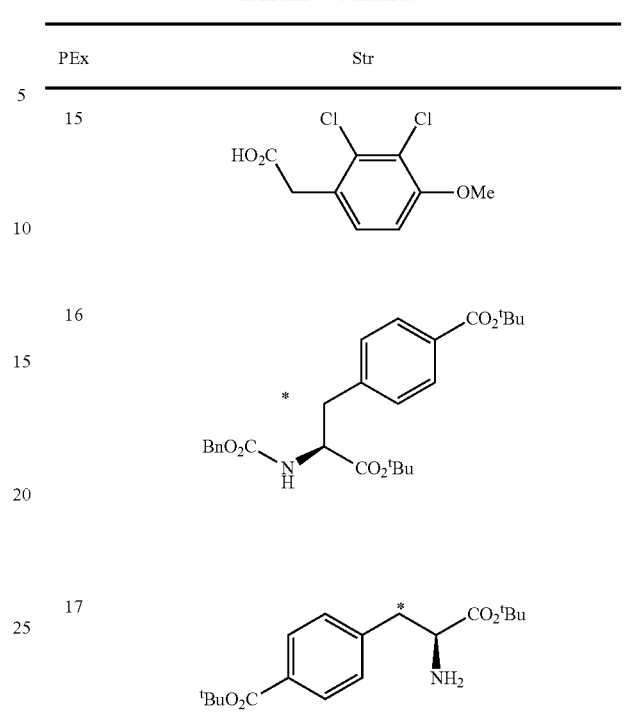 |
| 16 | |
| 17 | |
TABLE 6
| PEx | Str |
|---|---|
| 18 | 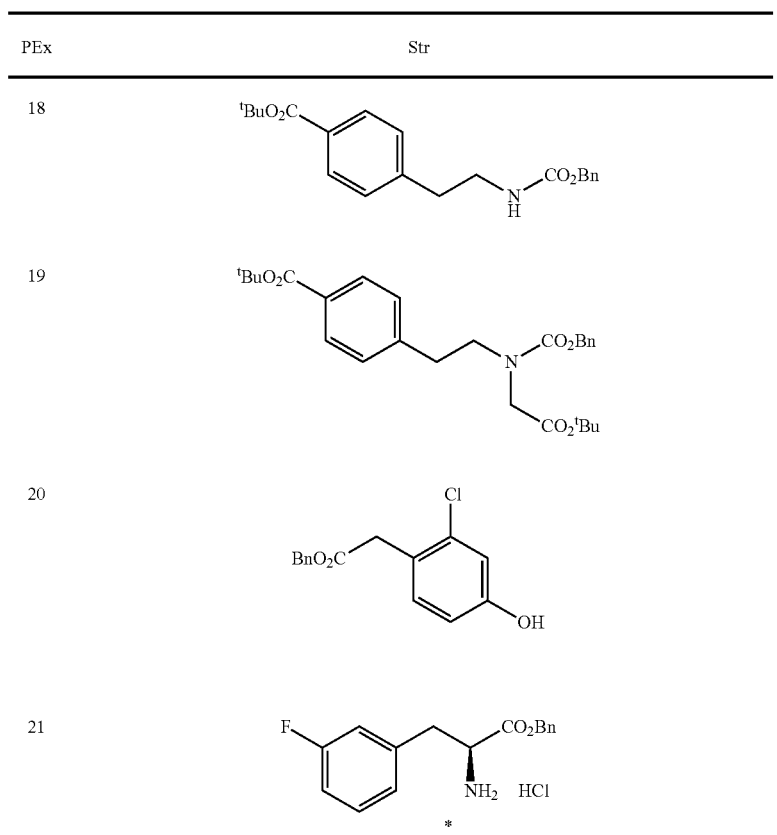 |
| 19 | |
| 20 | |
| 21 | |

TABLE 6-continued

| PEx | Str |
|---|---|
| 22 | 3-fluorophenyl-L-alanine with CO₂H, linked via HN-C(=O)-CH₂ to 2-chloro-4-(4-(N,N'-di-Boc-guanidino)benzoyloxy)phenyl; chiral center marked * |
| 23 | Ph-CH₂-CH(CO₂ᵗBu)-NH-*-CH₂-CO₂ᵗBu (L-configuration) |
| 24 | Ph-CH₂-CH(CO₂ᵗBu)-NH-CH₂-(3-CO₂ᵗBu-phenyl), * on benzyl CH₂ |
| 25 | ᵗBuO₂C-(3-phenyl)-CH₂CH₂-NH-CH₂-CO₂ᵗBu |

TABLE 7

| PEx | Str |
|---|---|
| 26 | ᵗBuO₂C-CH₂-N(CH₂CH₂Ph)-C(=O)-CH₂-(2-chloro-4-(4-(N,N'-di-Boc-guanidino)benzoyloxy)phenyl) |
| 27 | (E)-benzyl 3-(4-hydroxy-2-chlorophenyl)acrylate (CO₂Bn) |
| 28 | ᵗBuO₂C-(3-phenyl)-CH₂-NH-CH₂-CO₂ᵗBu |
| 29 | O₂N-(3-phenyl)-CH₂-N(C(=O)CF₃)-CH₂-CO₂ᵗBu |

TABLE 7-continued

| PEx | Str |
|---|---|
| 30 | H₂N-C₆H₄-CH₂-N(COCF₃)-CH₂-CO₂ᵗBu |
| 31 | Boc-NH-SO₂-NH-C₆H₄-CH₂-N(COCF₃)-CH₂-CO₂ᵗBu |
| 32 | Boc-NH-SO₂-NH-C₆H₄-CH₂-NH-CH₂-CO₂ᵗBu |
| 33 | (HO-N=)(H₂N-)C-C₆H₄-CH₂-N(COCF₃)-CH₂-CO₂ᵗBu |
| 34 | (5-oxo-4H-1,2,4-oxadiazol-3-yl)-C₆H₄-CH₂-N(COCF₃)-CH₂-CO₂ᵗBu |

TABLE 8

| PEx | Str |
|---|---|
| 35 | EtO₂C-(pyridine-2,6-diyl)-CH₂-NH-CH₂-CO₂ᵗBu |
| 36 | EtO₂C-(pyridine-2,6-diyl)-CH₂-N(CO₂Bn)-CH₂-CO₂ᵗBu |
| 37 | HO₂C-(pyridine-2,6-diyl)-CH₂-N(CO₂Bn)-CH₂-CO₂ᵗBu |
| 38 | 4-(CO₂ᵗBu)-2-(BrCH₂)-quinoline |
| 39 | 3-(H₂NCH₂)-5-F-C₆H₃-CO₂ᵗBu |

TABLE 8-continued

| PEx | Str |
|---|---|
| 40 | (structure: tBuO2C-phenyl-CH2-NH-phenyl-CO2tBu) |
| 41 | (structure: tBuO2C-CH2-phenyl-N(CH2CO2tBu)-C(=O)-CH2CH2-(3-Cl-phenyl)-O-C(=O)-phenyl-NH-C(=NBoc)-NHBoc) |
| 42 | (structure: TBSO-(2-Cl-phenyl)-CH2CH2-C(=O)-NH-CH2-phenyl-CO2Me) |
| 43 | (structure: HO-(2-Cl-phenyl)-CH2CH2-C(=O)-NH-CH2-phenyl-CO2H) |

TABLE 9

| PEx | Str |
|---|---|
| 44 | (HO2C-CH2CH2-(2-Cl-4-OBn-phenyl)) |
| 45 | (HO-CH2CH2-(2-Cl-4-OBn-phenyl)) |
| 46 | (OHC-CH2-(2-Cl-4-OBn-phenyl)) |
| 47 | (tBuO2C-CH=CH-(2-Cl-4-OMe-phenyl)) |
| 48 | (HO2C-CH2CH2CH2-(2-Cl-4-OH-phenyl)) |
| 49 | (HO2C-(CH2)4-(2-Cl-4-OH-phenyl)) |
| 50 | (HO-CH2CH2CH2-(2-Cl-4-OBn-phenyl)) |
| 51 | (BnO2C-NH-(2-Cl-4-OH-phenyl)) |

TABLE 9-continued

| PEx | Str |
|---|---|
| 52 | (structure) |

TABLE 10

| PEx | Str |
|---|---|
| 53 | (structure) |
| 54 | (structure) |
| 55 | (structure) |
| 56 | (structure) |
| 57 | (structure) |

TABLE 10-continued

| PEx | Str |
|---|---|
| 58 | (structure) |
| 59 | (structure) |

TABLE 11

| PEx | Str |
|---|---|
| 60 | (structure) |
| 61 | (structure) |
| 62 | (structure) |
| 63 | (structure) |
| 64 | (structure) |
| 65 | (structure) |

TABLE 11-continued
| PEx | Str |
|---|---|
| 66 | 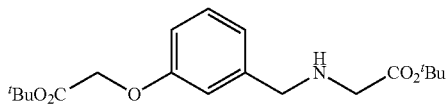 [SMILES: CC(C)(C)OC(=O)CNCc1cccc(OCC(=O)OC(C)(C)C)c1] |
| 67 | 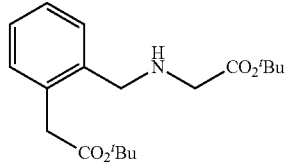 [SMILES: CC(C)(C)OC(=O)CNCc1ccccc1CC(=O)OC(C)(C)C] |
TABLE 12
| PEx | Str |
|---|---|
| 68 | 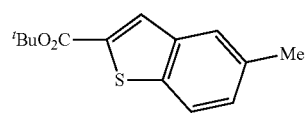 |
| 69-1 | 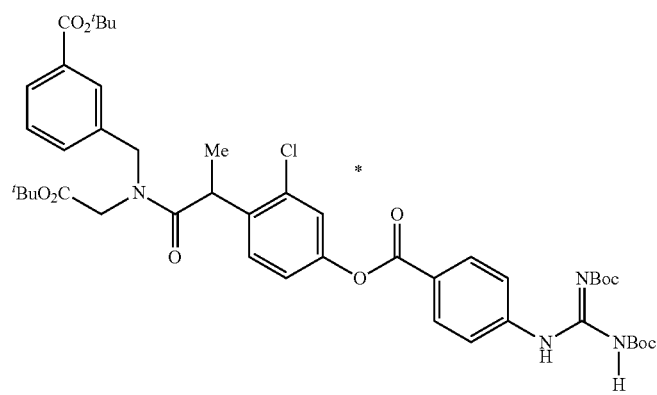 |
| 69-2 | 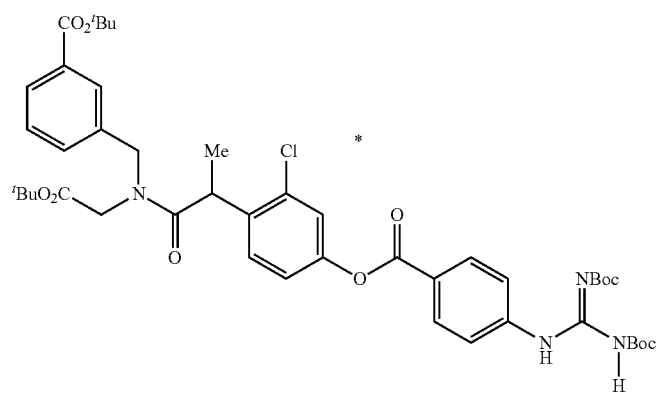 |
| 70 | 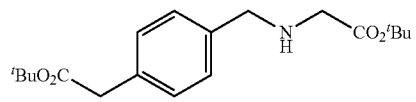 [SMILES: CC(C)(C)OC(=O)CNCc1ccc(CC(=O)OC(C)(C)C)cc1] |
| 71 | 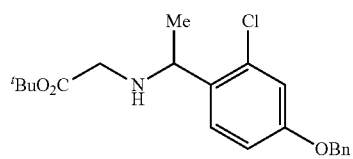 [SMILES: CC(NCC(=O)OC(C)(C)C)c1ccc(OCc2ccccc2)cc1Cl] |

TABLE 12-continued
| PEx | Str |
|---|---|
| 72 | 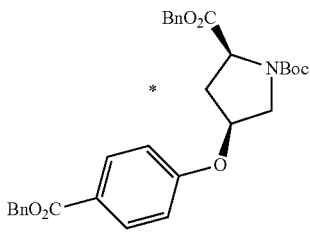 |
| 73 | 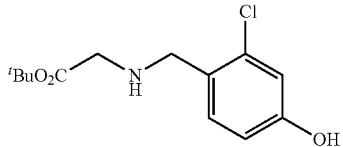 [SMILES: CC(C)(C)OC(=O)CNCc1ccc(O)cc1Cl] |
TABLE 13
| PEx | Str |
|---|---|
| 74 | 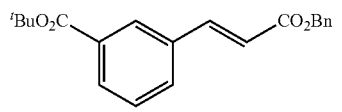 [SMILES: CC(C)(C)OC(=O)c1cccc(/C=C/C(=O)OCc2ccccc2)c1] |
| 75 | 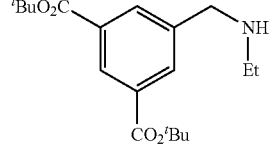 |
| 76 | 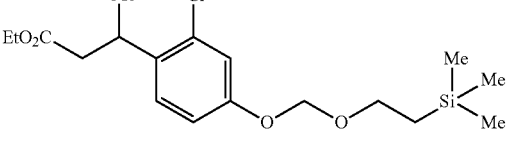 |
| 77 | 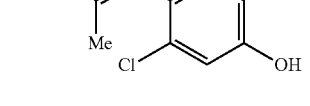 |
| 78 | 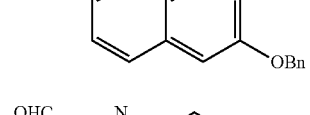 |
| 79 | 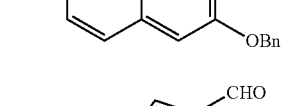 |
| 80 | 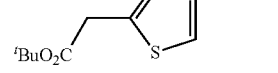 |

TABLE 13-continued

| PEx | Str |
|---|---|
| 81 | |
| 82 | |

TABLE 14

| PEx | Str |
|---|---|
| 83 | |
| 84 | |
| 85 | |

TABLE 14-continued

| PEx | Str |
|---|---|
| 86 | 2-(3-chloro-4-{[4-({[(tert-butoxycarbonyl)amino](tert-butoxycarbonylimino)methyl}amino)benzoyl]oxy}phenyl)propanoic acid structure |
| 87 | tert-butyl 3-(2-chloro-4-hydroxyphenyl)propanoate structure |
| 88 | tert-butyl 4-(2-chloro-4-methoxyphenyl)butanoate structure |
| 89 | 4-(2-chloro-4-{[4-({[(tert-butoxycarbonyl)amino](tert-butoxycarbonylimino)methyl}amino)benzoyl]oxy}phenyl)butanoic acid structure |

TABLE 15

| PEx | Str |
|---|---|
| 90 | structure containing tBuO2C-phenyl-C(O)-N(CH2CO2tBu)-(CH2)3-(2-chloro-4-hydroxyphenyl) |
| 91 | methyl 5-(2-chloro-4-hydroxyphenyl)pentanoate structure |
| 92 | 5-(3-chloro-4-{[4-({[(tert-butoxycarbonyl)amino](tert-butoxycarbonylimino)methyl}amino)benzoyl]oxy}phenyl)pentanoic acid structure |

TABLE 15-continued

| PEx | Str |
|---|---|
| 93 | (structure: 4-amino-3-chlorophenyl 4-(N,N'-di-Boc-guanidino)benzoate) |
| 94 | (structure: 2-(bromomethyl)-1,4-dichloro-5-methoxybenzene) |
| 95 | (structure: 2-(2,6-dichloro-4-methoxyphenyl)acetonitrile) |
| 96 | (structure: 2-(2,5-dichloro-4-methoxyphenyl)acetonitrile) |
| 97 | (structure: 2-(2,6-dichloro-4-methoxyphenyl)acetic acid) |

TABLE 16

| PEx | Str |
|---|---|
| 98 | (structure: 2-(2,5-dichloro-4-methoxyphenyl)acetic acid) |
| 99 | (structure: tert-butyl 2-methylquinoline-4-carboxylate) |
| 100 | (structure: tert-butyl 2-methylthiazole-4-carboxylate) |
| 101 | (structure: tert-butyl 2-fluoro-5-methylbenzoate) |
| 102 | (structure: tert-butyl 2-methoxy-5-methylbenzoate) |
| 103 | (structure: tert-butyl 3-cyano-5-fluorobenzoate) |

TABLE 16-continued

| PEx | Str |
|---|---|
| 104 | 5-methyl-thiophene-3-carboxylic acid tert-butyl ester |
| 105 | 5-methyl-thiophene-2-carboxylic acid tert-butyl ester |
| 106 | 6-hydroxy-quinoline-2-carboxylic acid benzyl ester |
| 107 | ethyl 3-(2-chloro-4-((2-(trimethylsilyl)ethoxy)methoxy)phenyl)but-2-enoate |

TABLE 17

| PEx | Str |
|---|---|
| 108 | tert-butyl (S)-2-amino-3-(4-(2-tert-butoxy-2-oxoethoxy)phenyl)propanoate |
| 109 | tert-butyl 2-((4-(tert-butoxycarbonyl)phenethyl)amino)acetate |
| 110 | tert-butyl 2-(((6-(tert-butoxycarbonyl)pyridin-2-yl)methyl)amino)acetate |
| 111 | tert-butyl 2-(((benzyloxycarbonyl)((6-(tert-butoxycarbonyl)pyridin-2-yl)methyl)amino))acetate |
| 112 | tert-butyl 2-((3-(2-chloro-4-hydroxyphenyl)propanamido)methyl)benzoate |
| 113 | tert-butyl 2-((N-(2-tert-butoxy-2-oxoethyl)-3-(4-benzyloxy-2-chlorophenyl)propanamido)methyl)benzoate |

TABLE 17-continued

| PEx | Str |
|---|---|
| 114 | 2-(4-((4-(N,N'-bis-Boc-guanidino)benzoyl)oxy)-3-methoxyphenyl)acetic acid |
| 115 | 2-(4-((4-(N,N'-bis-Boc-guanidino)benzoyl)oxy)-3-fluorophenyl)acetic acid |
| 116 | 2-(4-((4-(N,N'-bis-Boc-guanidino)benzoyl)oxy)-2-phenylphenyl)acetic acid |

TABLE 18

| PEx | Str |
|---|---|
| 117 | 2-(4-((4-(N,N'-bis-Boc-guanidino)benzoyl)oxy)-2,6-difluorophenyl)acetic acid |
| 118 | 2-(4-((4-(N,N'-bis-Boc-guanidino)benzoyl)oxy)-2-(trifluoromethyl)phenyl)acetic acid |

TABLE 18-continued
| PEx | Str |
|---|---|
| 119 | 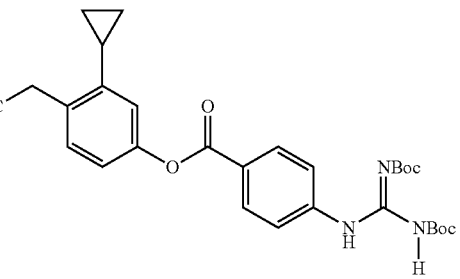 |
| 120 | 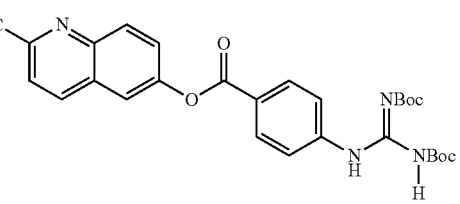 |
| 121 | 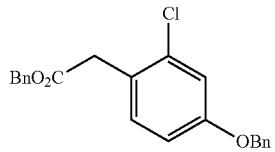 |
TABLE 18-continued
| PEx | Str |
|---|---|
| 122 | 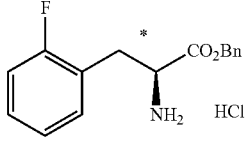 |
| 123 | 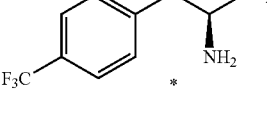 |
| 124 | 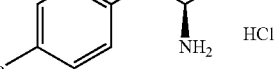 |
TABLE 19
| PEx | Str |
|---|---|
| 125 | 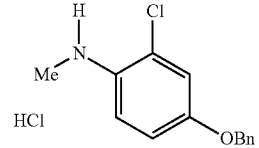 [SMILES: Cl ; CNc1ccc(OCc2ccccc2)cc1Cl] |
| 126 | 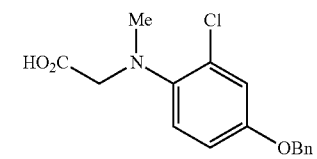 [SMILES: CN(CC(=O)O)c1ccc(OCc2ccccc2)cc1Cl] |
| 127 | 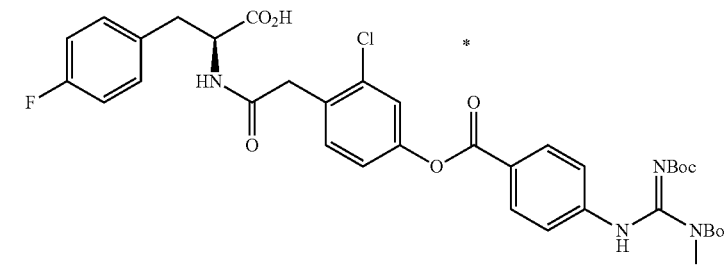 |

TABLE 19-continued

| PEx | Str |
|---|---|
| 128 | |
| 129 | |
| 130 | |

TABLE 20

| PEx | Str |
|---|---|
| 131 | |
| 132 | |

TABLE 20-continued

| PEx | Str |
|---|---|
| 133 | (structure) |
| 134 | (structure) |
| 135 | (structure) |
| 136 | (structure) |

TABLE 21

| PEx | Str |
|---|---|
| 137 | (structure) |
| 138 | (structure) |
| 139 | (structure) |
| 140 | (structure) |
| 141 | (structure) |

TABLE 21-continued
| PEx | Str |
|---|---|
| 142 | 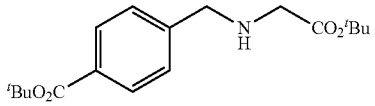 |
| 143 | 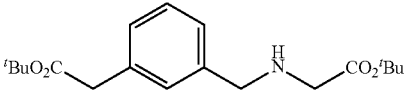 [SMILES: CC(C)(C)OC(=O)CNCc1cccc(CC(=O)OC(C)(C)C)c1] |
| 144 | 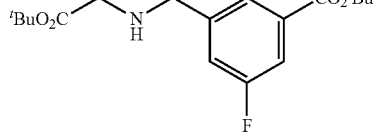 |
| 145 | 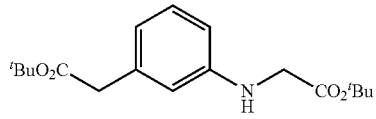 [SMILES: CC(C)(C)OC(=O)CNc1cccc(CC(=O)OC(C)(C)C)c1] |
TABLE 22
| PEx | Str |
|---|---|
| 146 | 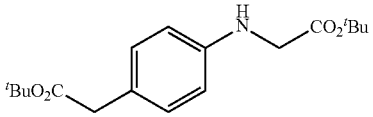 [SMILES: CC(C)(C)OC(=O)CNc1ccc(CC(=O)OC(C)(C)C)cc1] |
| 147 | 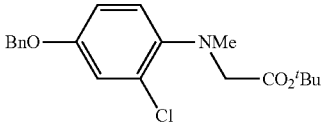 |
| 148 | 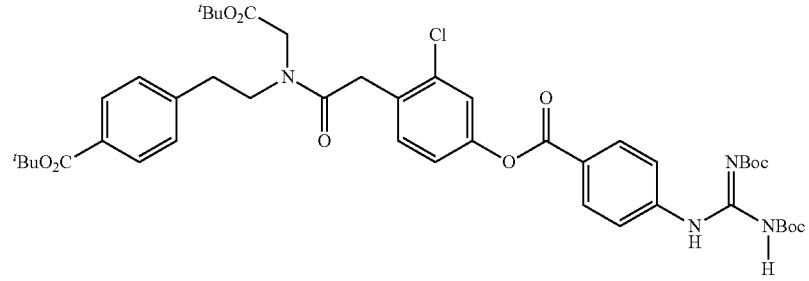 |
| 149 | 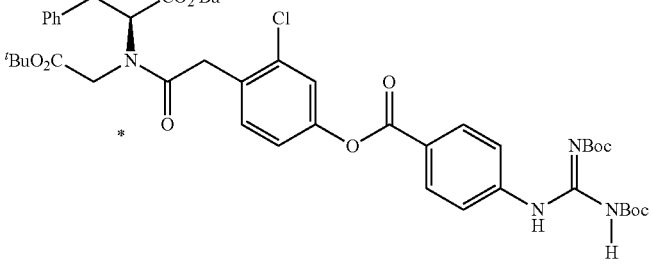 |
| 150 | 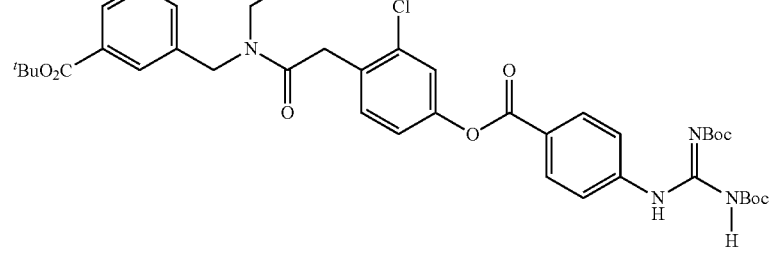 |

TABLE 22-continued
| PEx | Str |
|---|---|
| 151 | 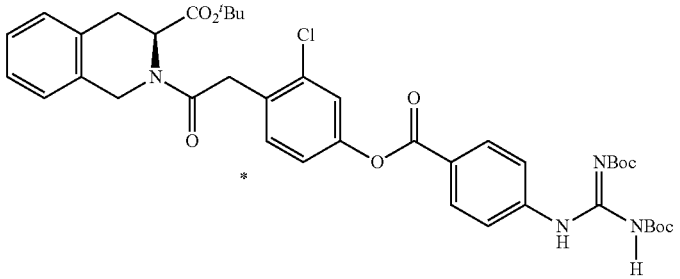 |
TABLE 23
| PEx | Str |
|---|---|
| 152 | 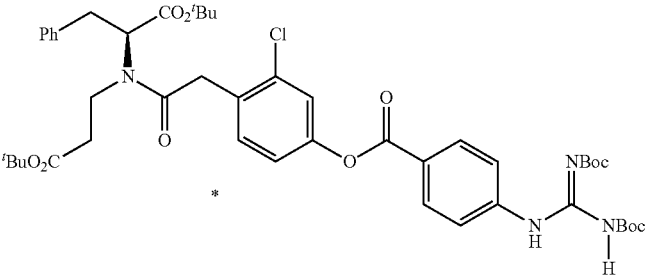 |
| 153 | 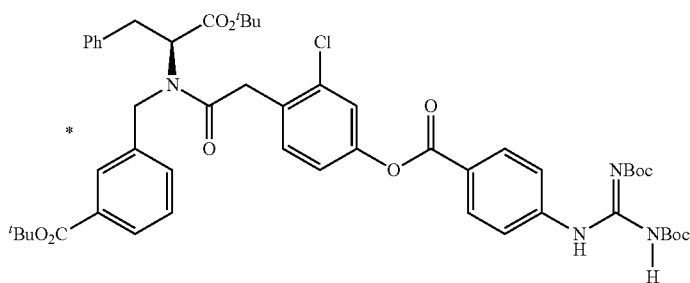 |
| 154 | 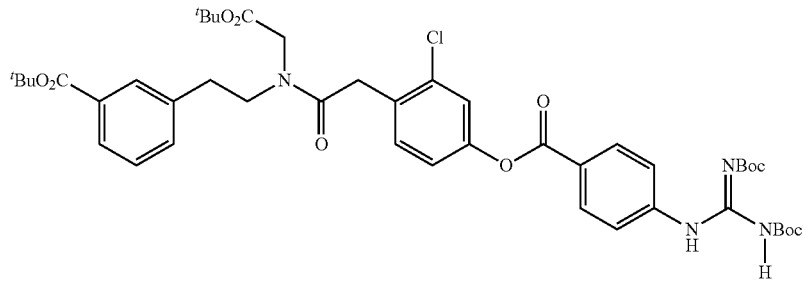 |

TABLE 23-continued

| PEx | Str |
|---|---|
| 155 | (structure) |
| 156 | (structure) |

TABLE 24

| PEx | Str |
|---|---|
| 157 | (structure) |
| 158 | (structure) |
| 159 | (structure) |

TABLE 24-continued
| PEx | Str |
|---|---|
| 160 | 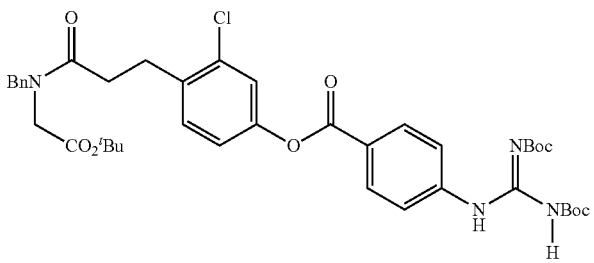 |
| 161 | 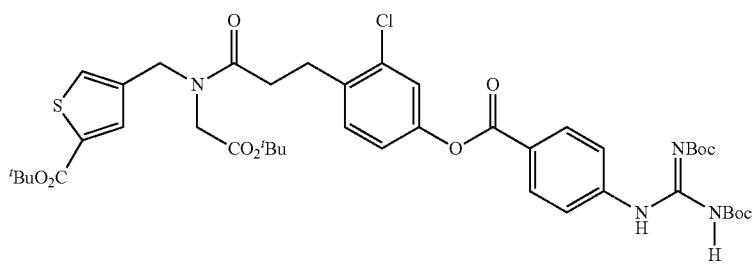 |
| 162 | 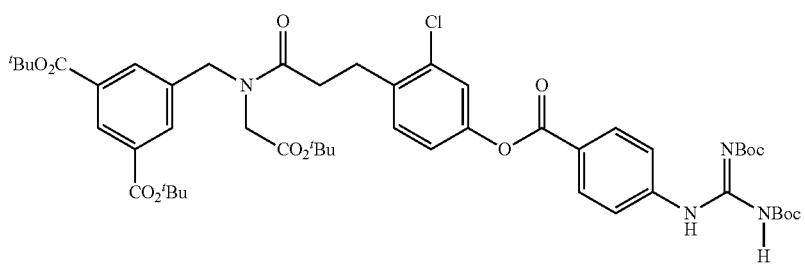 |
TABLE 25
| PEx | Str |
|---|---|
| 163 | 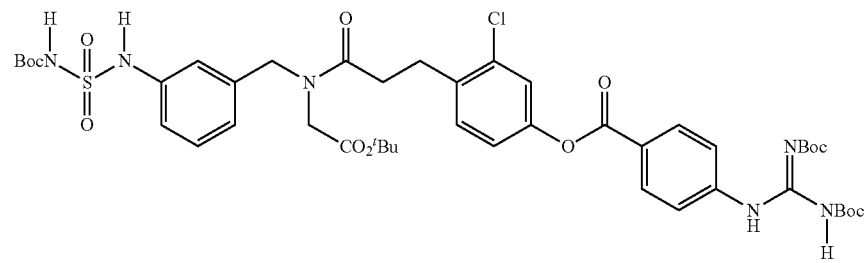 |
| 164 | 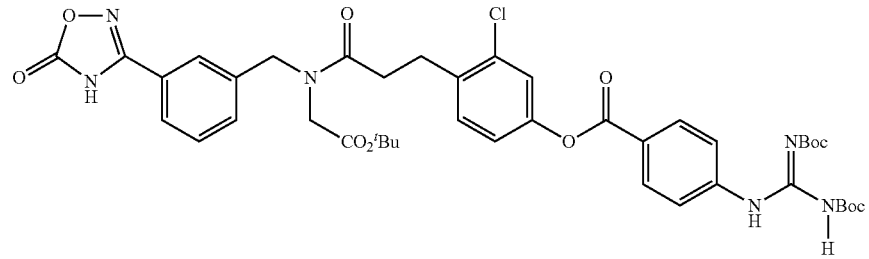 |

TABLE 25-continued
| PEx | Str |
|---|---|
| 165 | 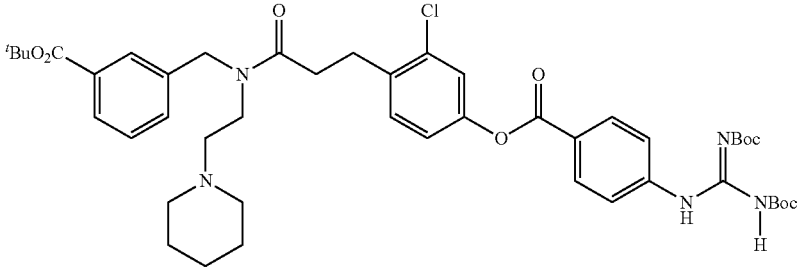 |
| 166 | 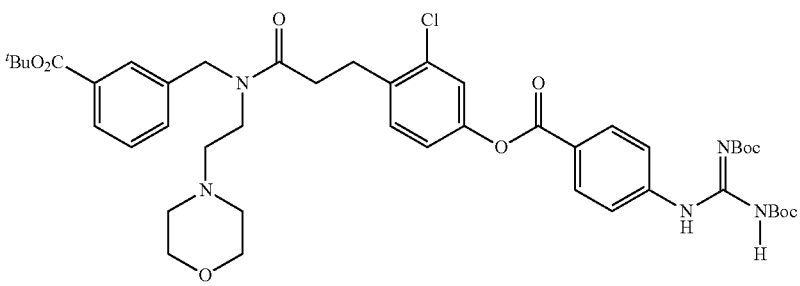 |
| 167 | 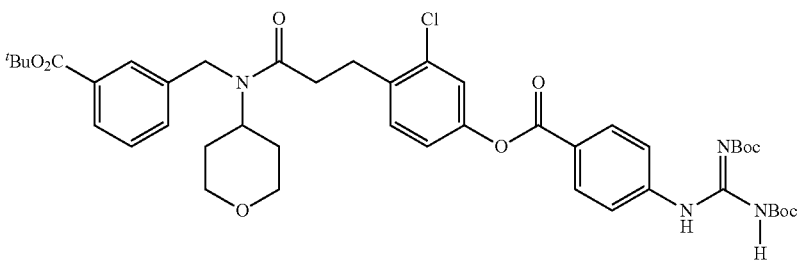 |
| 168 | 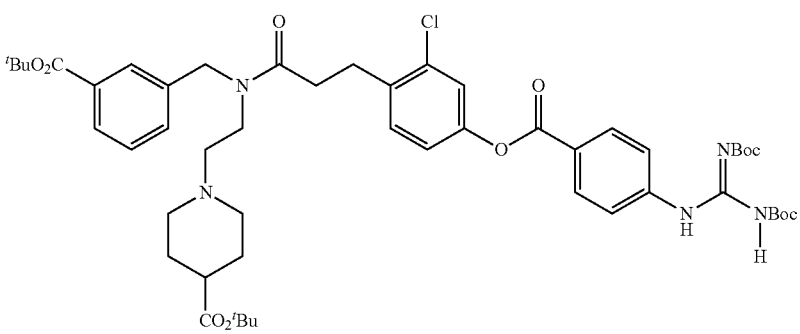 |
TABLE 26
| PEx | Str |
|---|---|
| 169 | 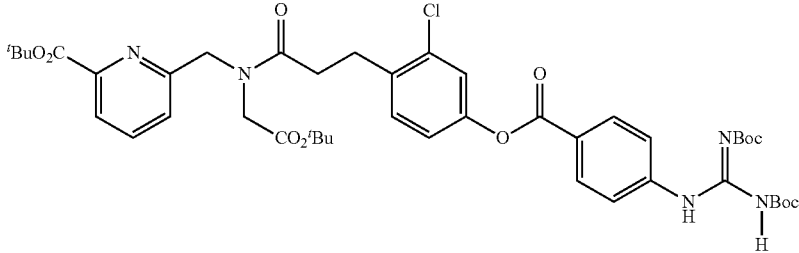 |

TABLE 26-continued
| PEx | Str |
|---|---|
| 170 | 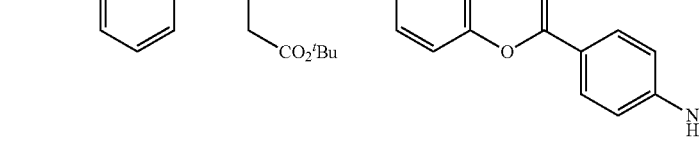 |
| 171 | 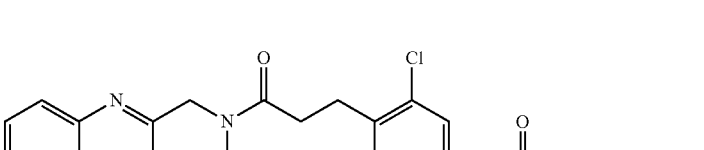 |
| 172 | 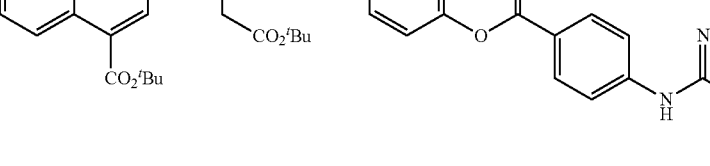 |
| 173 | 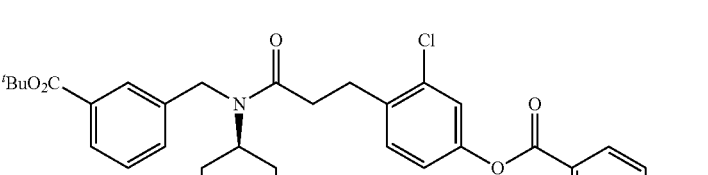 |
| 174 | 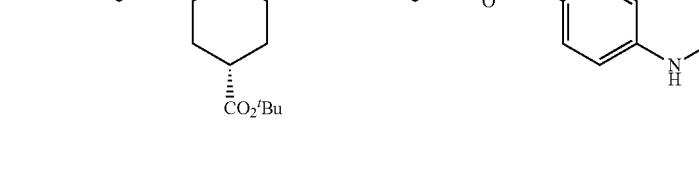 |

TABLE 27

| PEx | Str |
|---|---|
| 175 | (structure) |
| 176 | (structure) |
| 177 | (structure) |
| 178 | (structure) |
| 179 | (structure) |
| 180 | (structure) |

TABLE 28
| PEx | Str |
|---|---|
| 181 | 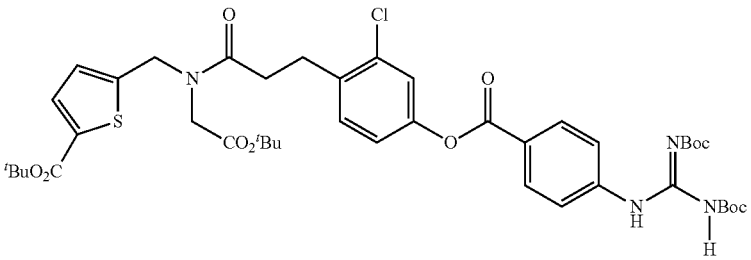 |
| 182 | 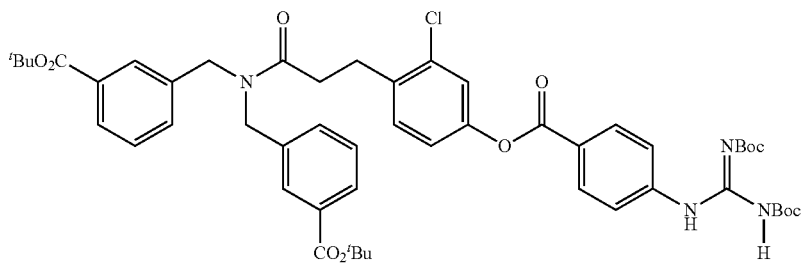 |
| 183 | 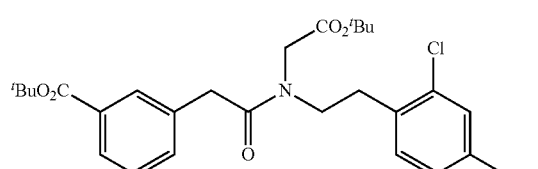 |
| 184 | 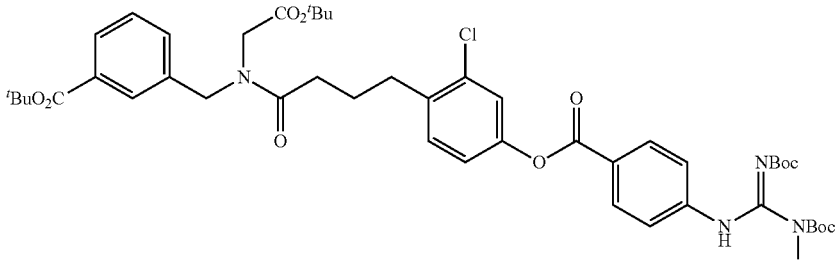 |
| 185 | 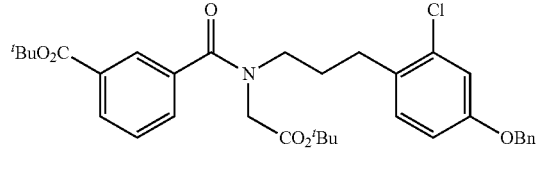 [SMILES: CC(C)(C)OC(=O)CN(CCCc1ccc(OCc2ccccc2)cc1Cl)C(=O)c1cccc(C(=O)OC(C)(C)C)c1] |
| 186 | 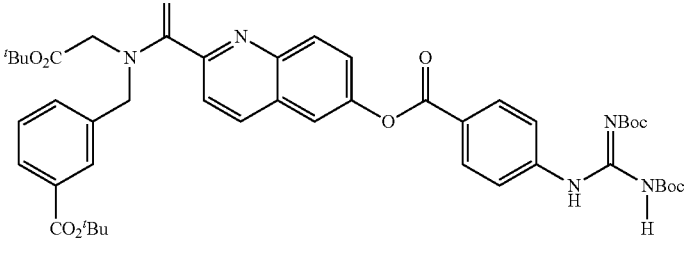 |

TABLE 29

| PEx | Str |
|---|---|
| 187 | (structure) |
| 188 | (structure) |
| 189 | (structure) |
| 190 | (structure) |
| 191 | (structure) |
| 192 | (structure) |
| 193 | (structure) |
| 194 | (structure) |
| 195 | (structure) |

TABLE 30
| PEx | Str |
|---|---|
| 196 | 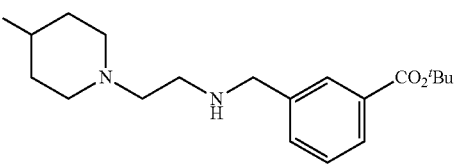 |
| 197 | 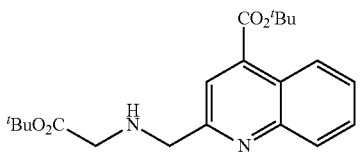 [SMILES: CC(C)(C)OC(=O)CNCc1cc(C(=O)OC(C)(C)C)c2ccccc2n1] |
| 198 | 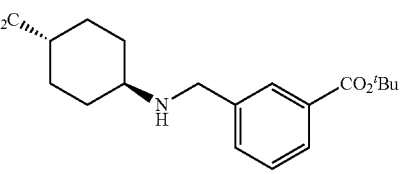 |
| 199 | 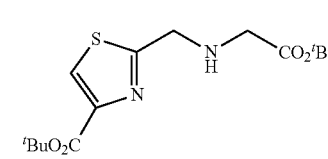 |
TABLE 30-continued
| PEx | Str |
|---|---|
| 200 | 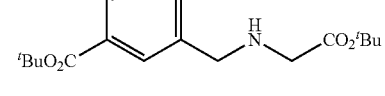 |
| 201 | 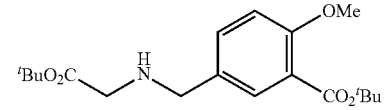 [SMILES: COc1ccc(CNCC(=O)OC(C)(C)C)cc1C(=O)OC(C)(C)C] |
| 202 | 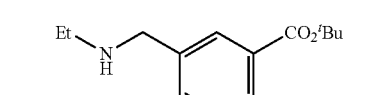 |
| 203 | 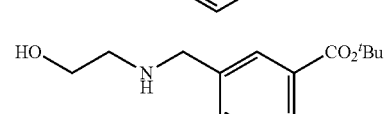 |
| 204 | 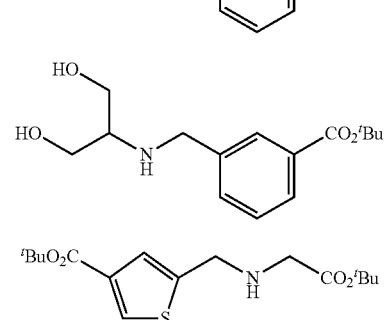 |
| 205 | 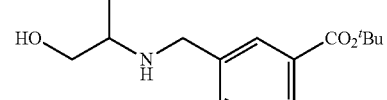 |
TABLE 31
| PEx | Str |
|---|---|
| 206 | 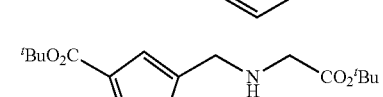 |
| 207 | 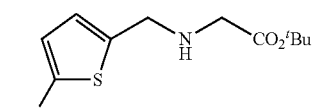 |
| 208 | 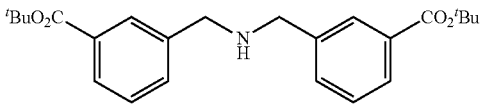 [SMILES: CC(C)(C)OC(=O)c1cccc(CNCc2cccc(C(=O)OC(C)(C)C)c2)c1] |
| 209 | 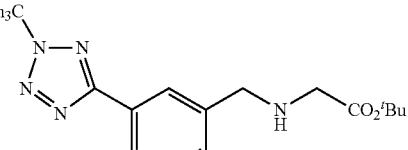 |

TABLE 31-continued

| PEx | Str |
|---|---|
| 210 | (structure) |
| 211 | (structure) |
| 212 | (structure) |

TABLE 32

| PEx | Str |
|---|---|
| 213 | (structure) |
| 214 | (structure) |
| 215 | (structure) |
| 216 | (structure) |

TABLE 32-continued

| PEx | Str |
|---|---|
| 5 | (structure) |

TABLE 33

| PEx | Str |
|---|---|
| 218 | (structure) |
| 219 | (structure) |
| 220 | (structure) |
| 221 | (structure) |
| 222 | (structure) |

TABLE 33-continued

| PEx | Str |
|---|---|
| 223 | (structure) |

TABLE 34

| PEx | Str |
|---|---|
| 224 | (structure) |
| 225 | (structure) |
| 226 | (structure) |
| 227 | (structure) |

TABLE 34-continued
| PEx | Str |
|---|---|
| 228 | 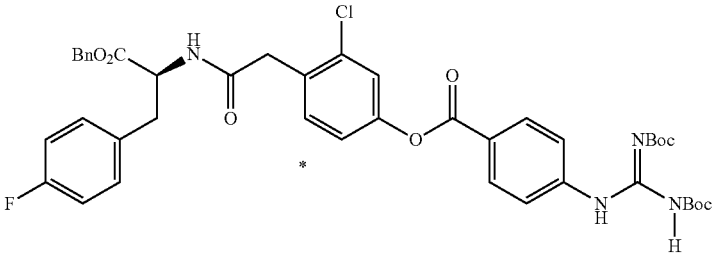 |
TABLE 35
| PEx | Str |
|---|---|
| 229 | 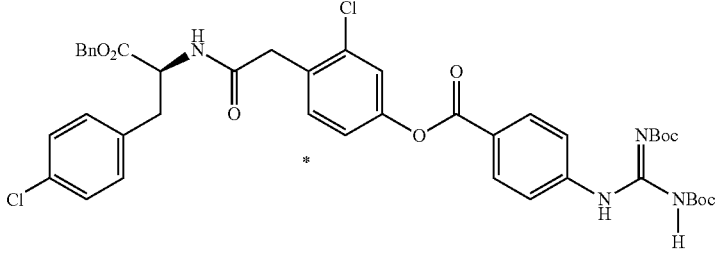 |
| 230 | 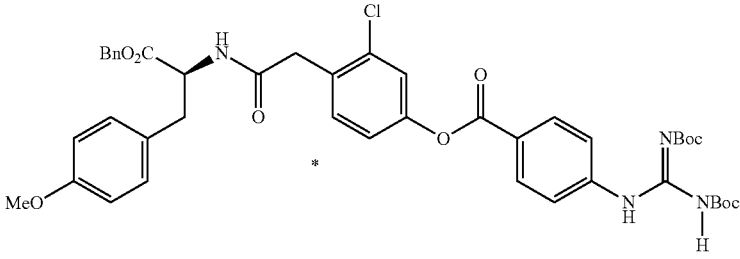 |
| 231 | 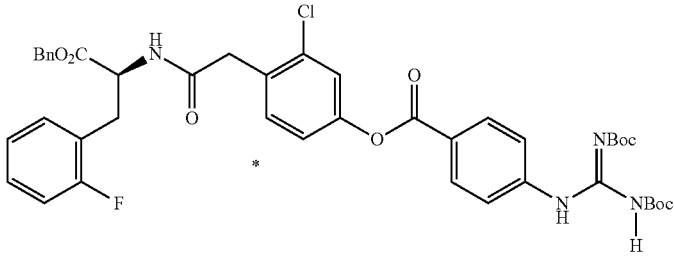 |
| 232 | 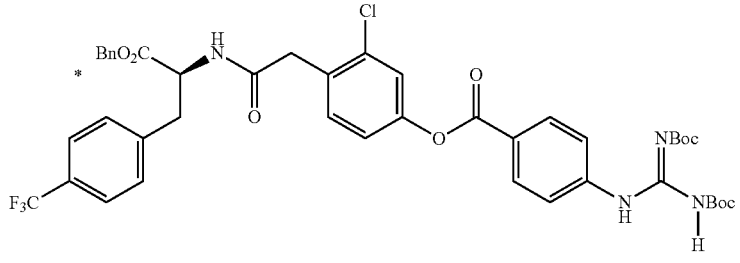 |

TABLE 35-continued
| PEx | Str |
|---|---|
| 233 | 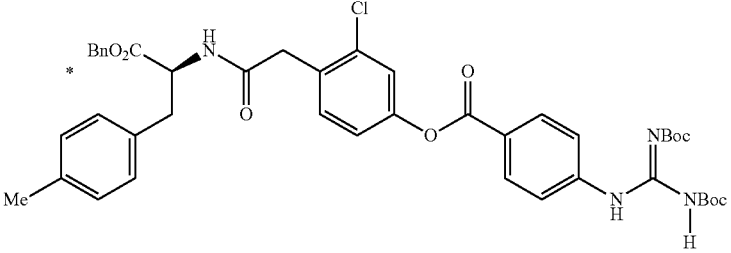 |
TABLE 36
| PEx | Str |
|---|---|
| 234 | 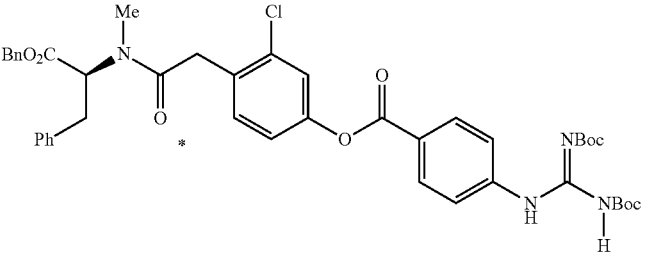 |
| 235 | 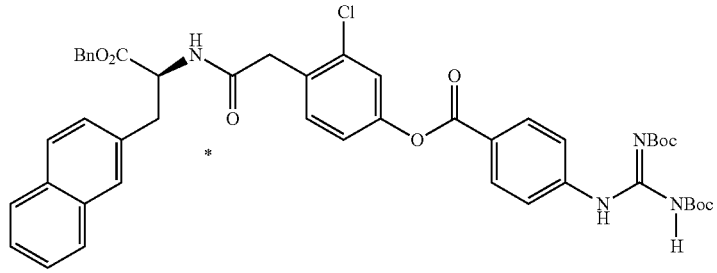 |
| 236 | 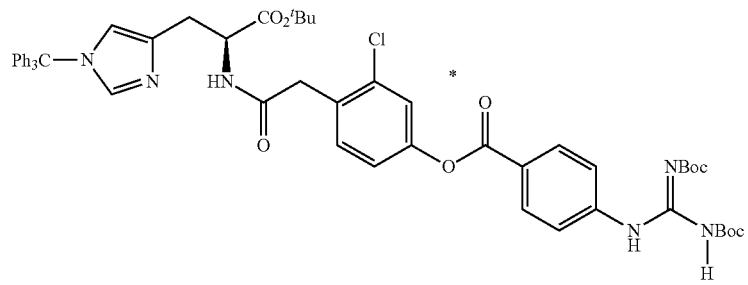 |
| 237 | 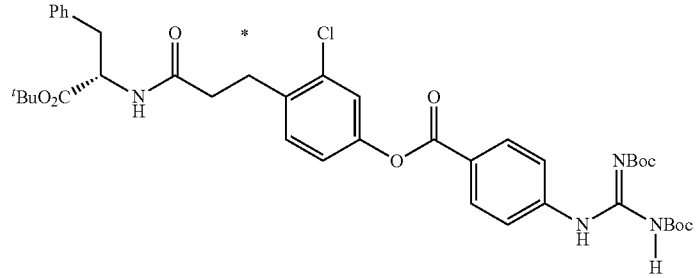 |

TABLE 36-continued

| PEx | Str |
|---|---|
| 238 | (structure) |

TABLE 37

| PEx | Str |
|---|---|
| 239 | (structure) |
| 240 | (structure) |
| 241 | (structure) |
| 242 | (structure) |

TABLE 37-continued

| PEx | Str |
|---|---|
| 243 | (structure: tBuO2C-CH(Ph)-NH-C(=O)-CH2-CH2-[Ar-Cl]-O-C(=O)-[Ar]-NH-C(=NBoc)-NHBoc, with * marker) |

TABLE 38

| PEx | Str |
|---|---|
| 244 | (structure: tBuO2C-CH2-O-[Ar]-CH2-CH(CO2tBu)-NH-C(=O)-CH2-CH2-[Ar-Cl]-O-C(=O)-[Ar]-NH-C(=NBoc)-NHBoc, with * marker) |
| 245 | (structure: HO-[Ar-Cl]-CH2-CH2-C(=O)-NH-CH2-[Ar]-CO2Me) |
| 246 | (structure: tBuO2C-CH2-NH-C(=O)-CH2-CH2-[Ar-Cl]-OBn) |
| 247 | (structure: Ph-CH2-CH(CO2tBu)-NH-C(=O)-CH2-CH2-CH2-[Ar-Cl]-O-C(=O)-[Ar]-NH-C(=NBoc)-NHBoc, with * marker) |

TABLE 38-continued

| PEx | Str |
|---|---|
| 248 | |
| 249 | |

TABLE 39

| PEx | Str |
|---|---|
| 250 | |
| 251 | |
| 252 | |

TABLE 39-continued
| PEx | Str |
|---|---|
| 253 | |
| 254 | |
| 255 | |
TABLE 40
| PEx | Str |
|---|---|
| 256 |  |
| 257 |  |
| 258 |  |
| 259 | |
| 260 | |
TABLE 40-continued
| PEx | Str |
|---|---|
| 261 | |
| 262 | |
| 263 | |
| 264 | |
| 265 | |

TABLE 40-continued

| PEx | Str |
|---|---|
| 266 | BnO₂C-C₆H₃(CF₃)-OH (4-hydroxy-2-trifluoromethylphenyl acetic acid benzyl ester) |

TABLE 41

| PEx | Str |
|---|---|
| 267 | BnO₂C-C₆H₃(Cl)-OH (3-chloro-4-hydroxyphenyl acetic acid benzyl ester) |
| 268 | BnO₂C-C₆H₃(Br)-OH (2-bromo-4-hydroxyphenyl acetic acid benzyl ester) |
| 269 | (S)-N-Boc-3-fluorophenylalanine benzyl ester * |
| 270 | (S)-N-Boc-4-trifluoromethylphenylalanine benzyl ester * |

TABLE 41-continued

| PEx | Str |
|---|---|
| 271 | BnO₂C-CH(Me)-C₆H₃(Cl)-OH |
| 272 | tBuO₂C-CH₂CH₂-C₆H₃(Cl)-OBn |
| 273 | BnO₂C-CH₂-C₆H₃(Br)-OBn |
| 274 | BnO₂C-(CH₂)₃-C₆H₃(Cl)-OH |
| 275 | BnO₂C-(CH₂)₄-C₆H₃(Cl)-OH |
| 276 | Boc-NH-C₆H₃(Cl)-OBn |

TABLE 42

| PEx | Str |
|---|---|
| 277 | tBuO₂C-CH₂-C₆H₄-N(CH₂CO₂tBu)-C(O)-CH₂CH₂-C₆H₃(Cl)-O-C(O)-C₆H₄-NH-C(=NBoc)-NHBoc |

TABLE 42-continued

| PEx | Str |
|---|---|
| 278 | (structure) |
| 279 | (structure) |
| 280 | (structure) |
| 281 | (structure) |
| 282 | (structure) |
| 283 | (structure) |

TABLE 43

| PEx | Str |
|---|---|
| 284 | (structure) |

TABLE 43-continued

| PEx | Str |
|---|---|
| 285 | (structure) |
| 286 | (structure) |
| 287 | (structure) |
| 288 | (structure) |
| 289 | (structure) |
| 290 | (structure) |

TABLE 44
| PEx | Str |
|---|---|
| 291 | 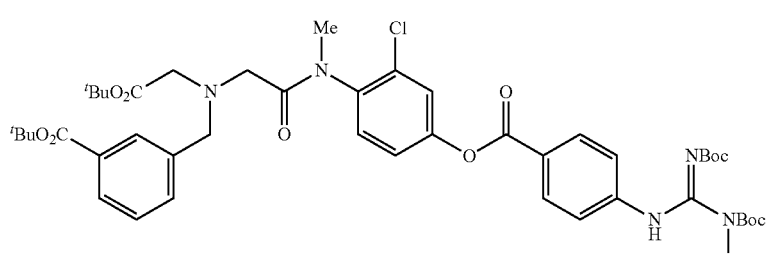 |
| 292 | 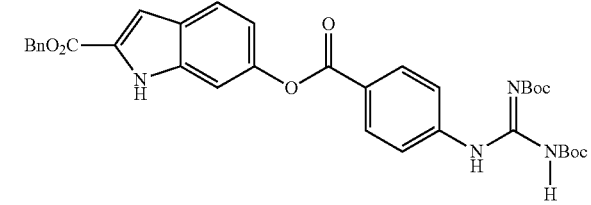 |
| 293 | 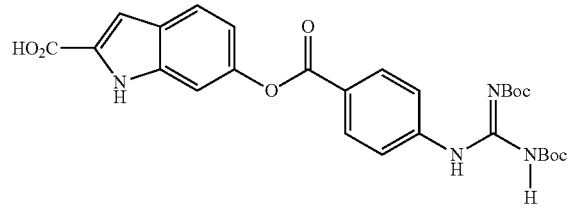 |
| 294 | 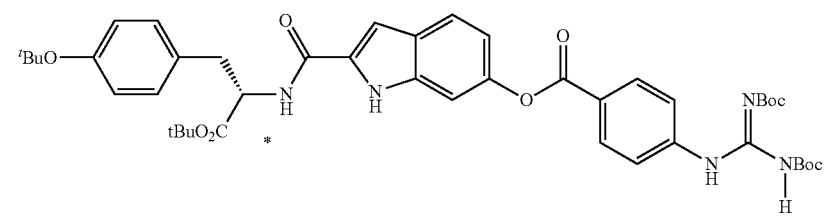 |
| 295 | 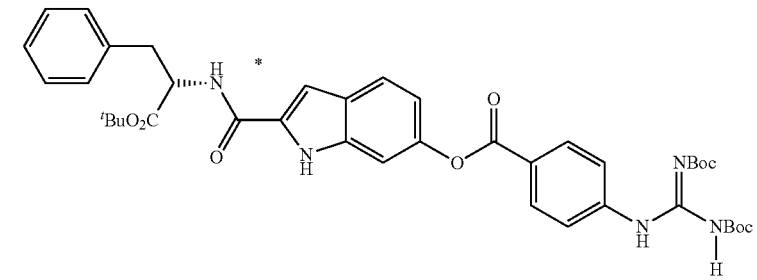 |
| 296 | 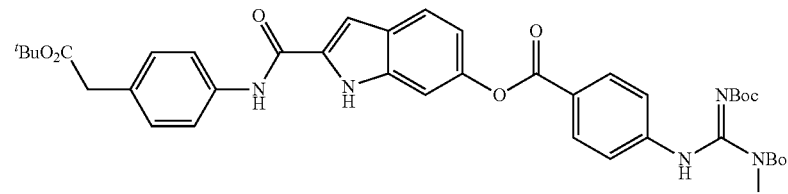 |

TABLE 45
| PEx | Str |
|---|---|
| 297 | 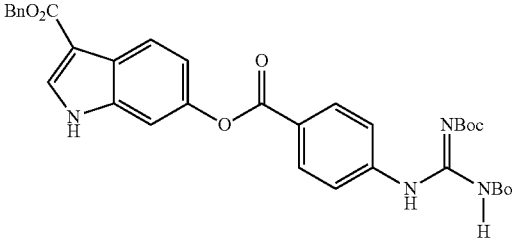 |
| 298 | 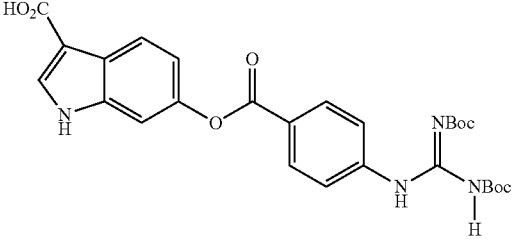 |
| 299 | 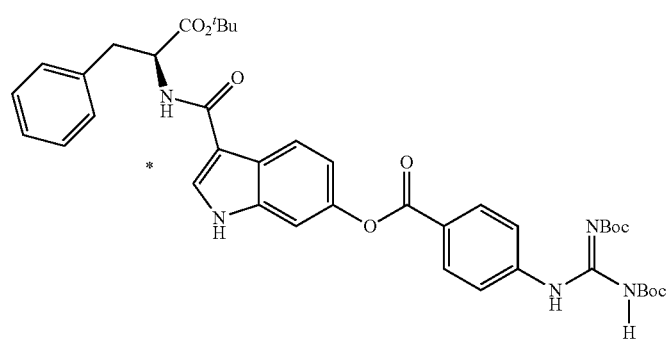 |
| 300 | 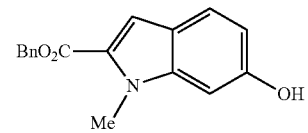 |
| 301 | 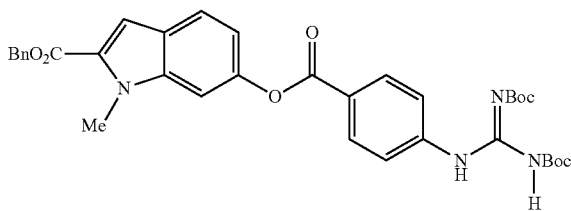 |
| 302 | 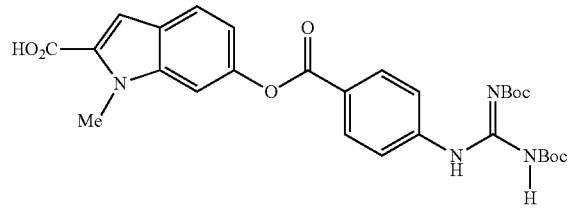 |

TABLE 46

| PEx | Str |
|---|---|
| 303 | (chemical structure) |
| 304 | (chemical structure) |
| 305 | (chemical structure) |
| 306 | (chemical structure) |
| 307 | (chemical structure) |
| 308 | (chemical structure) |

TABLE 47
| PEx | Str |
|---|---|
| 309 | 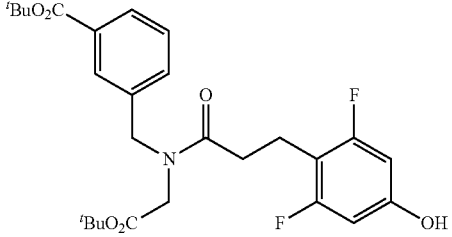 [SMILES: CC(C)(C)OC(=O)CN(Cc1cccc(C(=O)OC(C)(C)C)c1)C(=O)CCc1c(F)cc(O)cc1F] |
| 310 | 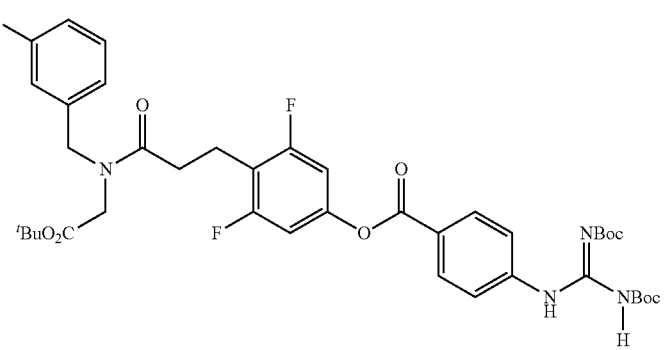 |
| 311 | 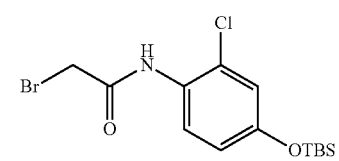 [SMILES: CC(C)(C)[Si](C)(C)Oc1ccc(NC(=O)CBr)c(Cl)c1] |
| 312 | 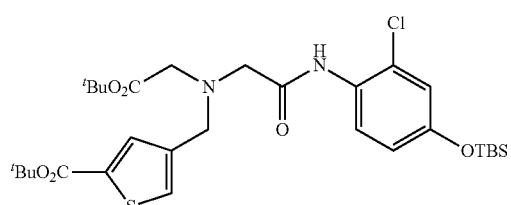 |
| 313 | 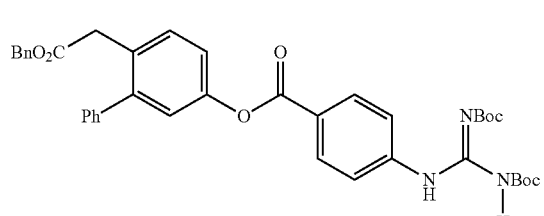 |
| 314 | 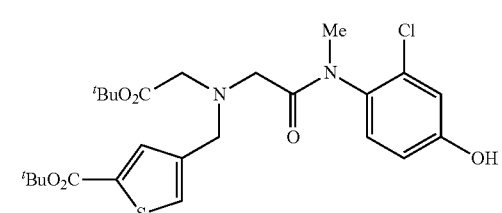 |

TABLE 48

| PEx | Str |
|---|---|
| 315 | (structure) |
| 316 | (structure) |
| 317 | (structure) |
| 318 | (structure) |
| 319 | (structure) |
| 320 | (structure) |

TABLE 49

| PEx | Str |
|---|---|
| 321 | (structure) |
| 322 | (structure) |
| 323 | (structure) |
| 324 | (structure) |
| 325 | (structure) |
| 326 | (structure) |

TABLE 50

| PEx | Str |
|---|---|
| 327 | (structure) |
| 328 | (structure) |
| 329 | (structure) |
| 330 | (structure) |
| 331 | (structure) |
| 332 | (structure) |

TABLE 50-continued

| PEx | Str |
|---|---|
| 333 | *tBuO₂C-benzothiophene-CH₂Br* |

TABLE 51

| PEx | Str |
|---|---|
| 334 | *tBuO₂C-benzothiophene-CH₂-NH-CH₂-CO₂tBu* |
| 335 | *tBuO₂C-CH₂-N(—C(O)-quinoline-O-C(O)-C₆H₄-NH-C(=NBoc)NHBoc)-CH₂-benzothiophene-CO₂tBu* |
| 336 | *Ph-CH₂-CH(CO₂tBu)-NH-C(O)-CH₂-(3,2-diCl-C₆H₂)-O-C(O)-C₆H₄-NH-C(=NBoc)NHBoc* (with * stereocenter) |
| 337 | *tBuO₂C-CH₂-N(-C(O)-C₆H₄-CO₂tBu)-CH₂-quinoline-O-C(O)-C₆H₄-NH-C(=NBoc)NHBoc* |
| 338 | *tBuO₂C-C₆H₄-CH₂-CH(CO₂tBu)-NH-C(O)-CH₂CH₂-(2-Cl-C₆H₃)-O-C(O)-C₆H₄-NH-C(=NBoc)NHBoc* (with * stereocenter) |

TABLE 51-continued

| PEx | Str |
|---|---|
| 339 | |

TABLE 52

| PEx | Str |
|---|---|
| 340 | |
| 341 | |
| 342 | |
| 343 | |

TABLE 52-continued

| PEx | Str |
|---|---|
| 344 | (structure) |
| 345 | (structure) |

TABLE 53

| PEx | Str |
|---|---|
| 346 | (structure) |
| 347 | (structure) |
| 348 | (structure) |
| 349 | (structure) |

TABLE 53-continued
| PEx | Str |
|---|---|
| 350 | 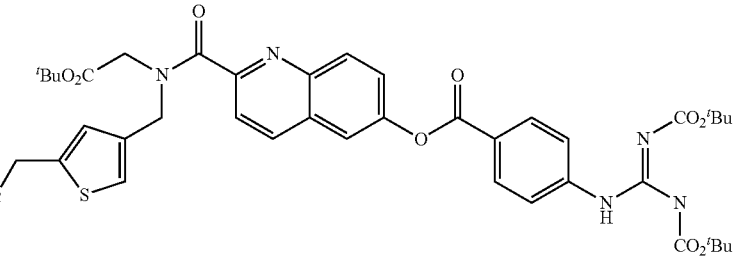 |
| 351 | 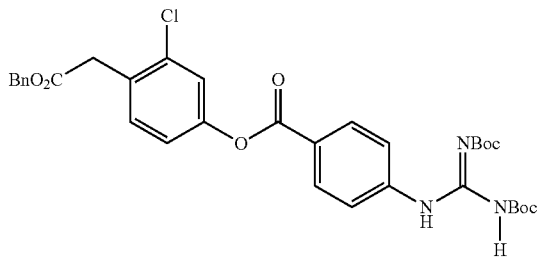 |
| 352 | 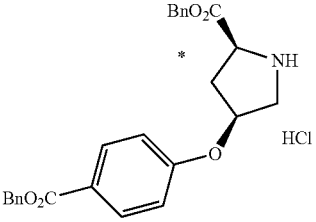 |
TABLE 54
| PEx | Str |
|---|---|
| 353 | 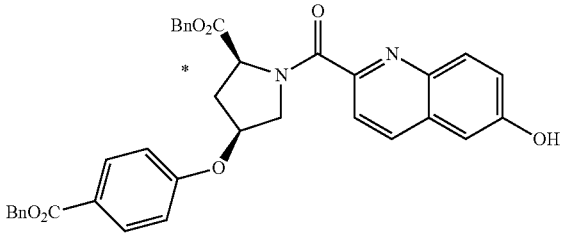 |
| 354 | 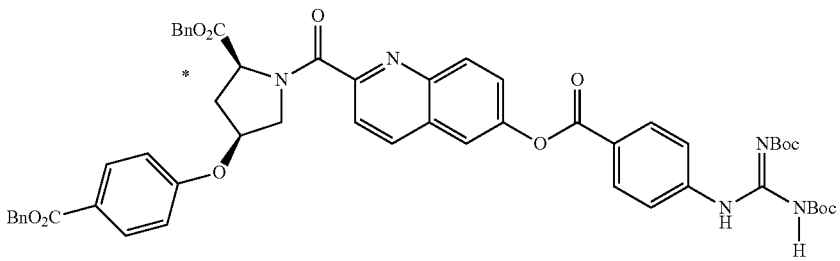 |

TABLE 54-continued

| PEx | Str |
|---|---|
| 355 | |
| 356 | |
| 357 | |
| 358 | |
| 359 | |

TABLE 55

| PEx | Str |
|---|---|
| 360 | (structure) |
| 361 | (structure) |
| 362 | (structure) |
| 363 | (structure) |
| 364 | (structure) |
| 365 | (structure) |
| 366 | (structure) |
| 367 | (structure) |

TABLE 56

| PEx | Str |
|---|---|
| 368 | |
| 369 | |
| 370 | |
| 371 | |
| 372 | |
| 373 | |

TABLE 56-continued

| PEx | Str |
|---|---|
| 374 | (structure) |

TABLE 57

| PEx | Str |
|---|---|
| 375 | (structure) |
| 376 | (structure) |
| 377 | (structure) |
| 378 | (structure) |
| 379 | (structure) |

TABLE 57-continued

| PEx | Str |
| --- | --- |
| 380 | (structure) |
| 381 | (structure) |

TABLE 58

| PEx | Str |
| --- | --- |
| 382 | (structure) |
| 383 | (structure) |
| 384 | (structure) |
| 385 | (structure) |

TABLE 58-continued

| PEx | Str |
|---|---|
| 386 | [chemical structure] |
| 387 | [chemical structure] |
| 388 | [chemical structure] |

TABLE 59

| PEx | Str |
|---|---|
| 389 | [chemical structure] |
| 390 | [chemical structure] |
| 391 | [chemical structure] |

TABLE 59-continued

| PEx | Str |
|---|---|
| 392 | (structure: tBuO2C-CH2-N(CH2-3-(CO2tBu)phenyl)-C(O)-CH(Me)-CH2-[2-Cl,4-O-C(O)-C6H4-4-NH-C(=NBoc)NHBoc phenyl]) |
| 393 | (structure: tBuO2C-CH2-N(CH2-[5-(CO2tBu)thiophen-3-yl])-C(O)-CH(Me)-CH2-[2-Cl,4-O-C(O)-C6H4-4-NH-C(=NBoc)NHBoc phenyl]) |
| 394 | (structure: tBuO2C-CH2-[3-(CO2tBu)phenyl]-CH2-C(O)-N(CH2CO2tBu)-CH2CH2-[2-Cl,4-O-C(O)-C6H4-4-NH-C(=NBoc)NHBoc phenyl]) |

TABLE 60

| PEx | Str |
|---|---|
| 395 | (structure: BnO2C-(CH2)3-[2-Cl,4-O-C(O)-C6H4-4-NH-C(=NBoc)NHBoc phenyl]) |
| 396 | (structure: tBuO2C-CH2-NH-CH2-[2-(6-OBn)quinolinyl]) |

TABLE 61

| PEx | PSyn | Data |
|---|---|---|
| 1 | 1 | ESI+: 271 |
| 2 | 2 | ESI+: 632 |
| 3 | 3 | ESI+: 542 |
| 4 | 4 | NMR1: 1.24(9H, s), 1.31(9H, s), 1.43(9H, s), 1.52(9H, s), 1.69-1.81(2H, m), 2.12(2H, t, J = 7.6 Hz), 2.46-2.56(2H, m), 2.76-2.94(2H, m), 4.31-4.40(1H, m), 6.83-6.89(2H, m), 7.05-7.25(7H, m), 7.81(2H, d, J = 8.4 Hz), 8.09(2H, d, J = 8.4 Hz), 8.20 (1H, d, J = 7.6 Hz), 10.24(1H, s), 11.22(1H, s) |
| 5 | 5 | ESI+: 319 |
| 6 | 6 | ESI−: 219 |
| 7 | 7 | EI: 434, 436 |
| 8 | 8 | ESI+: 397 |
| 9 | 9 | ESI+: 283 |
| 10 | 10 | ESI+: 548 |
| 11 | 11 | EI: 206 |
| 12 | 12 | EI: 268 |
| 13 | 13 | EI: 268 |
| 14 | 14 | EI: 215 |
| 15 | 15 | ESI−: 233 |
| 16 | 16 | ESI+: 456 |
| 17 | 17 | ESI+: 322 |
| 18 | 18 | ESI+: 378[M + Na]+ |
| 19 | 19 | ESI+: 492[M + Na]+ |
| 20 | 20 | ESI+: 277 |
| 21 | 21 | ESI+: 274 |
| 22 | 22 | ESI+: 713 |
| 23 | 23 | ESI+: 350 |
| 24 | 24 | ESI+: 412 |
| 25 | 25 | ESI+: 336 |

TABLE 61-continued

| PEx | PSyn | Data |
|---|---|---|
| 26 | 26 | ESI+: 765 |
| 27 | 27 | ESI+: 289 |
| 28 | 28 | ESI+: 322 |
| 29 | 29 | ESI+: 385[M + Na]+ |
| 30 | 30 | ESI+: 333 |
| 31 | 31 | ESI−: 510 |
| 32 | 32 | ESI+: 416 |
| 33 | 33 | ESI+: 376 |
| 34 | 34 | ESI−: 400 |
| 35 | 35 | ESI+: 295 |
| 36 | 36 | ESI+: 429 |
| 37 | 37 | ESI+: 401 |
| 38 | 38 | ESI+: 322, 324 |
| 39 | 39 | ESI+: 226 |
| 40 | 40 | ESI+: 384 |
| 41 | 41 | ESI+: 865, 867 |
| 42 | 42 | ESI+: 462 |
| 43 | 43 | ESI+: 334 |
| 44 | 44 | ESI−: 289 |
| 45 | 45 | EI: 262, 264 |
| 46 | 46 | EI: 260, 262 |
| 47 | 47 | EI: 282, 284 |
| 48 | 48 | ESI+: 215 |
| 49 | 49 | EI: 228, 230 |
| 50 | 50 | ESI+: 277 |
| 51 | 51 | ESI+: 278 |
| 52 | 52 | ESI+: 519, 521 |
| 53 | 53 | ESI+: 866, 868 |
| 54 | 54 | ESI+: 348 |
| 55 | 55 | ESI+: 408, 410 |
| 56 | 56 | ESI+: 364, 366 |
| 57 | 57 | ESI+: 649, 651 |
| 58 | 58 | ESI+: 519, 521 |
| 59 | 59 | ESI+: 514 |
| 60 | 60 | ESI+: 268 |
| 61 | 61 | ESI+: 268 |
| 62 | 62 | APCI/ESI+: 342 |
| 63 | 63 | EI: 203 |
| 64 | 64 | ESI+: 639, 641 |
| 65 | 65 | APCI/ESI+: 398 |
| 66 | 66 | ESI+: 352 |
| 67 | 67 | ESI+: 336 |
| 68 | 68 | APCI/ESI+: 271 |
| 69-1 | 69 | ESI+: 865 |
| 69-2 | 69 | ESI+: 865 |
| 70 | 70 | ESI+: 336 |
| 71 | 71 | ESI+: 376 |

TABLE 62

| PEx | PSyn | Data |
|---|---|---|
| 72 | 72 | NMR2: 1.33-1.49(9H, m), 2.39-2.58(2H, m), 3.62-3.89(2H, m), 4.43-4.67(1H, m), 4.91-4.99(1H, m), 5.01-5.27(2H, m), 5.34(2H, s), 6.71(2H, d, J = 8.4 Hz), 7.21-7.47(10H, m), 7.94-8.02(2H, m) |
| 73 | 73 | APCI/ESI+: 272 |
| 74 | 74 | ESI+: 361[M + Na]+ |
| 75 | 75 | NMR2: 1.14(3H, t, J = 7.6 Hz), 1.61(18H, s), 2.69(2H, q, J = 7.6 Hz), 3.87(2H, s), 8.07-8.10(2H, m), 8.44-8.47(1H, m) |
| 76 | 76 | CI+: 372 |
| 77 | 77 | ESI−: 301 |
| 78 | 78 | ESI+: 370 |
| 79 | 79 | ESI+: 264 |
| 80 | 80 | ESI+: 249[M + Na]+ |

TABLE 62-continued

| PEx | PSyn | Data |
|---|---|---|
| 81 | 2 | ESI+: 680 |
| 82 | 2 | ESI+: 641 |
| 83 | 2 | ESI+: 639, 641 |
| 84 | 2 | ESI+: 880, 882 |
| 85 | 10 | ESI+: 548 |
| 86 | 10 | ESI+: 562, 564 |
| 87 | 10 | EI: 256, 258 |
| 88 | 10 | EI: 284, 286 |
| 89 | 10 | ESI+: 576, 578 |
| 90 | 10 | ESI+: 504 |
| 91 | 10 | ESI+: 243 |
| 92 | 10 | ESI+: 590, 592 |
| 93 | 10 | ESI+: 505, 507 |
| 94 | 13 | CI+: 268 |
| 95 | 14 | EI: 215 |
| 96 | 14 | CI+: 216 |
| 97 | 15 | ESI+: 235 |
| 98 | 15 | ESI+: 235 |
| 99 | 16 | ESI+: 244 |
| 100 | 16 | ESI+: 200 |
| 101 | 16 | ESI+: 211 |
| 102 | 18 | ESI+: 223 |
| 103 | 16 | ESI+: 222 |
| 104 | 16 | ESI+: 199 |
| 105 | 16 | EI: 198 |
| 106 | 60 | ESI+: 280 |
| 107 | 74 | ESI+: 393[M + Na]+ |
| 108 | 17 | ESI+: 352 |
| 109 | 17 | ESI+: 336 |
| 110 | 17 | ESI+: 323 |
| 111 | 18 | ESI+: 457 |
| 112 | 18 | ESI+: 390, 392 |
| 113 | 19 | ESI+: 594 |
| 114 | 3 | ESI+: 544 |
| 115 | 3 | ESI+: 532 |
| 116 | 3 | ESI+: 589 |
| 117 | 3 | ESI+: 550 |
| 118 | 3 | ESI+: 582 |
| 119 | 10 | ESI+: 554 |
| 120 | 3 | ESI+: 551 |
| 121 | 20 | ESI+: 367 |
| 122 | 21 | ESI+: 274 |
| 123 | 21 | ESI+: 324 |
| 124 | 21 | ESI+: 270 |
| 125 | 21 | ESI+: 248, 250 |
| 126 | 21 | ESI+: 306, 308 |
| 127 | 22 | ESI+: 713 |
| 128 | 22 | ESI+: 729 |
| 129 | 22 | ESI+: 725, 727 |
| 130 | 22 | ESI+: 713 |
| 131 | 22 | ESI+: 763, 765 |
| 132 | 22 | ESI+: 709, 711 |
| 133 | 22 | ESI+: 709 |
| 134 | 22 | ESI+: 745 |
| 135 | 22 | ESI+: 562, 564 |
| 136 | 22 | EI: 200 |
| 137 | 22 | ESI+: 504, 506 |
| 138 | 22 | ESI+: 476, 478 |
| 139 | 22 | ESI+: 504, 506 |
| 140 | 22 | ESI+: 519, 521 |
| 141 | 23 | ESI: +336 |
| 142 | 24 | ESI+: 322 |
| 143 | 24 | ESI+: 336 |
| 144 | 24 | ESI+: 340 |
| 145 | 24 | ESI+: 322 |

TABLE 63

| PEx | PSyn | Data |
|---|---|---|
| 146 | 24 | ESI+: 322 |
| 147 | 25 | ESI+: 362, 364 |
| 148 | 26 | ESI+: 865 |
| 149 | 26 | ESI+: 865, 867 |
| 150 | 26 | ESI+: 851 |

TABLE 63-continued

| PEx | PSyn | Data |
| --- | --- | --- |
| 151 | 26 | ESI+: 763 |
| 152 | 26 | ESI+: 879, 881 |
| 153 | 26 | ESI+: 941 |
| 154 | 26 | ESI+: 865, 867 |
| 155 | 26 | ESI+: 865, 867 |
| 156 | 26 | ESI+: 865 |
| 157 | 26 | ESI+: 887[M + Na]+ |
| 158 | 26 | ESI+: 879, 881 |
| 159 | 26 | ESI+: 879 |
| 160 | 26 | ESI+: 765 |
| 161 | 26 | ESI+: 871 |
| 162 | 26 | ESI+: 965 |
| 163 | 26 | ESI+: 959 |
| 164 | 26 | ESI+: 849 |
| 165 | 26 | ESI+: 862 |
| 166 | 26 | ESI+: 864 |
| 167 | 26 | ESI+: 835 |
| 168 | 26 | ESI+: 962 |
| 169 | 26 | ESI+: 866 |
| 170 | 26 | ESI+: 879, 881 |
| 171 | 26 | ESI+: 916 |
| 172 | 26 | ESI+: 933, 935 |
| 173 | 26 | ESI+: 872, 874 |
| 174 | 26 | ESI+: 883 |
| 175 | 26 | ESI+: 895, 897 |
| 176 | 26 | ESI+: 883, 885 |
| 177 | 26 | ESI+: 779, 781 |
| 178 | 26 | ESI+: 795 |
| 179 | 26 | ESI+: 825 |
| 180 | 26 | ESI+: 871 |
| 181 | 26 | ESI+: 871 |
| 182 | 26 | ESI+: 941 |
| 183 | 26 | ESI+: 594 |
| 184 | 26 | ESI+: 879, 881 |
| 185 | 26 | ESI+: 594 |
| 186 | 26 | ESI+: 854 |
| 187 | 26 | ESI+: 860 |
| 188 | 26 | ESI+: 609 |
| 189 | 27 | EI: 254, 256 |
| 190 | 27 | ESI+: 239 |
| 191 | 28 | ESI+: 328 |
| 192 | 28 | ESI+: 422 |
| 193 | 28 | ESI+: 319 |
| 194 | 28 | ESI+: 321 |
| 195 | 28 | ESI+: 292 |
| 196 | 28 | ESI+: 419 |
| 197 | 28 | ESI+: 373, 375 |
| 198 | 28 | ESI+: 390 |
| 199 | 28 | ESI+: 329 |
| 200 | 28 | ESI+: 340 |
| 201 | 28 | ESI+: 352 |
| 202 | 28 | ESI+: 236 |
| 203 | 28 | ESI+: 252 |
| 204 | 28 | ESI+: 282 |
| 205 | 28 | ESI+: 328 |
| 206 | 28 | ESI+: 328 |
| 207 | 28 | ESI+: 398 |
| 208 | 28 | ESI+: 532 |
| 209 | 29 | ESI+: 343 |
| 210 | 4 | ESI+: 745 |
| 211 | 4 | ESI+: 747 |
| 212 | 4 | NMR1: 1.28-1.60(27H, m), 2.85-3.05(2H, m), 3.49(2H, s), 4.34-4.43(1H, m), 7.11-7.31(5H, m), 7.34(1H, d, J = 8.0 Hz), 7.43(1H, d, J = 1.6 Hz), 7.83(2H, d, J = 8.8 Hz), 8.12(2H, d, J = 8.8 Hz), 8.52(1H, d, J = 7.6 Hz), 10.10-10.32(1H, m), 11.19(1H, s) |
| 213 | 4 | ESI+: 793 |
| 214 | 4 | ESI+: 753 |
| 215 | 4 | ESI+: 785 |
| 216 | 4 | ESI+: 779[M + Na]+ |

TABLE 64

| PEx | PSyn | Data |
| --- | --- | --- |
| 217 | 4 | NMR1: 1.20-1.63(27H, m), 2.84-3.05(2H, m), 3.49(2H, s), 4.34-4.44(1H, m), 7.03-7.09(1H, m), 7.14-7.36(6H, m), 7.83(2H, d, J = 8.8 Hz), 8.11(2H, d, J = 8.8 Hz), 8.51(1H, d, J = 8.0 Hz), 10.26(1H, s), 11.19(1H, s) |
| 218 | 4 | ESI+: 424 |
| 219 | 4 | ESI+: 424 |
| 220 | 4 | ESI+: 424 |
| 221 | 4 | ESI+: 823 |
| 222 | 4 | ESI+: 751 |
| 223 | 4 | ESI+: 873[M + Na]+ |
| 224 | 4 | ESI+: 737 |
| 225 | 4 | ESI+: 737 |
| 226 | 4 | ESI+: 881 |
| 227 | 4 | ESI+: 803 |
| 228 | 4 | ESI+: 803 |
| 229 | 4 | ESI+: 819, 821 |
| 230 | 4 | ESI+: 815, 817 |
| 231 | 4 | ESI+: 803, 805 |
| 232 | 4 | ESI+: 853 |
| 233 | 4 | ESI+: 799 |
| 234 | 4 | ESI+: 799 |
| 235 | 4 | ESI+: 835, 837 |
| 236 | 4 | ESI+: 983 |
| 237 | 4 | ESI: 765 |
| 238 | 4 | ESI+: 751 |
| 239 | 4 | ESI+: 751, 753 |
| 240 | 4 | ESI+: 751 |
| 241 | 4 | ESI+: 751 |
| 242 | 4 | ESI+: 751 |
| 243 | 4 | ESI+: 765, 767 |
| 244 | 4 | ESI+: 895, 897 |
| 245 | 4 | ESI+: 348, 350 |
| 246 | 4 | ESI+: 404 |
| 247 | 4 | ESI+: 779, 781 |
| 248 | 4 | ESI+: 793 |
| 249 | 4 | ESI+: 754 |
| 250 | 4 | ESI+: 740 |
| 251 | 4 | ESI+: 740 |
| 252 | 4 | ESI+: 754 |
| 253 | 4 | ESI+: 884 |
| 254 | 32 | ESI−: 304 |
| 255 | 35 | ESI+: 566, 568 |
| 256 | 35 | ESI+: 376, 378 |
| 257 | 35 | ESI+: 390, 392 |
| 258 | 38 | ESI+: 277, 279 |
| 259 | 38 | ESI+: 289 |
| 260 | 38 | ESI+: 301 |
| 261 | 38 | EI: 276 |
| 262 | 38 | EI: 276 |
| 263 | 1 | ESI+: 273 |
| 264 | 1 | ESI+: 261 |
| 265 | 1 | ESI+: 279 |
| 266 | 1 | ESI+: 311 |
| 267 | 1 | ESI+: 277 |
| 268 | 1 | ESI+: 321 |
| 269 | 1 | ESI+: 374 |
| 270 | 1 | ESI+: 446[M + Na]+ |
| 271 | 1 | EI: 290, 292 |
| 272 | 1 | ESI+: 347 |

TABLE 64-continued

| PEx | PSyn | Data |
|---|---|---|
| 273 | 1 | EI: 410 |
| 274 | 1 | ESI+: 305 |
| 275 | 1 | ESI+: 319 |
| 276 | 1 | ESI+: 334, 336 |
| 277 | 41 | ESI+: 865 |
| 278 | 41 | ESI+: 927, 929 |
| 279 | 41 | ESI+: 1075 |
| 280 | 46 | EI: 274, 276 |
| 281 | 6 | ESI−: 219 |
| 282 | 6 | ESI−: 219 |
| 283 | 6 | ESI−: 219 |
| 284 | 17 | ESI+: 380 |
| 285 | 4 | ESI+: 909, 911 |
| 286 | 4 | ESI+: 923, 925 |
| 287 | 54 | ESI+: 422, 424 |
| 288 | 4 | ESI+: 583 |
| 289 | 3 | ESI+: 493 |
| 290 | 22 | ESI+: 288, 290 |
| 291 | 2 | ESI+: 880 |
| 292 | 2 | ESI+: 629 |
| 293 | 10 | ESI+: 539 |

TABLE 65

| PEx | PSyn | Data |
|---|---|---|
| 294 | 4 | ESI+: 814 |
| 295 | 4 | ESI+: 742 |
| 296 | 26 | ESI+: 728 |
| 297 | 2 | ESI+: 629 |
| 298 | 10 | ESI+: 539 |
| 299 | 4 | ESI+: 742 |
| 300 | 61 | ESI+: 282 |
| 301 | 2 | ESI+: 643 |
| 302 | 10 | ESI+: 553 |
| 303 | 4 | ESI+: 742 |
| 304 | 2 | ESI+: 634 |
| 305 | 26 | APCI/ESI+: 513 |
| 306 | 2 | APCI/ESI+: 874 |
| 307 | 17 | ESI+: 273 |
| 308 | 2 | ESI+: 622 |
| 309 | 4 | APCI/ESI−: 504 |
| 310 | 2 | APCI/ESI+: 867 |
| 311 | 56 | ESI+: 378, 380 |
| 312 | 24 | ESI+: 625, 627 |
| 313 | 2 | ESI+: 680 |
| 314 | 9 | ESI+: 525, 527 |
| 315 | 2 | ESI+: 886 |
| 316 | 2 | ESI+: 640 |
| 317 | 26 | ESI+: 499 |
| 318 | 2 | ESI+: 878 |
| 319 | 65 | APCI/ESI+: 398 |
| 320 | 2 | ESI+: 878 |
| 321 | 62 | APCI/ESI+: 342 |
| 322 | 26 | APCI/ESI+: 513 |
| 323 | 2 | APCI/ESI+: 875 |
| 324 | 2 | ESI+: 672 |
| 325 | 4 | ESI+: 884 |
| 326 | 4 | ESI+: 854 |
| 327 | 4 | ESI+: 510 |
| 328 | 2 | ESI+: 871 |
| 329 | 16 | EI: 240 |
| 330 | 2 | ESI+: 644 |
| 331 | 26 | ESI+: 868 |
| 332 | 2 | ESI+: 638 |
| 333 | 38 | NMR2: 1.61-1.63(9H, m), 4.62(2H, s), 7.47(1H, dd, J = 1.6, 8.4 Hz), 7.79-7.90(2H, m), 7.91-7.98(1H, m) |
| 334 | 62 | APCI/ESI+: 378 |
| 335 | 26 | APCI/ESI+: 932 |
| 336 | 2 | ESI+: 785 |
| 337 | 2 | ESI+: 854 |

TABLE 65-continued

| PEx | PSyn | Data |
|---|---|---|
| 338 | 26 | NMR2: 1.42(9H, s), 1.50-1.57(27H, m), 2.44-2.59(2H, m), 3.01-3.18(4H, m), 4.74-4.82(1H, m), 5.90(1H, d, J = 7.6 Hz), 7.06(1H, dd, J = 2.4, 8.4 Hz), 7.13(2H, d, J = 8.4 Hz), 7.27-7.32(1H, m), 7.81(2H, d, J = 8.8 Hz), 7.89(2H, d, J = 8.4 Hz), 8.13(2H, d, J = 8.8 Hz), 10.64(1H, s), 11.61(1H, s) |
| 339 | 53 | ESI+: 872 |
| 340 | 41 | ESI+: 854 |
| 341 | 2 | ESI+: 785 |
| 342 | 41 | ESI+: 868 |
| 343 | 2 | ESI+: 751, 753 |
| 344 | 26 | APCI/ESI+: 518 |
| 345 | 2 | NMR2: 1.09-1.17(3H, m), 1.45-1.65(36H, m), 2.57-2.80(2H, m), 3.06-3.50(4H, m), 4.48-4.72(2H, m), 6.99-7.11(1H, m), 7.19-7.33(3H, m), 7.38(1H, d, J = 8.4 Hz), 7.78-7.85(2H, m), 7.92-8.02(2H, m), 8.09-8.17(2H, m), 8.43-8.50(1H, m), 10.65(1H, brs), 11.62(1H, brs) |
| 346 | 26 | ESI+: 594 |

TABLE 66

| PEx | PSyn | Data |
|---|---|---|
| 347 | 10 | ESI+: 504 |
| 348 | 2 | ESI+: 865 |
| 349 | 26 | ESI+: 513 |
| 350 | 2 | ESI+: 874 |
| 351 | 2 | ESI+: 638 |
| 352 | 21 | APCI/ESI+: 432 |
| 353 | 26 | APCI/ESI+: 603 |
| 354 | 2 | ESI+: 964 |
| 355 | 17 | APCI/ESI−: 782 |
| 356 | 26 | APCI/ESI+: 507 |
| 357 | 2 | ESI+: 868 |
| 358 | 26 | APCI/ESI+: 614 |
| 359 | 2 | APCI/ESI+: 975 |
| 360 | 17 | APCI/ESI+: 795 |
| 361 | 2 | ESI+: 652, 654 |
| 362 | 3 | ESI−: 249 |
| 363 | 4 | ESI+: 504 |
| 364 | 2 | ESI+: 865 |
| 365 | 18 | EI: 232 |
| 366 | 38 | EI: 309, 311 |
| 367 | 70 | ESI+: 362, 364 |
| 368 | 4 | ESI+: 894 |
| 369 | 66 | ESI+: 380 |
| 370 | 26 | ESI+: 551 |
| 371 | 2 | ESI+: 912 |
| 372 | 2 | ESI+: 865 |
| 373 | 66 | ESI+: 342 |
| 374 | 2 | ESI+: 785 |
| 375 | 26 | ESI+: 507 |
| 376 | 2 | ESI+: 868 |
| 377 | 55 | ESI+: 301 |
| 378 | 2 | ESI+: 650 |
| 379 | 2 | ESI+: 865, 867 |
| 380 | 37 | ESI−: 343 |
| 381 | 4 | ESI+: 670, 672 |
| 382 | 58 | ESI+: 518 |

TABLE 66-continued
| PEx | PSyn | Data |
|---|---|---|
| 383 | 2 | ESI+: 879, 881 |
| 384 | 4 | ESI+: 676, 678 |
| 385 | 58 | ESI+: 524 |
| 386 | 2 | ESI+: 885 |
| 387 | 54 | ESI+: 273 |
| 388 | 16 | Cl+: 276, 278 |
| 389 | 2 | ESI+: 837 |
| 390 | 2 | ESI+: 664 |
| 391 | 76 | ESI+: 576 |
| 392 | 4 | ESI+: 879 |
| 393 | 4 | ESI+: 885, 887 |
| 394 | 2 | ESI+: 865, 867 |
| 395 | 2 | ESI+: 666 |
| 396 | 66 | APCI/ESI+: 379 |
TABLE 67
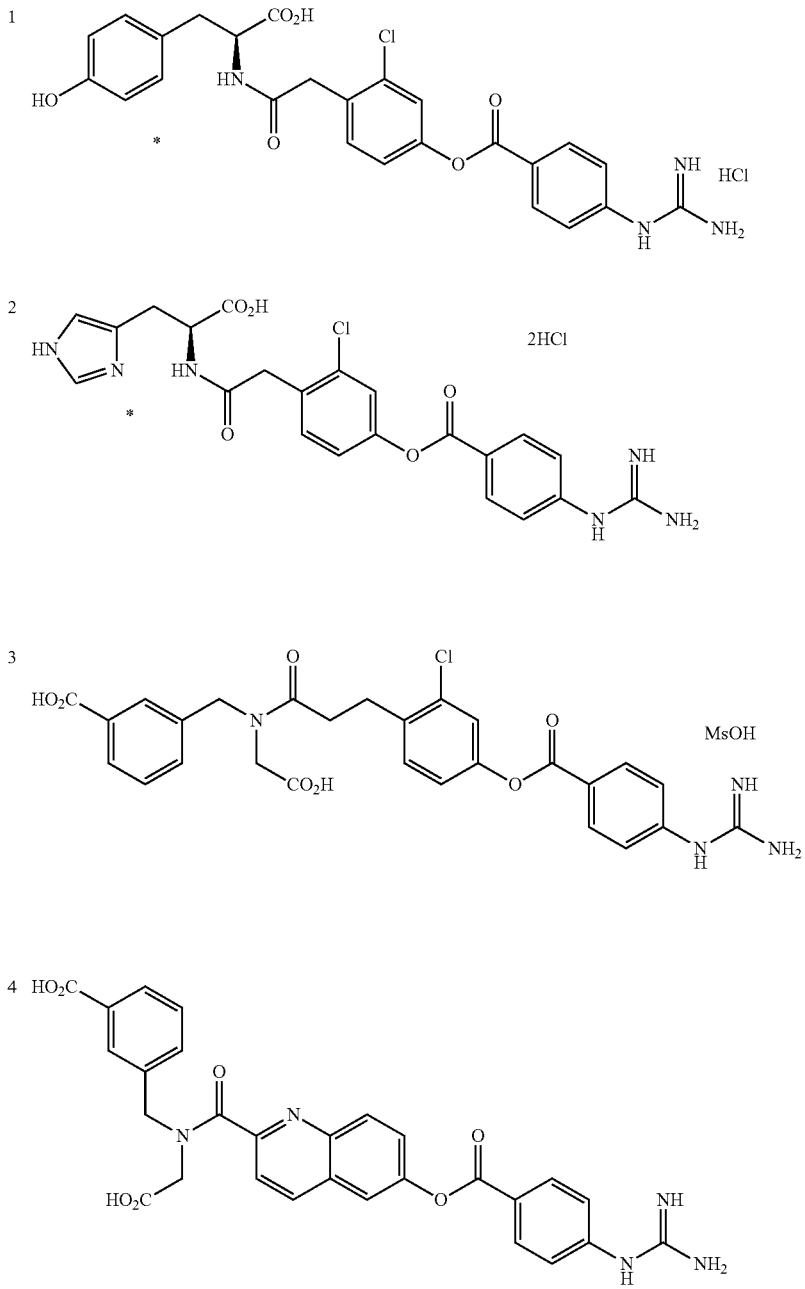

TABLE 67-continued
| Ex | Str |
|---|---|
| 5 | 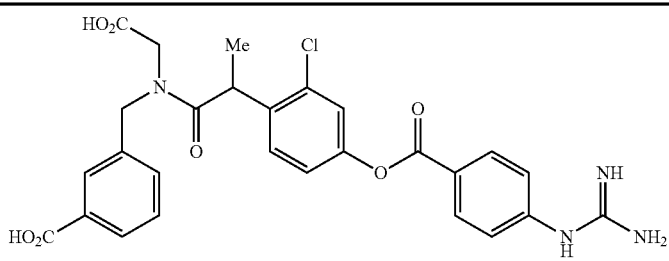 |
| 6 | 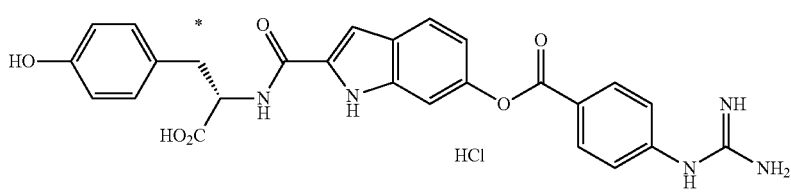 [SMILES: N=C(N)Nc1ccc(C(=O)Oc2ccc3cc(C(=O)N[C@@H](Cc4ccc(O)cc4)C(=O)O)[nH]c3c2)cc1 ; Cl] |
TABLE 68
| Ex | Str |
|---|---|
| 7 | 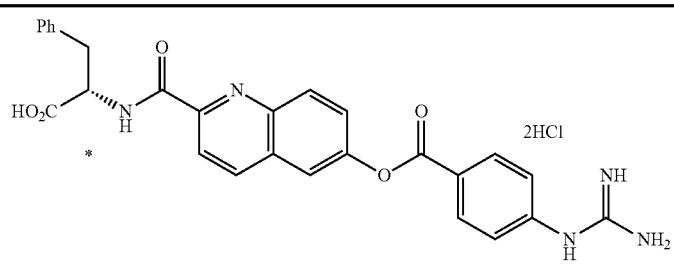 |
| 8 | 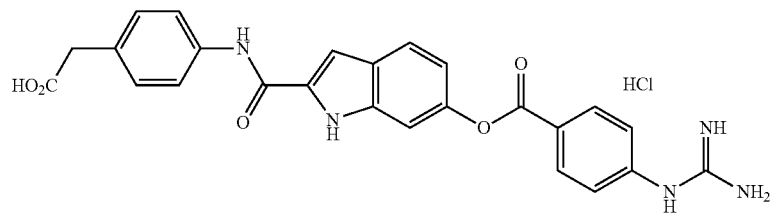 [SMILES: N=C(N)Nc1ccc(C(=O)Oc2ccc3cc(C(=O)Nc4ccc(CC(=O)O)cc4)[nH]c3c2)cc1 ; Cl] |
| 9 | 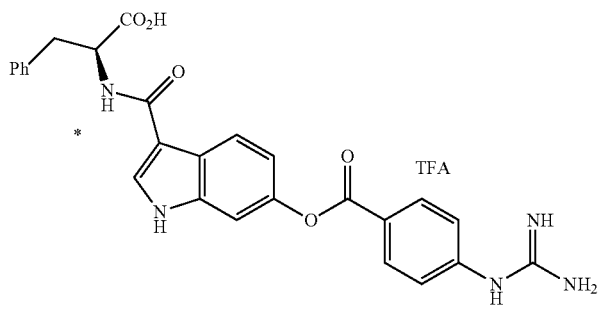 [SMILES: N=C(N)Nc1ccc(C(=O)Oc2ccc3c(C(=O)N[C@@H](Cc4ccccc4)C(=O)O)c[nH]c3c2)cc1] |
| 10 | 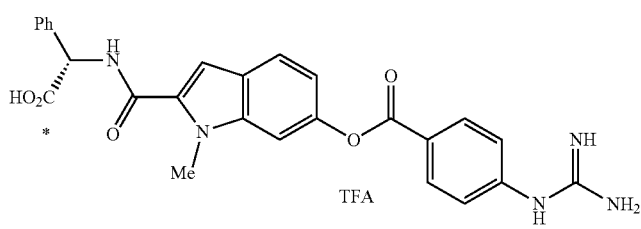 [SMILES: Cn1c(C(=O)N[C@H](C(=O)O)c2ccccc2)cc2ccc(OC(=O)c3ccc(NC(=N)N)cc3)cc21] |

TABLE 68-continued

| Ex | Str |
| --- | --- |
| 11 | |
| 12 | |

TABLE 69

| Ex | Str |
| --- | --- |
| 13 | |
| 14 | |
| 15 | |

TABLE 69-continued
| Ex | Str |
|---|---|
| 16 | 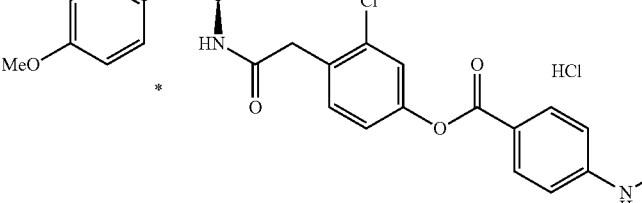 |
| 17 | |
| 18 | |
TABLE 70
| Ex | Str |
|---|---|
| 19 | 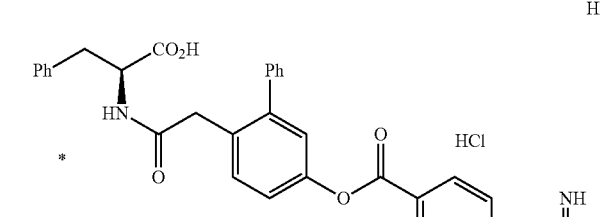 |
| 20 | |
| 21 | 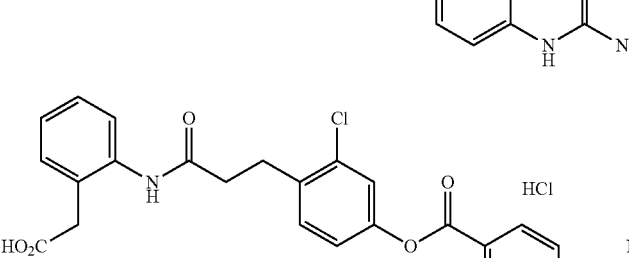 |

TABLE 70-continued
| Ex | Str |
|---|---|
| 22 | 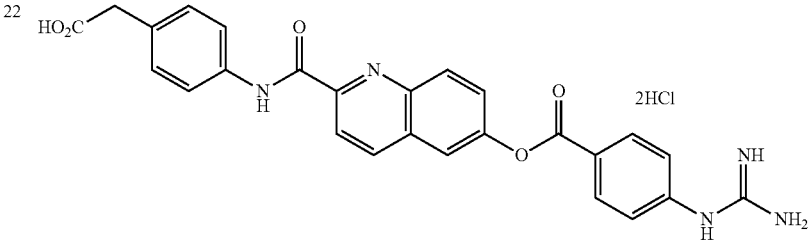 2HCl |
| 23 | 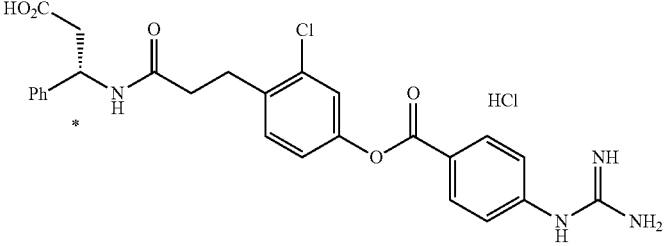 [SMILES: N=C(N)Nc1ccc(C(=O)Oc2ccc(CCC(=O)N[C@@H](CC(=O)O)c3ccccc3)c(Cl)c2)cc1 ; Cl] HCl |
| 24 | 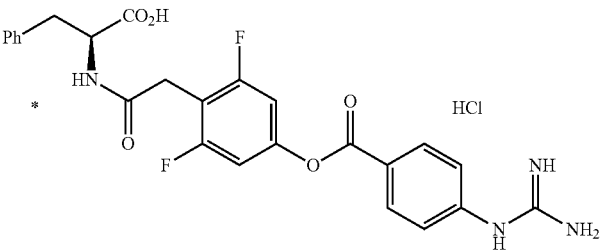 [SMILES: N=C(N)Nc1ccc(C(=O)Oc2cc(F)c(CC(=O)N[C@@H](Cc3ccccc3)C(=O)O)c(F)c2)cc1 ; Cl] HCl |
TABLE 71
| Ex | Str |
|---|---|
| 25 | 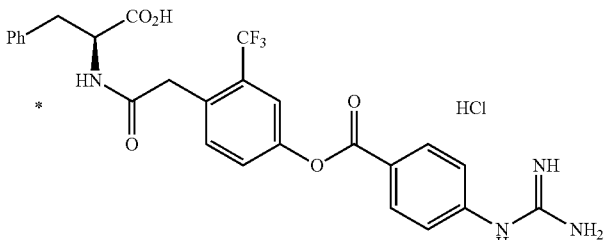 HCl |
| 26 | 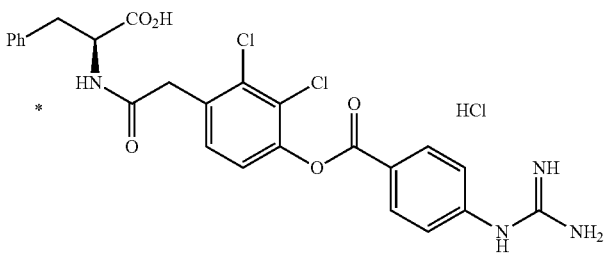 [SMILES: N=C(N)Nc1ccc(C(=O)Oc2ccc(CC(=O)N[C@@H](Cc3ccccc3)C(=O)O)c(Cl)c2Cl)cc1 ; Cl] HCl |

TABLE 71-continued
| Ex | Str |
|---|---|
| 27 | 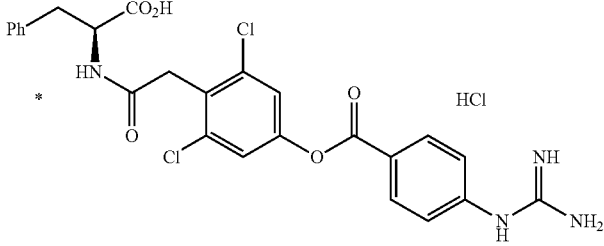 [SMILES: N=C(N)Nc1ccc(C(=O)Oc2cc(Cl)c(CC(=O)N[C@@H](Cc3ccccc3)C(=O)O)c(Cl)c2)cc1 ; Cl] |
| 28 | 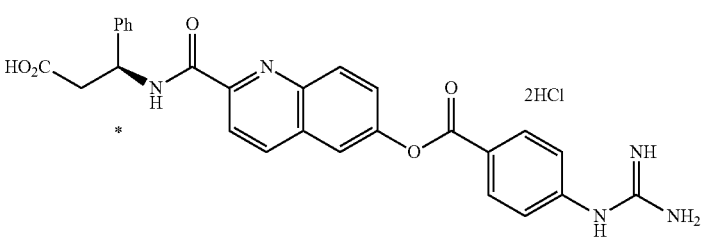 [SMILES: N=C(N)Nc1ccc(C(=O)Oc2ccc3nc(C(=O)N[C@@H](CC(=O)O)c4ccccc4)ccc3c2)cc1 ; "2HCl"] |
| 29 | 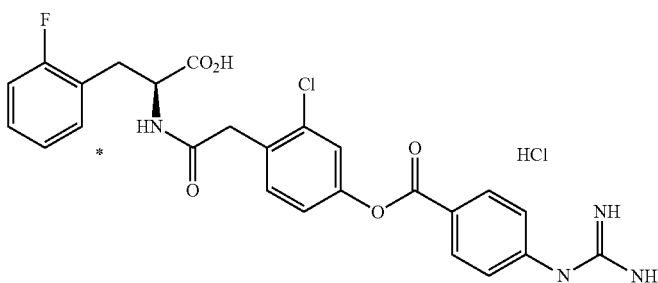 |
| 30 | 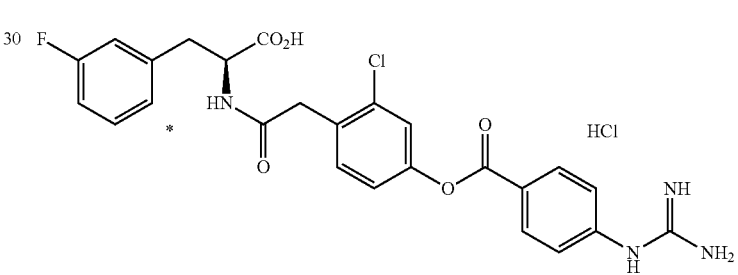 |
TABLE 72
| Ex | Str |
|---|---|
| 31 | 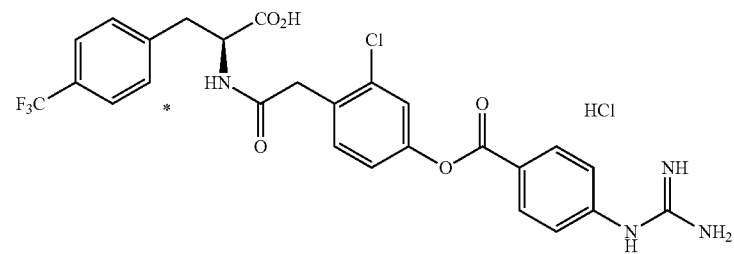 [SMILES: N=C(N)Nc1ccc(C(=O)Oc2ccc(CC(=O)N[C@@H](Cc3ccc(C(F)(F)F)cc3)C(=O)O)c(Cl)c2)cc1 ; Cl] |

TABLE 72-continued
| Ex | Str |
|---|---|
| 32 | 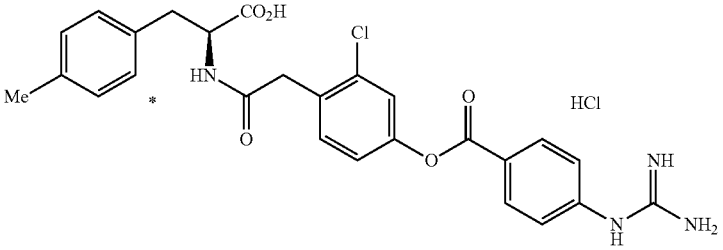 [SMILES: Cc1ccc(C[C@H](NC(=O)Cc2ccc(OC(=O)c3ccc(NC(=N)N)cc3)cc2Cl)C(=O)O)cc1 ; Cl] |
| 33 | 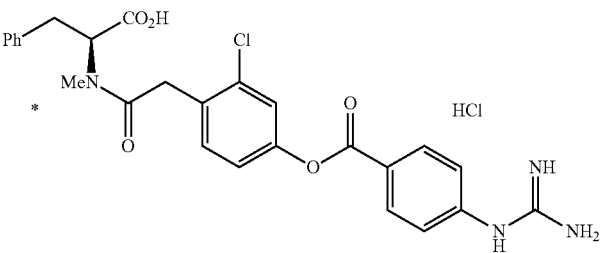 [SMILES: CN(C(=O)Cc1ccc(OC(=O)c2ccc(NC(=N)N)cc2)cc1Cl)[C@@H](Cc1ccccc1)C(=O)O ; Cl] |
| 34 | 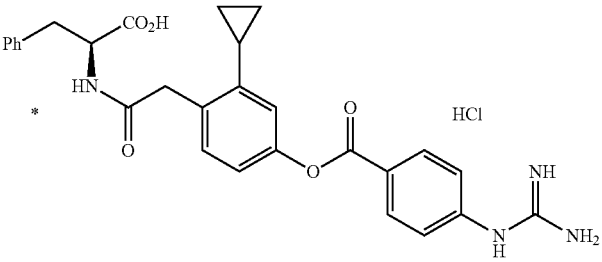 [SMILES: N=C(N)Nc1ccc(C(=O)Oc2ccc(CC(=O)N[C@@H](Cc3ccccc3)C(=O)O)c(C3CC3)c2)cc1 ; Cl] |
| 35 | 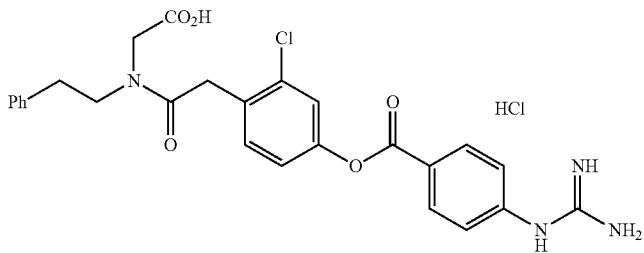 [SMILES: N=C(N)Nc1ccc(C(=O)Oc2ccc(CC(=O)N(CCc3ccccc3)CC(=O)O)c(Cl)c2)cc1 ; Cl] |
| 36 | 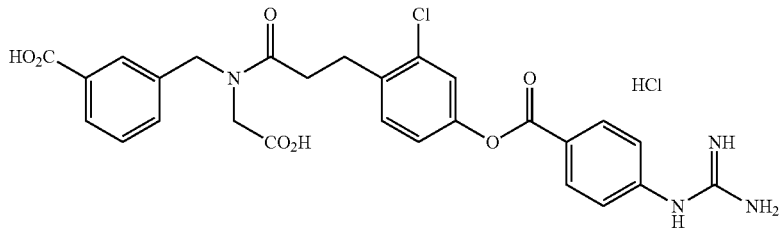 [SMILES: N=C(N)Nc1ccc(C(=O)Oc2ccc(CCC(=O)N(CC(=O)O)Cc3cccc(C(=O)O)c3)c(Cl)c2)cc1 ; Cl] |

TABLE 73
| Ex | Str |
|---|---|
| 37 | 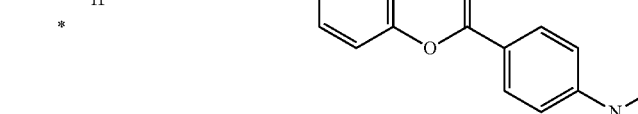 |
| 38 | 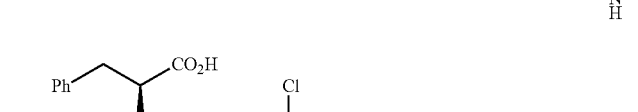 |
| 39 | 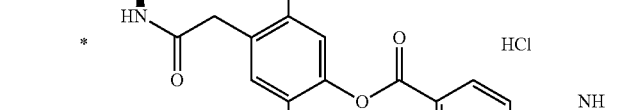 |
| 40 | 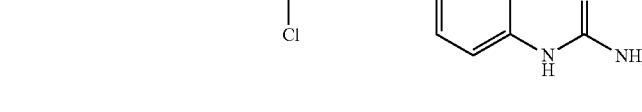 |
| 41 | 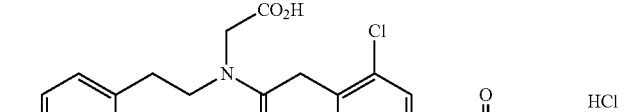 |
| 42 | 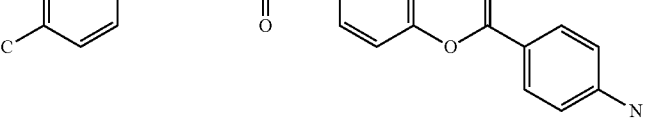 |

TABLE 74
| Ex | Str |
|---|---|
| 43 | 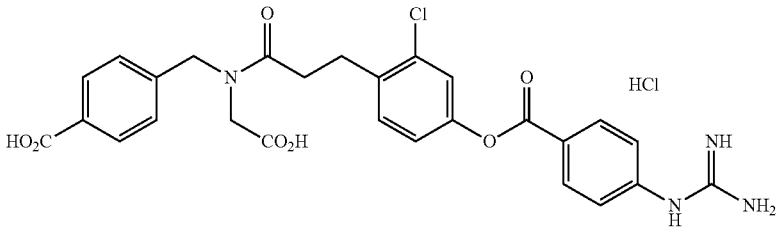 [SMILES: N=C(N)Nc1ccc(C(=O)Oc2ccc(CCC(=O)N(CC(=O)O)Cc3ccc(C(=O)O)cc3)c(Cl)c2)cc1 ; Cl] |
| 44 | 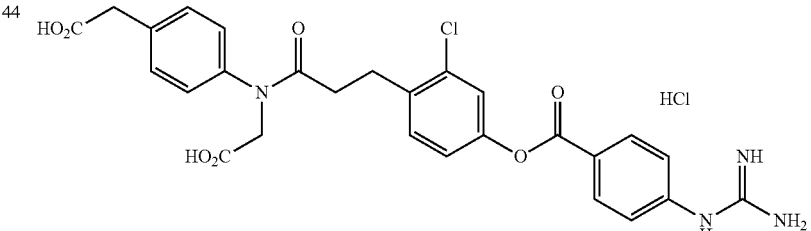 |
| 45 | 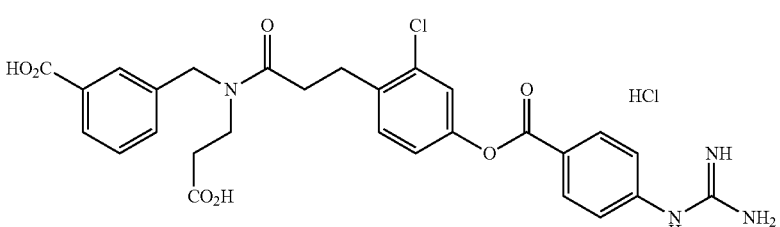 |
| 46 | 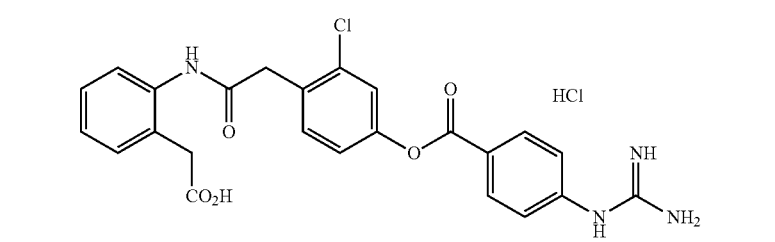 [SMILES: N=C(N)Nc1ccc(C(=O)Oc2ccc(CC(=O)Nc3ccccc3CC(=O)O)c(Cl)c2)cc1 ; Cl] |
| 47 | 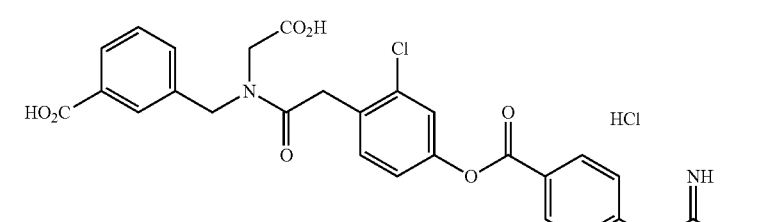 |
| 48 | 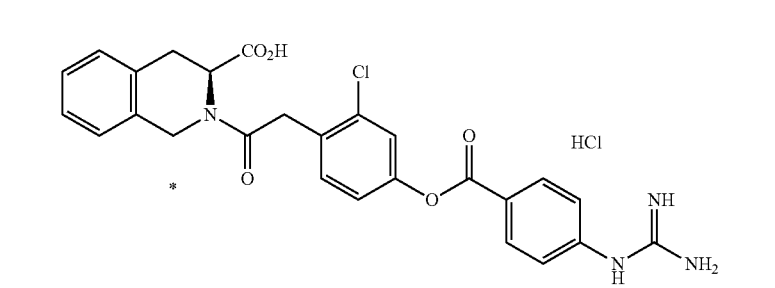 [SMILES: N=C(N)Nc1ccc(C(=O)Oc2ccc(CC(=O)N3Cc4ccccc4C[C@H]3C(=O)O)c(Cl)c2)cc1 ; Cl] |

TABLE 75

| Ex | Str |
|---|---|
| 49 | (structure: 2-naphthylmethyl-L-alanine-CO2H with NH-C(=O)-CH2- linked to 2-chloro-4-(4-guanidinobenzoyloxy)phenyl) · HCl |
| 50 | (structure: Ph-CH2-CH(CO2H)-NH-C(=O)-(CH2)3-(2-chloro-4-(4-guanidinobenzoyloxy)phenyl)) · HCl |
| 51 | (structure: 3-HO2C-C6H4-CH2-N(CH2CO2H)-C(=O)-(CH2)3-(2-chloro-4-(4-guanidinobenzoyloxy)phenyl)) · HCl |
| 52 | (structure: 2-HO2C-C6H4-CH2-NH-C(=O)-CH2CH2-(2-chloro-4-(4-guanidinobenzoyloxy)phenyl)) · HCl |
| 53 | (structure: 2-HO2C-C6H4-CH2-N(CH2CO2H)-C(=O)-CH2CH2-(2-chloro-4-(4-guanidinobenzoyloxy)phenyl)) · HCl |
| 54 | (structure: Ph-CH2-CH(CO2H)-N(CH2CH2CO2H)-C(=O)-CH2-(2-chloro-4-(4-guanidinobenzoyloxy)phenyl)) · HCl |

TABLE 76
| Ex | Str |
|---|---|
| 55 | 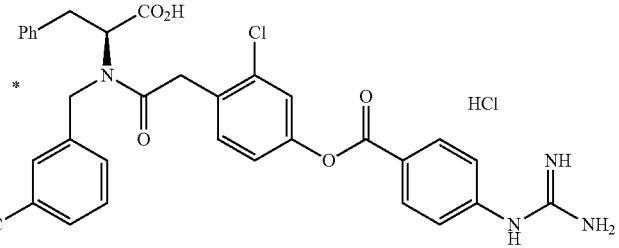 |
| 56 | 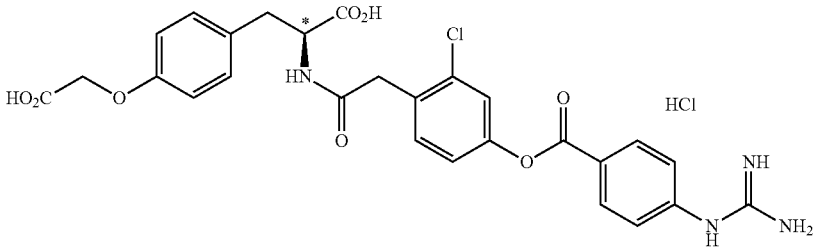 [SMILES: N=C(N)Nc1ccc(C(=O)Oc2ccc(CC(=O)N[C@@H](Cc3ccc(OCC(=O)O)cc3)C(=O)O)c(Cl)c2)cc1 ; Cl] |
| 57 | 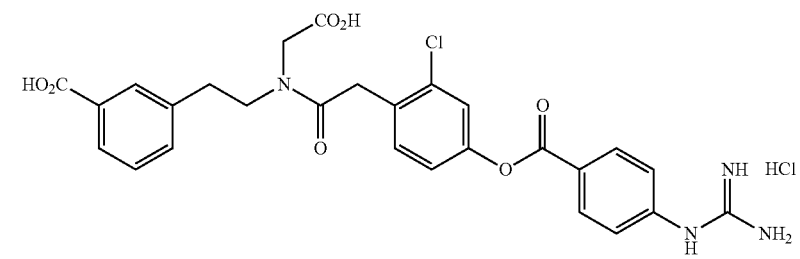 [SMILES: N=C(N)Nc1ccc(C(=O)Oc2ccc(CC(=O)N(CCc3cccc(C(=O)O)c3)CC(=O)O)c(Cl)c2)cc1 ; Cl] |
| 58 | 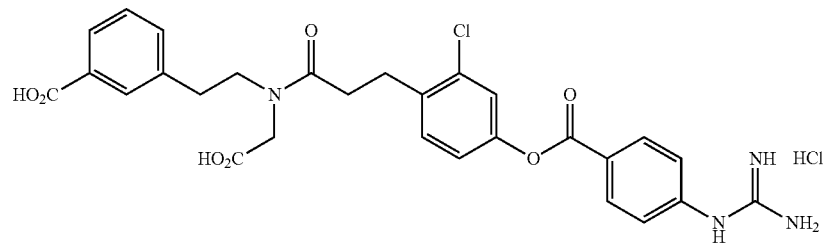 [SMILES: N=C(N)Nc1ccc(C(=O)Oc2ccc(CCC(=O)N(CCc3cccc(C(=O)O)c3)CC(=O)O)c(Cl)c2)cc1 ; Cl] |
| 59 | 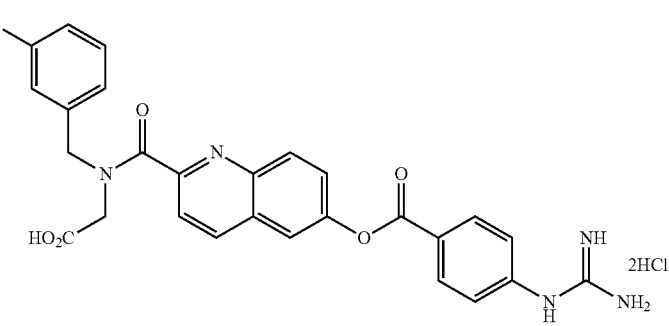 |

TABLE 77

| Ex | Str |
|---|---|
| 60 | (structure) |
| 61 | (structure) |
| 62 | (structure) |
| 63 | (structure) |
| 64 | (structure) |

TABLE 78

| Ex | Str |
|---|---|
| 65 | (structure) |
| 66 | (structure) |
| 67 | (structure) |
| 68 | (structure) |
| 69 | (structure) |
| 70 | (structure) |

TABLE 79
| Ex | Str |
|---|---|
| 71 | 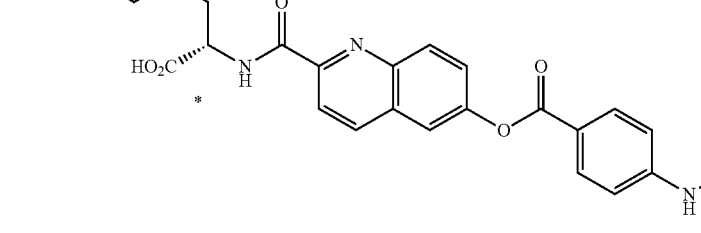 |
| 72 | 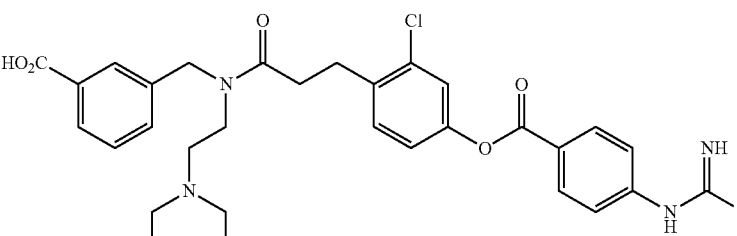 |
| 73 | 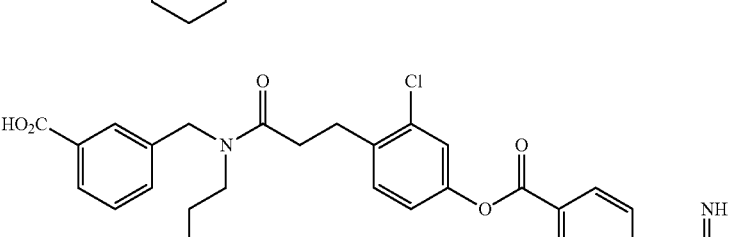 |
| 74 | 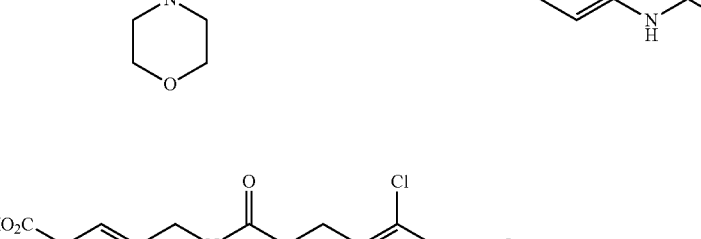 |
| 75 | 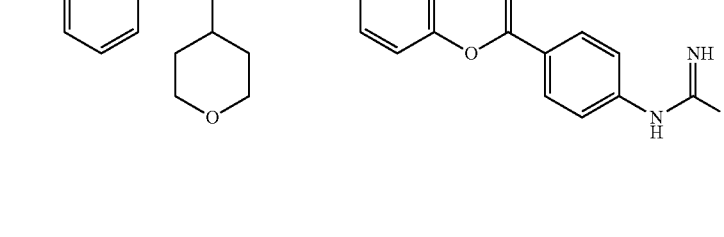 |

TABLE 80

| Ex | Str |
|---|---|
| 76 | (structure: 4-carboxypiperidine-N-ethyl-N-(3-carboxybenzyl)-propanamide linked to 3-chloro-4-phenyl ester of 4-guanidinobenzoate, 2HCl) |
| 77 | (structure: 6-carboxypyridin-2-yl-methyl-N-(carboxymethyl)-propanamide linked to 3-chloro-4-phenyl ester of 4-guanidinobenzoate, 2HCl) |
| 78 | (structure: 3-(carboxymethyl)benzyl-N-(carboxymethyl)-propanamide linked to 3-chloro-4-phenyl ester of 4-guanidinobenzoate, HCl) |
| 79 | (structure: 4-carboxyquinolin-2-yl-methyl-N-(carboxymethyl)-propanamide linked to 3-chloro-4-phenyl ester of 4-guanidinobenzoate, 2HCl) |
| 80 | (structure: 5-carboxythiophen-3-yl-methyl-N-(carboxymethyl)-quinoline-2-carboxamide linked to 6-phenyl ester of 4-guanidinobenzoate, 2HCl) |
| 81 | (structure: 3-carboxybenzyl-N-(carboxymethyl)-N-methyl-glycinamide linked to 3-chloro-4-phenyl ester of 4-guanidinobenzoate, HCl) |

TABLE 81
| Ex | Str |
|---|---|
| 82 | 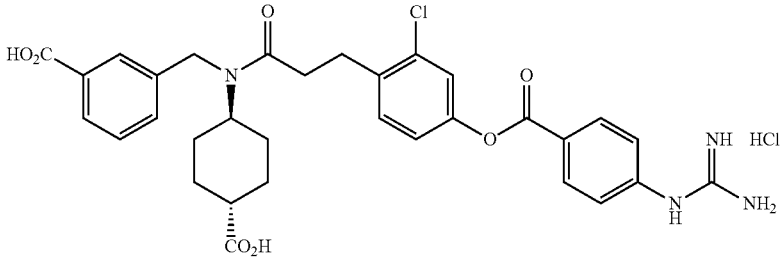 [SMILES: N=C(N)Nc1ccc(C(=O)Oc2ccc(CCC(=O)N(Cc3cccc(C(=O)O)c3)[C@H]3CC[C@H](C(=O)O)CC3)c(Cl)c2)cc1 ; Cl] |
| 83 | 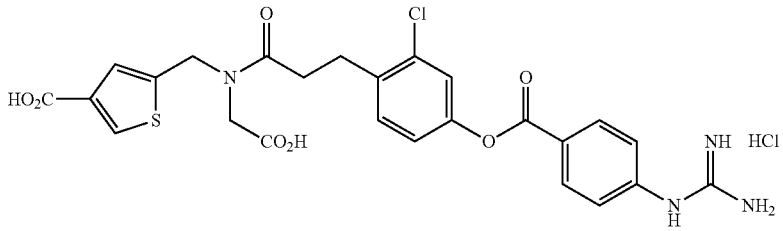 [SMILES: N=C(N)Nc1ccc(C(=O)Oc2ccc(CCC(=O)N(CC(=O)O)Cc3cc(C(=O)O)cs3)c(Cl)c2)cc1 ; Cl] |
| 84 | 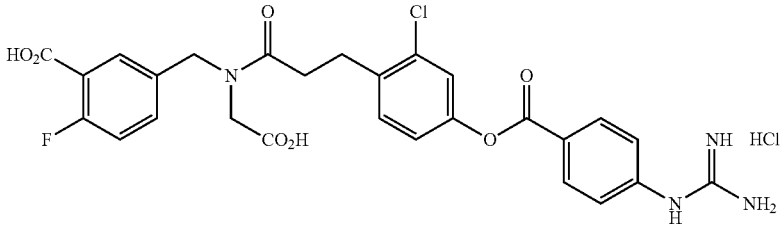 [SMILES: N=C(N)Nc1ccc(C(=O)Oc2ccc(CCC(=O)N(CC(=O)O)Cc3ccc(F)c(C(=O)O)c3)c(Cl)c2)cc1 ; Cl] |
| 85 | 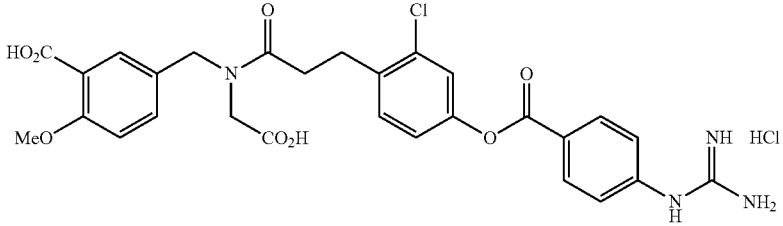 [SMILES: COc1ccc(CN(CC(=O)O)C(=O)CCc2ccc(OC(=O)c3ccc(NC(=N)N)cc3)cc2Cl)cc1C(=O)O ; Cl] |
| 86 | 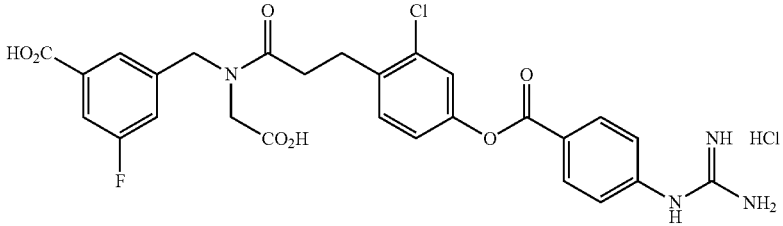 [SMILES: N=C(N)Nc1ccc(C(=O)Oc2ccc(CCC(=O)N(CC(=O)O)Cc3cc(F)cc(C(=O)O)c3)c(Cl)c2)cc1 ; Cl] |
| 87 | 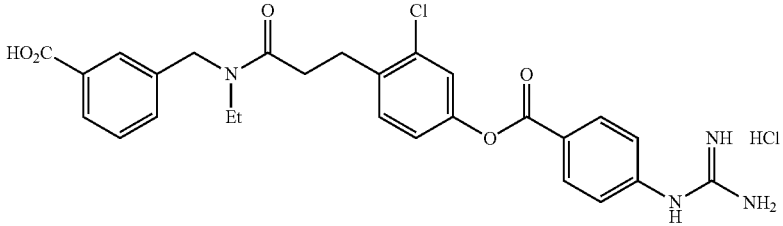 [SMILES: CCN(Cc1cccc(C(=O)O)c1)C(=O)CCc1ccc(OC(=O)c2ccc(NC(=N)N)cc2)cc1Cl ; Cl] |

TABLE 82
| Ex | Str |
|---|---|
| 88 | 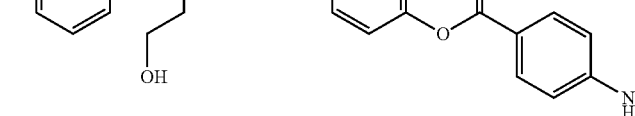 |
| 89 | 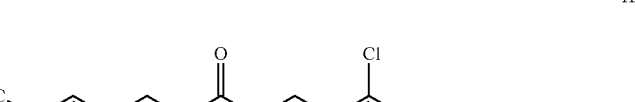 |
| 90 | 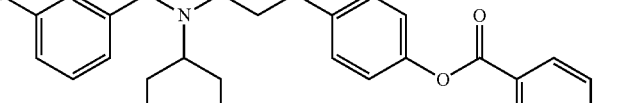 |
| 91 |  |
| 92 | 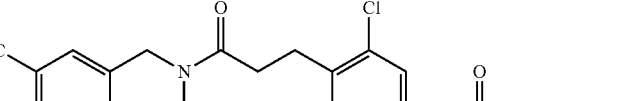 |
| 93 | 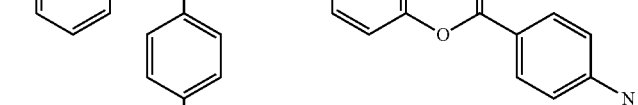 |

TABLE 83
| Ex | Str |
|---|---|
| 94 | 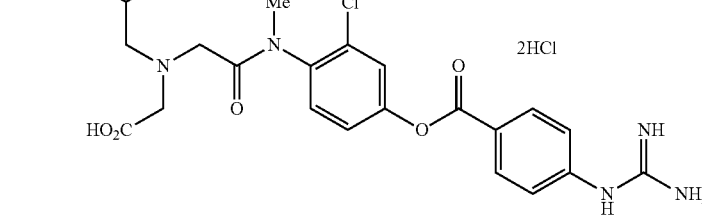 |
| 95 | 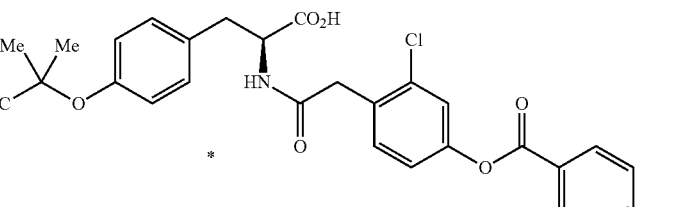 |
| 96 | 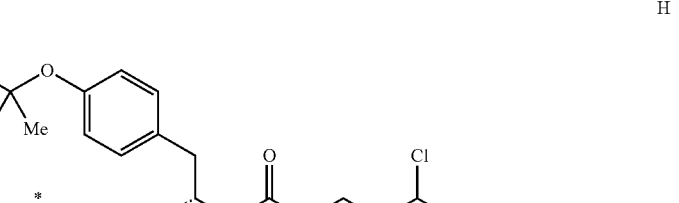 |
| 97 | 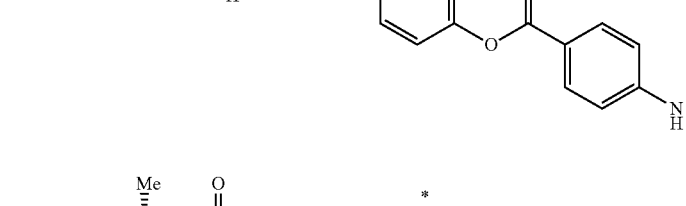 |
| 98 | 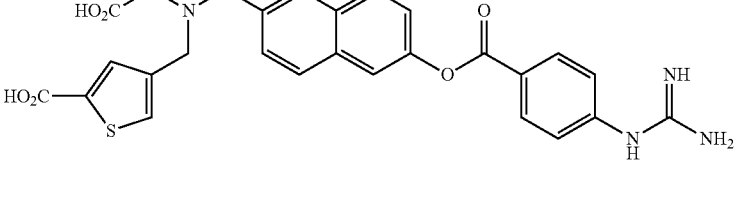 |

TABLE 84
| Ex | Str |
|---|---|
| 99 | 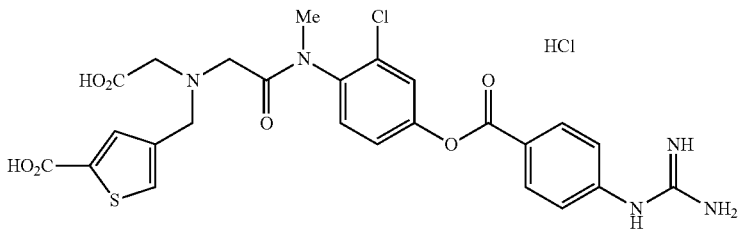 [SMILES: CN(C(=O)CN(CC(=O)O)Cc1csc(C(=O)O)c1)c1ccc(OC(=O)c2ccc(NC(=N)N)cc2)cc1Cl ; Cl] HCl |
| 100 | 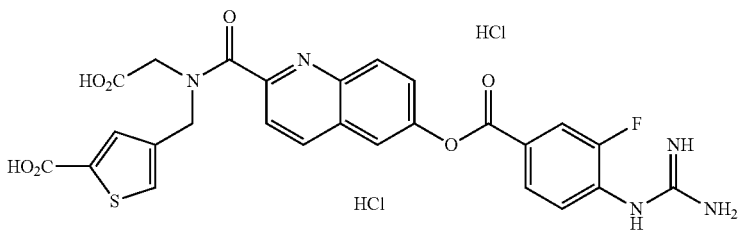 [SMILES: N=C(N)Nc1ccc(C(=O)Oc2ccc3nc(C(=O)N(CC(=O)O)Cc4csc(C(=O)O)c4)ccc3c2)cc1F ; Cl ; Cl] HCl, HCl |
| 101 | 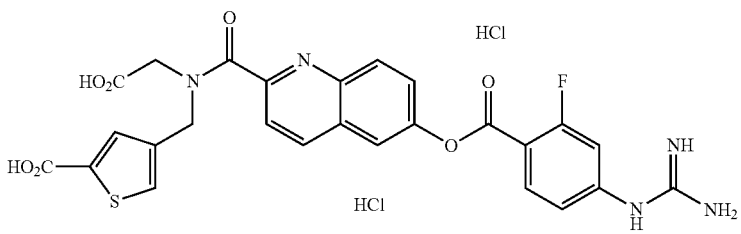 [SMILES: N=C(N)Nc1ccc(C(=O)Oc2ccc3nc(C(=O)N(CC(=O)O)Cc4csc(C(=O)O)c4)ccc3c2)c(F)c1 ; Cl ; Cl] HCl, HCl |
| 102 | 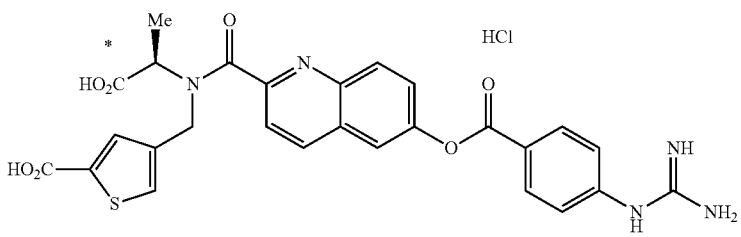 HCl |
| 103 | 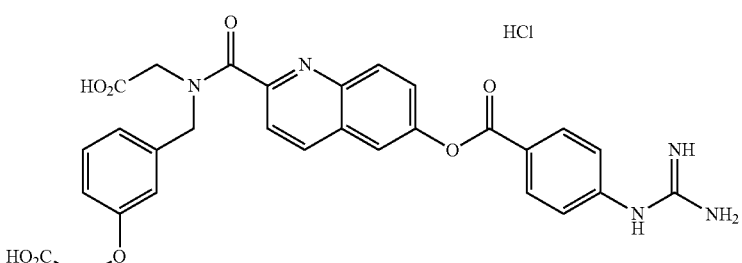 HCl |
| 104 | 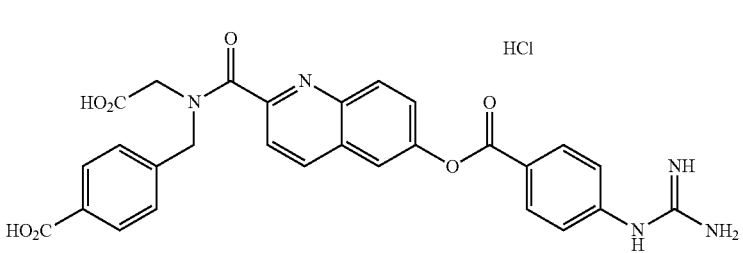 [SMILES: N=C(N)Nc1ccc(C(=O)Oc2ccc3nc(C(=O)N(CC(=O)O)Cc4ccc(C(=O)O)cc4)ccc3c2)cc1 ; Cl] HCl |

TABLE 85

| Ex | Str | |
|---|---|---|
| 105 | (structure) | HCl |
| 106 | (structure) | HCl |
| 107 | (structure) | |
| 108 | (structure) | HCl |
| 109 | (structure) | HCl |
| 110 | (structure) | TFA |

TABLE 86
| Ex | Str |
|---|---|
| 111 | 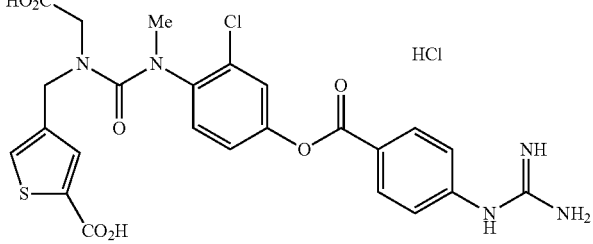 |
| 112 | 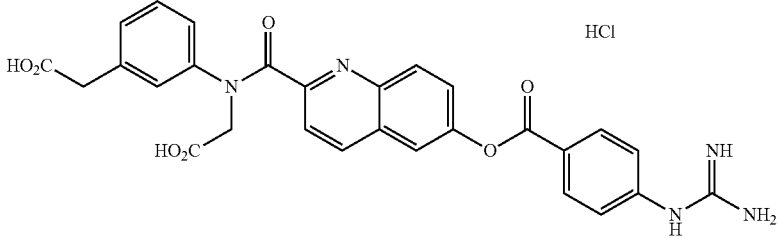 [SMILES: N=C(N)Nc1ccc(C(=O)Oc2ccc3nc(C(=O)N(CC(=O)O)c4cccc(CC(=O)O)c4)ccc3c2)cc1 ; Cl] |
| 113 | 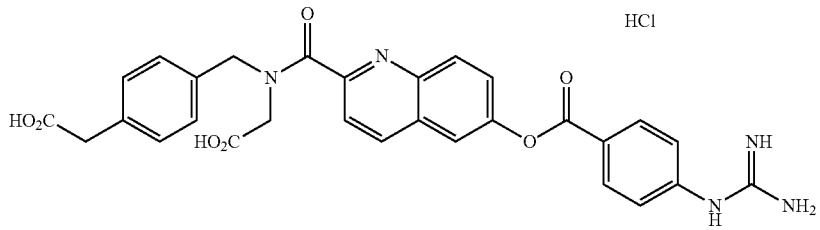 [SMILES: N=C(N)Nc1ccc(C(=O)Oc2ccc3nc(C(=O)N(CC(=O)O)Cc4ccc(CC(=O)O)cc4)ccc3c2)cc1 ; Cl] |
| 114 | 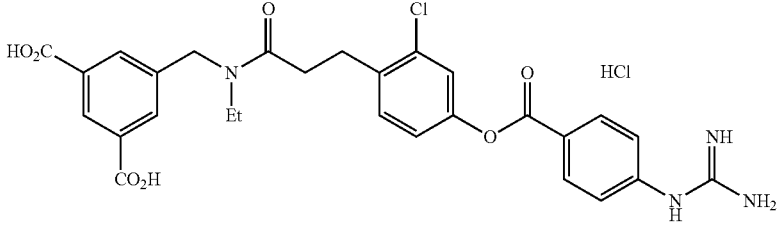 [SMILES: CCN(Cc1cc(C(=O)O)cc(C(=O)O)c1)C(=O)CCc1ccc(OC(=O)c2ccc(NC(=N)N)cc2)cc1Cl ; Cl] |
| 115 | 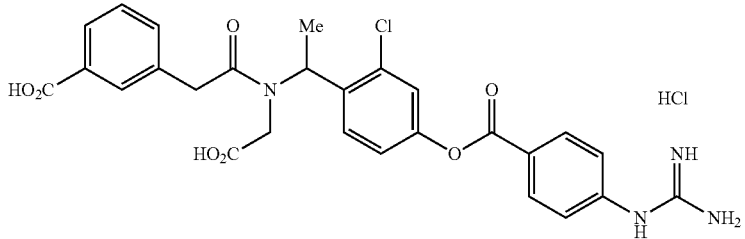 [SMILES: CC(c1ccc(OC(=O)c2ccc(NC(=N)N)cc2)cc1Cl)N(CC(=O)O)C(=O)Cc1cccc(C(=O)O)c1 ; Cl] |
| 116 | 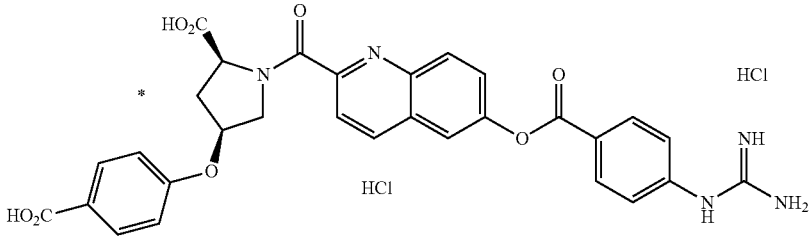 |

TABLE 87

| Ex | Str |
|---|---|
| 117 | |
| 118 | |
| 119 | |
| 120 | |
| 121 | |
| 122 | |

TABLE 88
| Ex | Str |
|---|---|
| 123 | 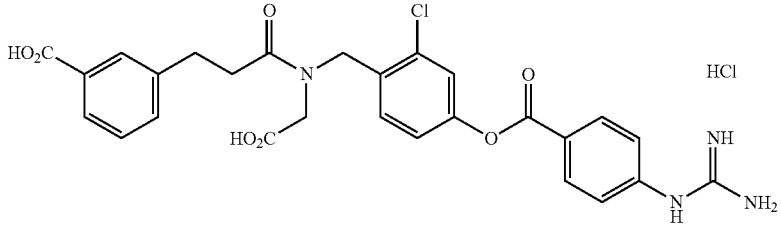 [SMILES: N=C(N)Nc1ccc(C(=O)Oc2ccc(CN(CC(=O)O)C(=O)CCc3cccc(C(=O)O)c3)c(Cl)c2)cc1 ; Cl] HCl |
| 124 | 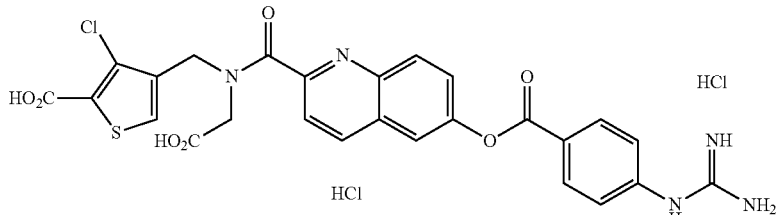 HCl  HCl |
| 125 | 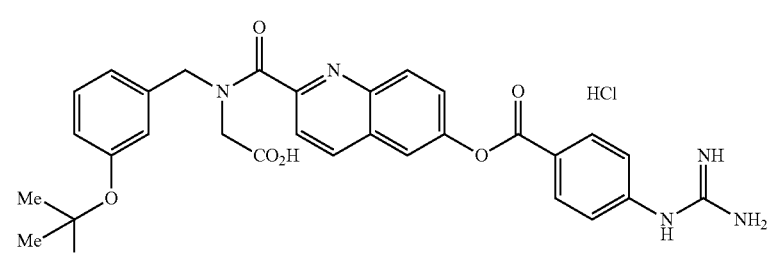 HCl |
| 126 | 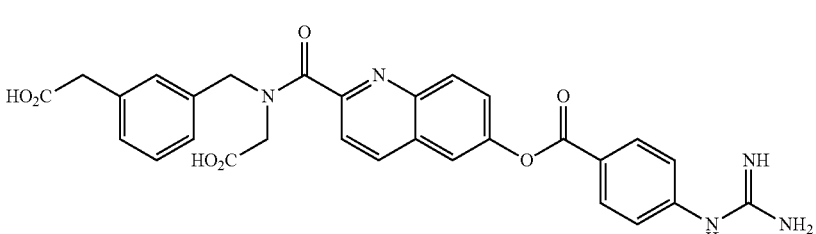 |
| 127 | 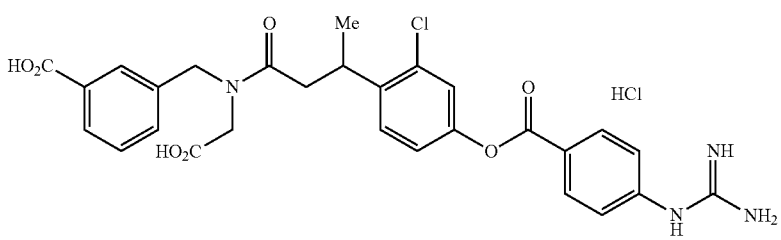 [SMILES: CC(CC(=O)N(CC(=O)O)Cc1cccc(C(=O)O)c1)c1ccc(OC(=O)c2ccc(NC(=N)N)cc2)cc1Cl ; Cl] HCl |
| 128 | 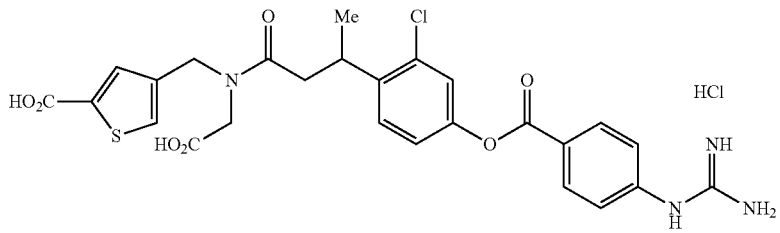 [SMILES: CC(CC(=O)N(CC(=O)O)Cc1csc(C(=O)O)c1)c1ccc(OC(=O)c2ccc(NC(=N)N)cc2)cc1Cl ; Cl] HCl |

TABLE 89

| Ex | Str |
|---|---|
| 129 | (structure: 3-carboxybenzyl-N-(carboxymethyl)-N-acyl with α-methyl propanoyl linked to 2-chloro-4-{[4-(guanidino)benzoyl]oxy}phenyl; HCl) |
| 130 | (structure: 5-carboxythiophen-3-ylmethyl-N-(carboxymethyl)-N-acyl with α-methyl propanoyl linked to 2-chloro-4-{[4-(guanidino)benzoyl]oxy}phenyl; HCl) |
| 131 | (structure: (S)-Phe-NH-C(=O)-CH2CH2- linked to 2-chloro-4-{[4-(guanidino)benzoyl]oxy}phenyl; HCl) |
| 132 | (structure: (S)-Phe-NH-C(=O)-CH2- linked to 3-methoxy-4-{[4-(guanidino)benzoyl]oxy}phenyl; HCl) |
| 133 | (structure: (S)-Phe-NH-C(=O)-CH2- linked to 2-chloro-4-{[4-(guanidino)benzoyl]oxy}phenyl; HCl) |
| 134 | (structure: (S)-Phe-NH-C(=O)-CH2- linked to 3-fluoro-4-{[4-(guanidino)benzoyl]oxy}phenyl; HCl) |

TABLE 90

| Ex | Syn | Data |
|---|---|---|
| 1 | 1 | ESI+: 511, 513 |
| 2 | 2 | ESI+: 485, 487 |
| 3 | 3 | ESI+: 553, 555, mp: 197° C.<br>NMR1: 2.34(3H, s), 2.59-2.74(2H, m), 2.88-3.03(2H, m), 3.94-4.15(2H, m), 4.54-4.78(2H, m), 7.14-7.24(1H, m), 7.36-7.53(6H, m), 7.74(4H, s), 7.80-7.88(2H, m), 8.10-8.18(2H, m), 10.06(1H, s), 12.91(2H, brs) |
| 4 | 4 | ESI+: 542, mp: 255° C.<br>NMR1: 3.84-4.16(2H, m), 4.65-4.95(2H, m), 7.10-8.58(18H, m) |
| 5 | 5 | ESI+: 553, 555, mp: 208° C.<br>NMR1: 1.31(3H, dd, J = 6.8, 17.6 Hz), 3.36-4.96(5H, m), 7.14-7.24(1H, m), 7.28-7.61(6H, m), 7.69-7.86(2H, m), 8.10(2H, dd, J = 8.8, 14.8 Hz), 8.36(4H, brs), 12.73(2H, brs) |
| 6 | 1 | ESI+: 502 |
| 7 | 1 | ESI+: 498 |
| 8 | 1 | ESI+: 472 |
| 9 | 2 | ESI+: 486 |
| 10 | 2 | ESI+: 486 |
| 11 | 1 | ESI+: 495, 497 |
| 12 | 1 | ESI+: 495, 497 |
| 13 | 1 | ESI+: 539, 541<br>NMR1: 2.90-3.03(1H, m), 3.12-3.22(1H, m), 3.55-3.65(2H, m), 4.46-4.59(1H, m), 7.15(1H, dd, J = 2.4, 8.4 Hz), 7.25-7.48(6H, m), 7.79(4H, s), 7.85(1H, d, J = 8.4 Hz), 8.15(2H, d, J = 8.8 Hz), 8.51(1H, d, J = 8.4 Hz), 10.30(1H, brs), 12.83(2H, brs) |
| 14 | 1 | ESI+: 513, 515 |
| 15 | 1 | ESI+: 529, 531<br>NMR1: 2.88(1H, dd, J = 10.0, 14.0 Hz), 3.10(1H, dd, J = 6.0, 14.0 Hz), 3.54-3.68(2H, m), 4.43-4.55(1H, m), 7.17(1H, dd, J = 4.6, 8.0 Hz), 7.23-7.36(5H, m), 7.39-7.47(3H, m), 7.77(4H, brs), 8.15(2H, d, J = 2.8 Hz), 8.48(1H, d, J = 8.7 Hz) |
| 16 | 1 | ESI+: 525, 527<br>NMR1: 2.76-2.88(1H, m), 2.97-3.13(1H, m), 3.58-3.63(2H, m), 3.68-3.74(3H, m), 4.35-4.45(1H, m), 6.83(2H, d, J = 8.6 Hz), 7.10-7.20(3H, m), 7.32(1H, d, J = 8.5 Hz), 7.39-7.50(3H, m), 7.83(4H, brs), 8.15(2H, d, J = 8.6 Hz), 8.29-8.40(1H, m) |
| 17 | 1 | ESI+: 537 |
| 18 | 1 | ESI+: 495, 497 |
| 19 | 1 | ESI+: 495, 497 |
| 20 | 1 | ESI+: 495, 497 |
| 21 | 1 | ESI+: 484 |
| 22 | 1 | ESI+: 484 |
| 23 | 1 | ESI+: 509, 511 |
| 24 | 1 | ESI+: 497 |
| 25 | 1 | ESI+: 529 |

TABLE 91

| Ex | Syn | Data |
|---|---|---|
| 26 | 1 | ESI+: 529, 531 |
| 27 | 1 | ESI+: 529, 531 |
| 28 | 1 | ESI+: 498 |
| 29 | 1 | ESI+: 513, 515 |
| 30 | 1 | ESI+: 513, 515 |
| 31 | 1 | ESI+: 563, 565 |
| 32 | 1 | ESI+: 509, 511 |
| 33 | 1 | ESI+: 509, 511 |
| 34 | 1 | ESI+: 501 |
| 35 | 1 | ESI+: 509, 511 |
| 36 | 1 | ESI+: 553, 555<br>NMR1: 2.61-2.74(2H, m), 2.88-3.04(2H, m), 3.94-4.17(2H, m), 4.52-4.79(2H, m), 7.14-7.26(1H, m), 7.35-7.54(6H, m), 7.73-7.92(6H, m), 8.10-8.20(2H, m), 10.31-10.41(1H, m), 12.93(2H, brs) |
| 37 | 1 | ESI+: 537, 539 |
| 38 | 1 | ESI+: 529, 531 |
| 39 | 1 | ESI+: 553 |

TABLE 91-continued

| Ex | Syn | Data |
|---|---|---|
| 40 | 1 | ESI+: 553<br>NMR1: 2.95-3.08(1H, m), 3.12-3.27(1H, m), 3.48-4.27(3H, m), 4.70-4.95(1H, m), 7.12-7.36(7H, m), 7.37-7.48(3H, m), 7.80(4H, s), 8.11-8.21(2H, m), 10.33(1H, brs) |
| 41 | 1 | ESI+: 553, 555<br>NMR1: 2.34-2.42(2H, m), 2.85-2.94(2H, m), 3.60(2H, s), 4.23(2H, s), 7.15-7.45(9H, m), 7.79(4H, s), 8.09-8.17(2H, m), 10.32(1H, brs), 12.50(1H, brs) |
| 42 | 1 | ESI+: 481, 483 |
| 43 | 1 | ESI+: 553, 555 |
| 44 | 1 | ESI+: 553, 555 |
| 45 | 1 | ESI+: 567, 569<br>NMR1: 2.42-2.57(2H, m), 2.58-2.69(1H, m), 2.76-2.88(1H, m), 2.90-3.05(2H, m), 3.41-3.55(2H, m), 4.55-4.76(2H, m), 7.14-7.26(1H, m), 7.35-7.55(6H, m), 7.70-7.90(6H, m), 8.15(2H, dd, J = 6.4, 8.8 Hz), 10.40(1H, brs), 12.62(2H, brs) |
| 46 | 1 | ESI+: 481, 483 |
| 47 | 1 | ESI+: 539, 541 |
| 48 | 1 | ESI+: 507, 509 |
| 49 | 1 | ESI+: 545 |
| 50 | 1 | ESI+: 523, 525 |
| 51 | 1 | ESI+: 567, 569 |
| 52 | 1 | ESI+: 495, 497<br>NMR1: 2.57(2H, t, J = 7.6 Hz), 2.97(2H, t, J = 7.6 Hz), 4.60(2H, d, J = 6.0 Hz), 7.18-7.29(2H, m), 7.34(1H, t, J = 7.6 Hz), 7.39-7.54(5H, m), 7.75-7.92(5H, m), 8.16(2H, d, J = 8.4 Hz), 8.34(1H, t, J = 6.0 Hz), 10.45(1H, s) |

TABLE 92

| Ex | Syn | Data |
|---|---|---|
| 53 | 1 | ESI+: 553, 555<br>NMR1: 2.57(1H, t, J = 7.6 Hz), 2.70(1H, t, J = 7.6 Hz), 2.87-3.04(2H, m), 3.91-4.21(2H, m), 4.81-5.07(2H, m), 7.14-7.28(2H, m), 7.32-7.61(6H, m), 7.70-7.97(5H, m), 8.00-8.20(2H, m), 10.32(1H, s), 12.44-13.30(2H, m) |
| 54 | 1 | ESI+: 567, 569 |
| 55 | 1 | ESI+: 629, 631 |
| 56 | 1 | ESI+: 569, 571<br>NMR1: 2.83(1H, dd, J = 9.6, 13.8 Hz), 3.02(1H, dd, J = 4.8, 13.6 Hz), 3.62(2H, s), 4.37-4.47(1H, m), 4.62(2H, s), 6.78-6.85(2H, m), 7.10-7.22(3H, m), 7.31(1H, d, J = 8.8 Hz), 7.39-7.47(3H, m), 7.81(4H, s), 8.12-8.19(2H, m), 8.44(1H, d, J = 8.4 Hz), 10.36(1H, s), 12.84(1H, brs) |
| 57 | 1 | ESI+: 553 |
| 58 | 1 | ESI+: 567<br>NMR1: 2.45-2.60(2H, m), 2.76-2.99(4H, m), 3.44-3.64(2H, m), 3.96-4.23(2H, m), 7.15-7.26(1H, m), 7.28-7.53(6H, m), 7.73-7.91(6H, m), 8.15(2H, d, J = 8.8 Hz), 10.33(1H, s), 12.30-13.25(2H, m) |
| 59 | 1 | ESI+: 542<br>NMR1: 4.05-4.47(2H, m), 4.77-4.92(2H, m), 7.46-7.55(3H, m), 7.66-8.27(13H, m), 8.53-8.58(1H, m), 10.53-10.59(1H, m) |
| 60 | 1 | ESI+: 553, 555<br>NMR1: 1.33(3H, dd, J = 8.0, 16.0 Hz), 3.84-4.11(2H, m), 4.20-4.86(2H, m), 7.21-7.32(1H, m), 7.34-7.56(6H, m), 7.69-7.98(6H, m), 8.15(2H, d, J = 8.0 Hz), 10.48(1H, d, J = 4.0 Hz), 12.90(1H, brs) |
| 61 | 1 | ESI+: 554, 556<br>NMR1: 3.01(3H, s), 3.66(2H, s), 4.38(2H, s), 7.19(1H, dd, J = 2.5, 8.6 Hz), 7.28-7.49(6H, m), 7.64(1H, s), 7.72-7.88(5H, m), 8.08-8.16(2H, m), 10.33(1H, s), 12.30-13.04(2H, m) |
| 62 | 1 | ESI+: 509, 511 |
| 63 | 1 | ESI+: 559<br>NMR1: 2.55-2.65(1H, m), 2.66-2.77(1H, m), 2.87-3.01(2H, m), 3.95-4.17(2H, m), 4.43-4.66(2H, m), 7.17-7.25(1H, m), 7.34-7.50(4H, m), 7.59-7.70(2H, m), 7.85(4H, brs), 8.07-8.19(2H, m), 10.45-10.52(1H, m), |

TABLE 92-continued

| Ex | Syn | Data |
|---|---|---|
| 64 | 1 | ESI+: 597, 599 |
| | | NMR1: 2.61-2.75(2H, m), 2.87-3.04(2H, m), 3.97-4.23(2H, m), 4.58-4.87(2H, m), 7.12-7.26(1H, m), 7.31-7.51 (4H, m), 7.85(4H, s), 8.02-8.19(4H, m), 8.34-8.40(1H, m), 10.49(1H, brs), 13.15(2H, brs) |
| 65 | 1 | ESI+: 525, 527 |
| 66 | 1 | ESI+: 553, 555 |
| | | NMR1: 2.84-3.09(2H, m), 3.48-3.88(4H, m), 3.94-4.30(2H, m), 7.15-7.30(1H, m), 7.34-7.59(6H, m), 7.68-7.94(6H, m), 8.08-8.22(2H, m), 10.34-10.46(1H, m), 12.86(1H, brs) |
| 67 | 2 | ESI+: 577, 579 |
| 68 | 1 | ESI+: 603 |

TABLE 93

| Ex | Syn | Data |
|---|---|---|
| 69 | 1 | ESI+: 593, 595 |
| 70 | 1 | ESI+: 583 |
| 71 | 1 | ESI+: 572 |
| | | NMR1: 3.21(2H, d, J = 8.0 Hz), 4.60(2H, s), 4.71-4.80(1H, m), 6.82(2H, d, J = 8.0 Hz), 7.19(2H, d, J = 8.0 Hz), 7.48(2H, d, J = 8.0 Hz), 7.77-9.96(5H, m), 8.06(1H, d, J = 4.0 Hz), 8.18(1H, d, 12.0 Hz), 8.24(3H, d, J = 8.0 Hz), 8.61(1H, d, J = 8.0 Hz), 8.85(1H, d, J = 8.0 Hz), 10.50(1H, s) |
| 72 | 1 | ESI+: 606 |
| 73 | 1 | ESI+: 608, 610 |
| 74 | 1 | ESI+: 579 |
| 75 | 1 | ESI+: 553 |
| 76 | 1 | ESI+: 650 |
| 77 | 1 | ESI+: 554 |
| 78 | 1 | ESI+: 567, 569 |
| | | NMR1: 2.60-2.75(2H, m), 2.88-3.04(2H, m), 3.50-3.60(2H, m), 3.88-4.13(2H, m), 4.45-4.70(2H, m), 7.04-7.52(9H, m), 7.72-7.91(4H, m), 8.11-8.20(2H, m), 10.31-10.41(1H, m), 12.00-13.30(2H, m) |
| 79 | 1 | ESI+: 604 |
| 80 | 1 | ESI+: 548 |
| | | NMR1: 4.06-4.46(2H, m), 4.64-4.80(2H, m), 7.47(2H, d, J = 8.0 Hz), 7.75-8.14(10H, m), 8.23(2H, d, J = 8.0 Hz), 8.51-8.60(1H, m), 10.39-10.48(1H, m) |
| 81 | 1 | ESI+: 568 |
| 82 | 1 | ESI+: 621, 623 |
| 83 | 1 | ESI+: 560, 562 |
| 84 | 1 | ESI+: 571 |
| 85 | 1 | ESI+: 583, 585 |
| 86 | 1 | ESI+: 571 |
| 87 | 1 | ESI+: 523, 525 |
| 88 | 1 | ESI+: 539 |
| 89 | 1 | ESI+: 569 |
| 90 | 1 | ESI+: 615, 617 |
| 91 | 1 | ESI+: 559 |
| 92 | 1 | ESI+: 559 |
| 93 | 1 | ESI+: 629 |
| 94 | 2 | ESI+: 568 |
| 95 | 2 | ESR: 597, 599 |
| | | NMR1: 1.47(6H, s), 2.75-2.88(1H, m), 2.96-3.08(1H, m), 3.55-3.67(2H, m), 4.33-4.44(1H, m), 6.73(2H, d, J = 8.8 Hz), 7.07-7.22(3H, m), 7.33(1H, d, J = 8.4 Hz), 7.38-7.47(3H, m), 7.95(4H, s), 8.14(2H, d, J = 8.4 Hz), 8.28-8.40(1H, m) |
| 96 | 2 | ESI+: 611, 613 |
| | | NMR1: 1.44-1.48(6H, m), 2.38-2.46(2H, m), 2.73-2.90(3H, m), 2.98(1H, dd, J = 4.8, 13.6 Hz), 4.34-4.43(1H, m), 6.70-6.76(2H, m), 7.07-7.12(2H, m), 7.17(1H, dd, J = 2.4, 8.4 Hz), 7.32(1H, d, J = 8.4 Hz), 7.41-7.46(3H, m), 7.80(4H, m), 8.12-8.18(2H, m), 8.25(1H, d, J = 8.0 Hz), 10.32(1H, s), 12.82(2H, brs) |

TABLE 94

| Ex | Syn | Data |
|---|---|---|
| 97 | 1 | ESI+: 564 |
| 98 | 1 | ESI+: 555 |
| 99 | 2 | ESI+: 574 |
| 100 | 2 | ESI+: 566, 568 |
| 101 | 2 | ESI+: 566, 568 |
| 102 | 1 | ESI+: 562 |
| | | NMR1: 1.37(3H, t, J = 7.8 Hz), 4.28-4.44(1H, m), 4.53-5.09(2H, m), 7.45(2H, d, J = 8.4 Hz), 7.58-8.55(12H, m) |
| 103 | 2 | ESI+: 572 |
| 104 | 2 | ESI+: 542 |
| 105 | 1 | ESI+: 537 |
| 106 | 2 | ESI+: 556 |
| 107 | 2 | ESI+: 598 |
| 108 | 2 | ESI+: 553 |
| | | NMR1: 1.33(3H, dd, J = 8.0, 16.0 Hz), 3.84-4.10(2H, m), 4.21-4.85(3H, m), 7.07-7.98(13H, m), 8.15(2H, d, J = 8.0 Hz), 10.49(1H, d, J = 4.0 Hz), 12.92(1H, brs) |
| 109 | 2 | ESI+: 553 |
| 110 | 2 | ESI+: 553, 555 |
| 111 | 1 | ESI+: 560, 562 |
| | | NMR1: 3.04(3H, s), 3.68(2H, s), 4.26(2H, s), 7.23(1H, dd, J = 2.8, 8.8 Hz), 7.37-7.48(5H, m), 7.51(d, 1H, J = 2.8 Hz), 7.83(4H, s), 8.10-8.16(2H, m), 10.41(1H, s) |
| 112 | 2 | ESI+: 542 |
| 113 | 2 | ESI+: 556 |
| | | NMR1: 3.34-3.83(2H, m), 4.02-4.38(2H, m), 4.70-4.84(2H, m), 7.25(2H, dd, J = 8.4, 15.2 Hz), 7.33-7.41(2H, m), 7.43-7.51(2H, m), 7.74-7.92(6H, m), 8.00(1H, d, J = 2.8 Hz), 8.05-8.13(1H, m), 8.19-8.27(2H, m), 8.51-8.57(1H, m), 10.31(1H, d, J = 4.4 Hz) |
| 114 | 1 | ESI+: 567 |
| 115 | 2 | ESI+: 553, 555 |
| 116 | 1 | ESI+: 584 |
| 117 | 1 | ESI+: 556 |
| 118 | 1 | ESI+: 495, 497 |
| 119 | 1 | ESI+: 486 |
| | | NMR1: 3.08(1H, dd, J = 10.8, 13.9 Hz), 3.22(1H, dd, J = 4.4, 13.9 Hz), 4.61-4.70(1H, m), 6.94(1H, dd, J = 2.1, 8.6 Hz), 7.14-7.36(7H, m), 7.44(2H, d, J = 8.8 Hz), 7.70(1H, d, J = 8.8 Hz), 7.79(4H, brs), 8.18(2H, d, J = 8.8 Hz), 8.75(1H, d, J = 8.4 Hz), 10.35(1H, brs), 11.64-11.70(1H, m), 12.83(1H, brs) |
| 120 | 2 | ESI+: 542 |
| 121 | 2 | ESI+: 562 |
| 122 | 1 | ESI+: 595, 597 |
| 123 | 2 | ESI+: 553 |
| 124 | 2 | ESI+: 582, 584 |

TABLE 95

| Ex | Syn | Data |
|---|---|---|
| 125 | 2 | ESI+: 600 |
| 126 | 2 | ESI+: 556 |
| 127 | 2 | ESI+: 567, 569 |
| 128 | 2 | ESI+: 573 |
| 129 | 2 | ESI+: 567 |
| 130 | 2 | ESI+: 573 |
| 131 | 1 | ESI+: 509, 511 |
| 132 | 1 | ESI+: 491 |
| 133 | 1 | ESI+: 495, 497 |
| 134 | 1 | ESI+: 479 |

TABLE 96

| Ex | Str | ESI+ | RT |
|---|---|---|---|
| A1 | (L-Asp conjugate) | 443 | 1.42 |
| A2 | (D-Pro conjugate) | 425 | 1.63 |
| A3 | (L-Glu conjugate) | 457 | 1.4 |
| A4 | (D-Ala conjugate) | 399 | 1.55 |
| A5 | (L-Pro conjugate) | 425 | 1.62 |
| A6 | (D-Glu conjugate) | 457 | 1.42 |

TABLE 97

| Ex | Str | ESI+ | RT |
|---|---|---|---|
| A7 | | 461 | 1.84 |
| A8 | | 413 | 1.52 |
| A9 | | 489 | 1.96 |
| A10 | | 489 | 1.94 |
| A11 | | 475 | 1.8 |
| A12 | | 455 | 1.89 |

TABLE 98

| Ex | Str | ESI+ | RT |
|---|---|---|---|
| A13 | | 455 | 1.89 |
| A14 | | 399 | 1.55 |
| A15 | | 429 | 1.38 |
| A16 | | 453 | 1.76 |
| A17 | | 443 | 1.42 |
| A18 | | 441 | 1.95 |

TABLE 99
| Ex | Str | ESI+ | RT |
|---|---|---|---|
| A19 | 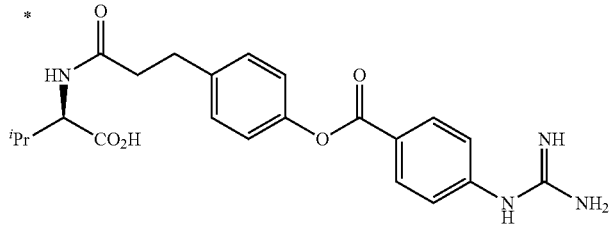 | 427 | 1.77 |
| A20 | 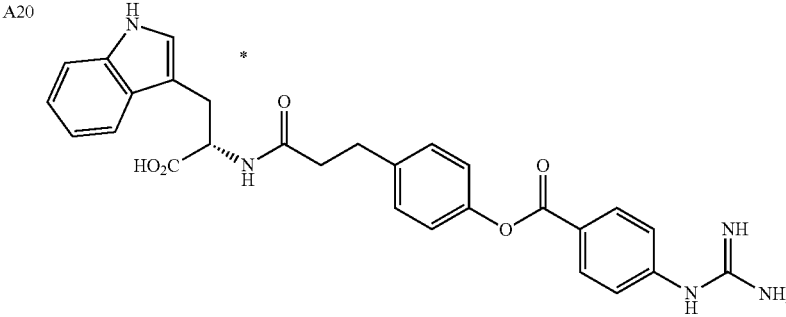 | 514 | 1.94 |
| A21 | 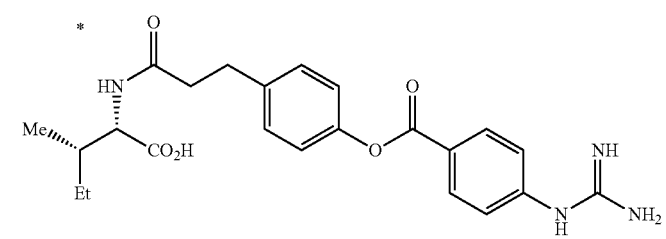 | 441 | 1.89 |
| A22 | 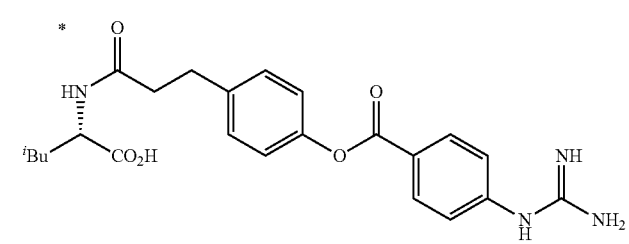 | 441 | 1.91 |
| A23 | 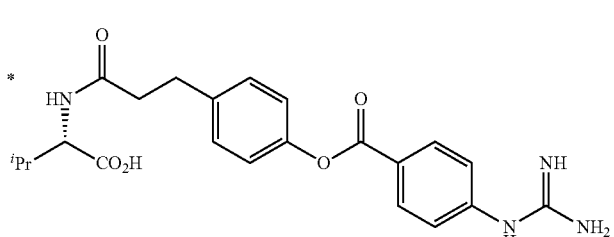 | 427 | 1.73 |
| A24 | 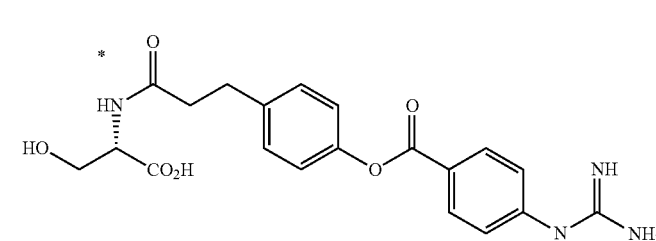 | 415 | 1.37 |

TABLE 100

| Ex | Str | ESI+ | RT |
|---|---|---|---|
| A25 | | 399 | 1.54 |
| A26 | | 411 | 1.55 |
| A27 | | 385 | 1.37 |
| A28 | | 411 | 1.55 |
| A29 | | 447 | 1.73 |
| A30 | | 399 | 1.35 |

TABLE 101

| Ex | Str | ESI+ | RT |
|---|---|---|---|
| A31 | | 475 | 1.85 |
| A32 | | 475 | 1.85 |
| A33 | | 461 | 1.72 |
| A34 | | 441 | 1.83 |
| A35 | | 415 | 1.3 |
| A36 | | 439 | 1.63 |
| A37 | | 429 | 1.26 |

TABLE 102

| Ex | Str | ESI+ | RT |
|---|---|---|---|
| A38 | | 427 | 1.86 |
| A39 | | 413 | 1.68 |
| A40 | | 500 | 1.88 |
| A41 | | 427 | 1.85 |
| A42 | | 427 | 1.86 |
| A43 | | 413 | 1.62 |

TABLE 103

| Ex | Str | ESI+ | RT |
|---|---|---|---|
| A44 | 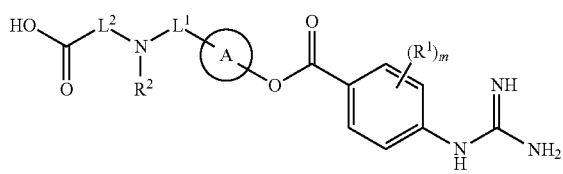 | 401 | 1.19 |
| A45 | 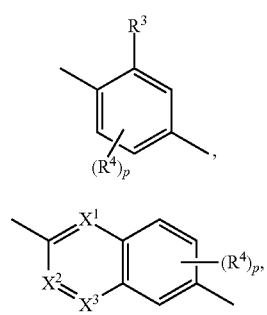 | 385 | 1.38 |

INDUSTRIAL APPLICABILITY

The compound of the formula (I) or a salt thereof has a trypsin inhibitory action, and can be used as an agent for preventing and/or treating renal disease as an agent which will substitute low-protein diet therapy, and an agent for preventing and/or treating trypsin-related diseases, for example, pancreatitis, gastroesophageal reflux disease, hepatic encephalopathy, influenza, and the like.

The invention claimed is:

1. A compound of formula (I) or a salt thereof:

(I)

wherein

Ring A is of formula (a), (b), or (c):

(a)

(b)

(c)

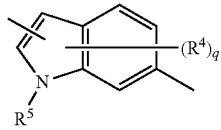

each $R^1$ is independently a lower alkyl, halogen, or —OH,
$R^2$ is H; lower alkyl optionally substituted with at least one substituent selected from the group consisting of halogen, —$CO_2H$, —OH, —O-lower alkyl, optionally substituted cycloalkyl, optionally substituted aryl, optionally substituted aromatic heterocycle, and optionally substituted non-aromatic heterocycle; optionally substituted cycloalkyl; optionally substituted aryl; optionally substituted aromatic heterocycle; optionally substituted non-aromatic heterocycle; or optionally substituted —C(O)-lower alkylene-aryl,
$L^1$ is —$Y^1$-lower alkylene-$Y^2$— or —C(O)—N($R^6$)—, or if Ring A is of formula (b) or formula (c), then $L^1$ is optionally —C(O)—,
$L^2$ is a lower alkylene optionally substituted with at least one substituent selected from the group consisting of halogen, —$CO_2H$, —OH, —O-lower alkyl, optionally substituted cycloalkyl, optionally substituted aryl, optionally substituted aromatic heterocycle, and optionally substituted non-aromatic heterocycle; —$Y^3$-cyclohexanediyl-$Y^4$— or —$Y^3$-phenylene-$Y^4$—, and $L^2$ is optionally combined with the nitrogen atom bonded thereto and the $R^2$ group on the nitrogen atom to form an optionally substituted cyclic amino,
$R^3$ is H, lower alkyl optionally substituted with halogen, halogen, —OH, —O-lower alkyl, cycloalkyl, aryl, aromatic heterocycle, or non-aromatic heterocycle, provided that if -$L^2$-N($R^2$)-$L^1$- is —$(CH_2)_n$—NH—C(O)—$(CH_2)_n$—, —CH(—$R^z$)—NH—C(O)—$(CH_2)_n$—, or —$(CH_2)_r$-phenylene-NH—C(O)—$(CH_2)_n$— wherein each n is independently an integer of from 0 to 5, r is 0 or 1, $R^z$ is —$CH_2$—C(O)—$OCH_3$ or benzyl optionally substituted with at least one selected from the group consisting of halogen, nitro, lower alkyl, —OH and —O-lower alkyl, then $R^3$ is a group other than H, each $R^4$ is independently a lower alkyl optionally substituted with halogen, halogen, —OH, —O-lower alkyl, cycloalkyl, aryl, aromatic heterocycle, or non-aromatic heterocycle, $R^5$ is H or lower alkyl, $R^6$ is H or lower alkyl, $X^1$, $X^2$ and $X^3$ are each independently CH or N, provided that at least one of $X^1$, $X^2$ and $X^3$ is N, $Y^1$ is a bond or —C(O)—, $Y^2$ is a bond, —N($R^6$)— or —C(O)—N($R^6$)—, each $Y^3$ is independently a bond or lower alkylene, each $Y^4$ is independently a bond, lower alkylene or —C(O)—, m is an integer of from 0 to 4, p is an integer of from 0 to 3, and q is an integer of from 0 to 4.

2. The compound or a salt thereof according to claim 1, wherein Ring A is of formula (a) or formula (b), m is 0, and p is an integer of 0 or 1.

3. The compound or a salt thereof according to claim 2, wherein Ring A is of formula (a), and $R^3$ is a lower alkyl optionally substituted with halogen, halogen, cycloalkyl, or aryl.

4. The compound or a salt thereof according to claim 3, wherein $R^2$ is H or a lower alkyl optionally substituted with at least one substituent selected from the group consisting of halogen, —$CO_2H$, —OH, —O-lower alkyl, optionally substituted cycloalkyl, optionally substituted aryl, optionally substituted aromatic heterocycle, and optionally substituted non-aromatic heterocycle, $L^1$ is -lower alkylene-, —C(O)-lower alkylene-, -lower alkylene-C(O)—N($R^6$)—, or —C(O)—N($R^6$)—, $L^2$ is a lower alkylene optionally substituted with at least one substituent selected from the group consisting of halogen, —$CO_2H$, —OH, —O-lower alkyl, optionally substituted cycloalkyl, optionally substituted aryl, optionally substituted aromatic heterocycle, and optionally substituted non-aromatic heterocycle; -lower alkylene-phenylene-; -phenylene-lower alkylene-; or -lower alkylene-phenylene-lower alkylene-.

5. The compound or a salt thereof according to claim 4, wherein $R^3$ is halogen, $R^2$ is H or a lower alkyl substituted with at least one substituent selected from the group consisting of —$CO_2H$, aryl substituted with one or more —$CO_2H$, and aromatic heterocycle substituted with one or more —$CO_2H$, p is 0, $L^1$ is —C(O)-lower alkylene- or —C(O)—N($R^6$)—, $L^2$ is lower alkylene optionally substituted with aryl which is optionally substituted with at least one substituent selected from the group consisting of —$CO_2H$ and —O-lower alkylene-$CO_2H$, -lower alkylene-phenylene-, -phenylene-lower alkylene-, or -lower alkylene-phenylene-lower alkylene-.

6. The compound or a salt thereof according to claim 5, wherein $L^2$ is lower alkylene optionally substituted with aryl which is optionally substituted with O-lower alkylene-$CO_2H$ or -phenylene-lower alkylene-.

7. The compound or a salt thereof according to claim 1, which is

N-({4-[(4-carbamimidamidobenzoyl)oxy]-2-chlorophenyl}acetyl)-4-carboxy-L-phenylalanine, 3-{[(3-{4-[(4-carbamimidamidobenzoyl)oxy]-2-chlorophenyl}propanoyl)(carboxymethyl)amino]methyl}benzoic acid, N-(3-{4-[(4-carbamimidamidobenzoyl)oxy]-2-chlorophenyl}propanoyl)-N-[3-(carboxymethyl)phenyl]glycine, 3-{[(3-{4-[(4-carbamimidamidobenzoyl)oxy]-2-chlorophenyl}propanoyl)(2-carboxyethyl)amino]methyl}benzoic acid, 2-{[(3-{4-[(4-carbamimidamidobenzoyl)oxy]-2-chlorophenyl}propanoyl)amino]methyl}benzoic acid, 2-{[(3-{4-[(4-carbamimidamidobenzoyl)oxy]-2-chlorophenyl}propanoyl)(carboxymethyl)amino]methyl}benzoic acid, N-({4-[(4-carbamimidamidobenzoyl)oxy]-2-chlorophenyl}acetyl)-O-(carboxymethyl)-L-tyrosine, 3-{2-[(3-{4-[(4-carbamimidamidobenzoyl)oxy]-2-chlorophenyl}propanoyl)(carboxymethyl)amino]ethyl}benzoic acid, 3-{[({6-[(4-carbamimidamidobenzoyl)oxy]quinolin-2-yl}carbonyl)(carboxymethyl)amino]methyl}benzoic acid, 3-{[(2-{4-[(4-carbamimidamidobenzoyl)oxy]-2-chlorophenyl}propanoyl)(carboxymethyl)amino]methyl}benzoic acid, 3-({[{4-[(4-carbamimidamidobenzoyl)oxy]-2-chlorophenyl}(methyl)carbamoyl](carboxymethyl)amino}methyl)benzoic acid, 4-{[(3-{[4-(4-carbamimidamidobenzoyl)oxy]-2-chlorophenyl}propanoyl)(carboxymethyl)amino]methyl}thiophene-2-carboxylic acid, 5-{[(3-{4-[(4-carbamimidamidobenzoyl)oxy]-2-chlorophenyl}propanoyl)(carboxymethyl)amino]methyl}isophthalic acid, N-(3-{4-[(4-carbamimidamidobenzoyl)oxy]-2-chlorophenyl}propanoyl)-N-[3-(carboxymethyl)benzyl]glycine, 4-{[({6-[(4-carbamimidamidobenzoyl)oxy]quinolin-2-yl}carbonyl)(carboxymethyl)amino]methyl}thiophene-2-carboxylic acid, N-({4-[(4-carbamimidamidobenzoyl)oxy]-2-chlorophenyl}acetyl)-O-(2-carboxypropan-2-yl)-L-tyrosine, N-(3-{4-[(4-carbamimidamidobenzoyl)oxy]-2-chlorophenyl}propanoyl)-O-(2-carboxypropan-2-yl)-L-tyrosine, 4-({({6-[(4-carbamimidamidobenzoyl)oxy]quinolin-2-yl}carbonyl)[(1R)-1-carboxyethyl]amino}methyl)thiophene-2-carboxylic acid, 3-{[(2-{4-[(4-carbamimidamidobenzoyl)oxy]-2-chlorophenyl}propanoyl)(carboxymethyl)amino]methyl}benzoic acid, 4-({[{4-[(4-carbamimidamidobenzoyl)oxy]-2-chlorophenyl}-(methyl)carbamoyl](carboxymethyl)amino}methyl)thiophene-2-carboxylic acid, N-({6-[(4-carbamimidamidobenzoyl)oxy]quinolin-2-yl}carbonyl)-N-[4-(carboxymethyl)benzyl]glycine, or N-({6-[(4-carbamimidamidobenzoyl)oxy]-1H-indol-2-yl}carbonyl)-L-phenylalanine, or a salt thereof.

8. A pharmaceutical composition comprising a compound or a salt thereof according to claim 7 and a pharmaceutically acceptable excipient.

9. The pharmaceutical composition according to claim 8, suitable for treating a renal disease.

10. A method of manufacture of a pharmaceutical composition, the method comprising:
manufacturing the pharmaceutical composition with a compound or a salt thereof according to claim 7,
wherein the pharmaceutical composition is suitable for treating a renal disease.

11. The compound or a salt thereof according to claim 7, wherein the compound is suitable for treating a renal disease.

12. A method for treating a renal disease, the method comprising administering, to a subject in need thereof, an effective amount of a compound or a salt thereof according to claim 7.

13. The compound or a salt thereof according to claim 7 wherein the compound is 3-{[(3-{4-[(4-carbamimidamidobenzoyl)oxy]-2-chlorophenyl}propanoyl)(carboxymethyl)amino]methyl}benzoic acid.

14. The compound or a salt thereof according to claim 7 wherein the compound is N-(3-{4-[(4-carbamimidamidobenzoyl)oxy]-2-chlorophenyl}propanoyl)-N-[3-(carboxymethyl)phenyl]glycine.

15. The compound or a salt thereof according to claim 7 wherein the compound is 2-{[(3-{4-[(4-carbamimidamidobenzoyl)oxy]-2-chlorophenyl}propanoyl)(carboxymethyl)amino]methyl}benzoic acid.

16. The compound or a salt thereof according to claim 7 wherein the compound is 3-{[(2-{4-[(4-carbamimidamidobenzoyl)oxy]-2-chlorophenyl}propanoyl)(carboxymethyl)amino]methyl}benzoic acid.

17. The compound or a salt thereof according to claim 7 wherein the compound is 4-{[(3-{4-[(4-carbamimidamidobenzoyl)oxy]-2-chlorophenyl}propanoyl)(carboxymethyl)amino]methyl}thiophene-2-carboxylic acid.

18. The compound or a salt thereof according to claim 1, wherein Ring A is of formula (a):

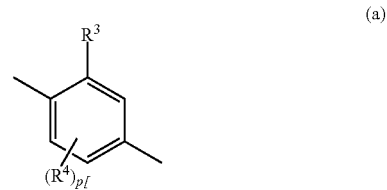

(a)

* * * * *

UNITED STATES PATENT AND TRADEMARK OFFICE
CERTIFICATE OF CORRECTION

PATENT NO. : 9,199,927 B2
APPLICATION NO. : 14/344377
DATED : December 1, 2015
INVENTOR(S) : Jiro Fujiyasu et al.

It is certified that error appears in the above-identified patent and that said Letters Patent is hereby corrected as shown below:

In the Claims

Column 240, lines 15 to 20:

"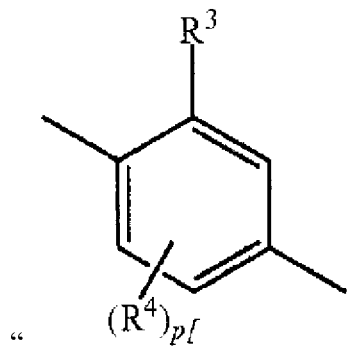  (a)"

should read

--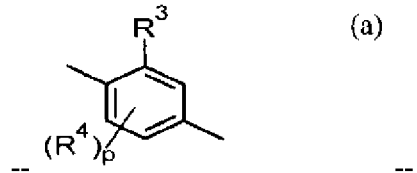  (a)--

Signed and Sealed this
Fourteenth Day of June, 2016

Michelle K. Lee
*Director of the United States Patent and Trademark Office*